US012595518B1

(12) United States Patent
Perou et al.

(10) Patent No.: US 12,595,518 B1
(45) Date of Patent: *Apr. 7, 2026

(54) METHODS FOR ASSAYING ENRICHED NUCLEIC ACIDS

(71) Applicants:The University of North Carolina at Chapel Hill, Chapel Hill, NC (US); Washington University, St. Louis, MO (US); University of Utah Research Foundation, Salt Lake City, UT (US); British Columbia Cancer Agency Branch, Vancouver BC (CA)

(72) Inventors: Charles M. Perou, Carrboro, NC (US); Joel S. Parker, Apex, NC (US); James Stephen Marron, Durham, NC (US); Andrew Nobel, Chapel Hill, NC (US); Philip S. Bernard, Salt Lake City, UT (US); Matthew J. Ellis, St. Louis, MO (US); Elaine Mardis, Troy, IL (US); Torsten O. Nielsen, Vancouver (CA); Maggie Chon U. Cheang, Vancouver (CA)

(73) Assignees: British Columbia Cancer Agency Branch, Vancouver (CA); The University of North Carolina at Chapel Hill, Chapel Hill, NC (US); University of Utah Research Foundation, Salt Lake City, UT (US); Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/905,647

(22) Filed: Oct. 3, 2024

Related U.S. Application Data

(60) Continuation of application No. 18/158,396, filed on Jan. 23, 2023, which is a continuation of application No. 16/656,984, filed on Oct. 18, 2019, now abandoned, which is a continuation of application No. 14/931,594, filed on Nov. 3, 2015, now abandoned, which is a division of application No. 12/995,450, filed as application No. PCT/US2009/045820 on Jun. 1, 2009, now Pat. No. 9,631,239.

(60) Provisional application No. 61/057,508, filed on May 30, 2008.

(51) Int. Cl.
| | |
|---|---|
| *C12Q 1/6886* | (2018.01) |
| *C12N 15/10* | (2006.01) |
| *C12Q 1/6813* | (2018.01) |
| *C12Q 1/6869* | (2018.01) |

(52) U.S. Cl.
CPC ....... *C12Q 1/6886* (2013.01); *C12N 15/1096* (2013.01); *C12Q 1/6813* (2013.01); *C12Q 1/6869* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 4,843,155 | A | 6/1989 | Chomczynski |
| 5,384,261 | A | 1/1995 | Winkler et al. |
| 5,708,153 | A | 1/1998 | Dower et al. |
| 5,770,358 | A | 6/1998 | Dower et al. |
| 5,789,162 | A | 8/1998 | Dower et al. |
| 5,800,992 | A | 9/1998 | Fodor et al. |
| 5,854,033 | A | 12/1998 | Lizardi |
| 5,856,174 | A | 1/1999 | Lipshutz et al. |
| 5,922,591 | A | 7/1999 | Anderson et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,344,316 | B1 | 2/2002 | Lockhart et al. |
| 6,576,421 | B1 | 6/2003 | Westbrook |
| 8,415,102 | B2 | 4/2013 | Geiss et al. |
| 9,181,588 | B2 | 11/2015 | Perou et al. |
| 9,631,239 | B2 | 4/2017 | Perou et al. |
| 10,392,663 | B2 * | 8/2019 | Emerson .............. C12Q 1/6881 |
| 2002/0168639 | A1 | 11/2002 | Muraca |

(Continued)

FOREIGN PATENT DOCUMENTS

| | | | |
|---|---|---|---|
| EP | 1 641 810 B1 | 6/2004 |
| WO | WO 2004/111603 A2 | 12/2004 |

(Continued)

OTHER PUBLICATIONS

Agilent-012097 Human 1A Microarray (V2) G4110B (Feature Number version); Published on Jan. 2, 2004; NCBI GEO accession: GPL887 (Year: 2004).*

(Continued)

*Primary Examiner* — Aaron A Priest
*Assistant Examiner* — Tian Nmn Yu

(74) *Attorney, Agent, or Firm* — Pamela J. Sherwood; Andrew R. Guzman; Bozicevic, Field & Francis LLP

(57) ABSTRACT

In an aspect, a method comprises providing a biological sample of a subject, and assaying nucleic acid molecules derived from RNA expression products of the biological sample to determine an RNA expression level of a plurality of genes, wherein the assaying comprises use of probes having sequences complementary to the nucleic acid molecules derived from the RNA expression products, to enrich the nucleic acid molecules for the plurality of genes.

24 Claims, 14 Drawing Sheets

Specification includes a Sequence Listing.

(56)                References Cited

U.S. PATENT DOCUMENTS

| | | | |
|---|---|---|---|
| 2003/0027208 A1 | 2/2003 | Horwitz et al. | |
| 2003/0099987 A1 | 5/2003 | Westbrook | |
| 2004/0235039 A1 | 11/2004 | Gray et al. | |
| 2005/0071087 A1 | 3/2005 | Anderson | |
| 2006/0134667 A1 | 6/2006 | Narahara et al. | |
| 2008/0032293 A1 | 2/2008 | Szabo et al. | |
| 2008/0124721 A1* | 5/2008 | Fuchs ............. | G01N 33/57484 |
| | | | 435/6.12 |
| 2009/0239223 A1 | 9/2009 | Gehmann et al. | |
| 2009/0299640 A1 | 12/2009 | Ellis | |
| 2010/0015607 A1 | 1/2010 | Geiss et al. | |
| 2010/0047924 A1 | 2/2010 | Webster et al. | |
| 2010/0261026 A1 | 10/2010 | Ferree et al. | |
| 2010/0279957 A1 | 11/2010 | Potti et al. | |
| 2011/0129822 A1 | 6/2011 | Shen et al. | |
| 2011/0145176 A1 | 6/2011 | Perou et al. | |
| 2011/0150979 A1 | 6/2011 | Ray et al. | |
| 2011/0230360 A1 | 9/2011 | Stephan et al. | |
| 2011/0286960 A1 | 11/2011 | Vainas et al. | |
| 2013/0004482 A1 | 1/2013 | Perou et al. | |
| 2013/0337444 A1 | 12/2013 | Ferree et al. | |
| 2013/0345161 A1 | 12/2013 | Perou et al. | |
| 2014/0017688 A1 | 1/2014 | Webster et al. | |
| 2014/0037620 A1 | 2/2014 | Ferree et al. | |
| 2014/0087959 A1 | 3/2014 | Ellis et al. | |
| 2014/0154681 A1 | 6/2014 | Wallden | |
| 2015/0072021 A1 | 3/2015 | Cheang et al. | |
| 2016/0017438 A1 | 1/2016 | Perou et al. | |
| 2016/0153051 A1 | 6/2016 | Perou et al. | |
| 2016/0168645 A1 | 6/2016 | Perou et al. | |

FOREIGN PATENT DOCUMENTS

| | | | |
|---|---|---|---|
| WO | WO 2005/100606 A2 | 10/2005 | |
| WO | WO 2006/010150 A2 | 1/2006 | |
| WO | WO 2007/061876 A2 | 5/2007 | |
| WO | WO 2007/076129 A2 | 7/2007 | |
| WO | WO 2007/076132 A2 | 7/2007 | |
| WO | WO 2007/084992 A2 | 7/2007 | |
| WO | WO 2008/124847 A2 | 10/2008 | |
| WO | WO 2009/158143 A1 | 12/2009 | |
| WO | WO 2010/019826 A1 | 2/2010 | |
| WO | WO 2010/039275 A1 | 4/2010 | |
| WO | WO 2011/130495 A1 | 10/2011 | |
| WO | WO 2012/125828 A2 | 9/2012 | |
| WO | WO 2012/135340 A2 | 10/2012 | |
| WO | WO 2013/082440 A2 | 6/2013 | |
| WO | WO 2013/177245 A2 | 11/2013 | |
| WO | WO 2014/005010 A2 | 1/2014 | |
| WO | WO 2014/075067 A1 | 5/2014 | |
| WO | WO 2015/035377 A1 | 3/2015 | |

OTHER PUBLICATIONS

Trevino et al. DNA Microarrays: a Powerful Genomic Tool for Biomedical and Clinical Research. Mol Med 13, 527-541 (2007); doi.org/10.2119/2006-00107.Trevino (Year: 2007).*

Paik et al. A multigene assay to predict recurrence of tamoxifen-treated, node-negative breast cancer. N Engl J Med. Dec. 30, 2004;351(27):2817-26. doi: 10.1056/NEJMoa041588. Epub Dec. 10, 2004. PMID: 15591335; cited as NPL#212 in IDS filed Jan. 16, 2025 (Year: 2004).*

Yang et al. Normalization for cDNA microarray data: a robust composite method addressing single and multiple slide systematic variation. Nucleic Acids Res. Feb. 15, 2002;30(4):e15. doi: 10.1093/nar/30.4.e15. PMID: 11842121; PMCID: PMC100354; cited as NPL#278 in IDS filed Jan. 16, 2025 (Year: 2002).*

Sequencing—Wikipedia,; Archived on Nov. 14 2007 on WaybackMachine (Year: 2007).*

Eisenstein, M. Personalized, sequencing-based immune profiling spurs startups. Nat Biotechnol 31, 184-185 (2013). doi.org/10.1038/nbt0313-184b (Year: 2013).*

Hu et al. The molecular portraits of breast tumors are conserved across microarray platforms. BMC Genomics. Apr. 27, 2006;7:96. doi: 10.1186/1471-2164-7-96. PMID: 16643655; PMCID: PMC1468408; cited as NPL#156 in IDS filed Jan. 16, 2025 (Year: 2006).*

Agilent 1AV2 Microarray (Agilent-012097 Human 1A Microarray (V2) G4110B (Feature Number version); Published on Jan. 2, 2004; NCBI GEO accession: GPL887) (Year: 2004).*

"GeneChip Human Genome U133 Set" Internet Citation, [Online] XP002232760 URL:http//www.affymetrix.com/supporUtechnical/datasheets/hgu133_datashe et.pdf>.

"Human Genome U95Av2", Internet Citation, [Online], Retrieved from the Internet: <URL:http.affymetrix.com>, [retrieved on Oct. 2, 2002].

Akilesh S, et al., "Customized molecular phenotyping by quantitative gene expression and pattern recognition analysis," Genome Res 13:1719-1727 (2003).

Albain et al., "Prognostic and Predictive Value of the 21-Gene Recurrence Score Assay in Postmenopausal Women with Node-Positive, Oestrogen-Receptor-Positive Breast Cancer on Chemotherapy: A Retrospective Analysis of a Randomised Trial." Oncol. (2010); 11: 55-65.

Arriola, E. et al.: "Topoisomerase II alpha amplification may predict benefit from adjuvant anthracyclines in HER2 positive early breast cancer", Breast Cancer Res. Treat., vol. 106, No. 2, (2007), pp. 181-189.

Ayers et al., "Gene Expression Profiles Predict Complete Pathologic Response to Neoadjuvant Paclitaxel and Fluorouracil, Doxorubicin, and Cyclophosphamide Chemotherapy in Breast Cancer." J. Clin. Oncol. 22.12 (2004):2284-2293.

Badve et al., "Basal-like and triple-negative breast cancers: a critical review with an emphasis on the implications for pathologists and oncologists" Modern Pathology, (2011), 24: 157-167.

Bair, E., et al., "Semi-supervised methods to predict patient survival from gene expression data" PLoS Bioi vol. 2, Issue 4, pp. 511-522, (2004).

Baker, "The Central Role of Receiver Operating Characteristic (roc) Curves in Evaluating Tests for the Early Detection of Cancer," J. Natl Cancer Inst. 95(7):511-515 (2003).

Banerjee, et al., "Basal-like breast carcinomas: clinical outcome and response to chemotherapy" J Clin Pathol, (2006), 59(7): 729-735.

Barany, "Genetic Disease Detection and DNA Amplification Using Cloned Thermostable Ligase." PNAS. 88.1(1991): pp. 189-193.

Bastien et al., "PAM50 Breast Cancer Subtyping by RT-qPCR and Concordance with Standard Clinical Molecular Markers," BMC Medical Genomics 5:44, 12 pages (2012).

Beaume, et al., "Orientation and expression of methicillin-resistant Staphylococcus aureus small RNAs by direct multiplexed measurements using the nCounter of NanoString Technology," Journal of Microbiological Methods. (2011). 84:327-334.

Benito, M., et al., "Adjustment of systematic microarray data biases" Bioinformatics 20:105-114 (2004).

Bertucci, et al., "How basal are triple-negative breast cancers?" Int. J. Cancer: (2008) 123, 236-240.

Bertucci, F., et al., "DNA Microarrays for Gene Expression Profiling of Breast Cancer: Principles and Prognostic Applications," Pathologie Biologie, (2006), vol. 54, pp. 49-54, Elsevier (with English Abstract).

Bertucci, F., et al., "Gene expression profiling and clinical outcome in breast cancer," Omics A Journal of Integrative Biology 10(4):429-443 (2006).

Bhatia, P., et al., "Comparison of glyceraldehyde-3-phosphate dehydrogenase and 28S-ribosomal RNA gene expression as RNA loading controls for northern blot analysis of cell lines of varying malignant potential" Anal Biochem 216:223-226 (1994).

Bloom, H., et al., "Histologic grading and prognosis in breast cancer" British Journal of Cancer 9:359-377 (1957).

Brown et al., "Amplification of EMSY, a Novel Oncogene on 11q13, in High Grade Ovarian Surface Epithelial Carcinomas." Gynecol. Oncol. 100.2 (2006):264-270.

Bullinger, L., et al., "Use of gene-expression profiling to identify prognostic subclasses in adult acute myeloid leukemia" N Engl. J Med 350:1605-1616 (2004).

(56)                    References Cited

OTHER PUBLICATIONS

BusinessWire. Retrieved on Feb. 7, 2018 from the Internet: https://www.businesswire.com/news/home/20111208006441/en/Nanostring-Technologies-Announces-Positive-Results-Validation-Study (2011); 2 pages.

Buzdar, A, et al., "Phase II, randomized, double-blind study of two dose levels of arzoxifene in patients with locally advanced or metastatic breast cancer" J Clin Oncol 21:1007-1014 (2003).

Caly, M., et al., "Analysis of correlation between mitotic index, MIB1 score and S-phase fraction as proliferation markers in invasive breast carcinoma. Methodological aspects and prognostic value in a series of 257 cases" Anticancer Res 24:3283-3288 (2004).

Calza et al. (2006), "Intrinsic molecular signature of breast cancer in a population-based cohort of 412 patients", Breast Cancer Res., 8:R34.

Carey et al., "Gene Arrays, Prognosis, and Therapeutic Interventions." Diseases of the Breast. Harris et al., eds. Philadelphia, PA: Lippincott Williams & Wilkins. (2010):458-472.

Chan "Integrating Transcriptomics and Proteomics." Drug Disc. Dev. 6.3(2006):1-6.

Chang H. et al., "Identification of genes associated with chemosensitivity to SAHA/taxane combination treatment in taxane resistant breast cancer cells", Breast Cancer Research and Treatment, 125: 55-63 (2011).

Chaudhuri, P. et al, "SiZer for Exploration of Structures in Curves," Journal of the American Statistical Association 94:807-823, 1999.

Cheang et al. (2006), "Immunohistochemical Detection Using the New Rabbit Monoclonal Antibody SP1 of Estrogen Receptor in Breast Cancer Is Superior to Mouse Monoclonal Antibody 1D5 in Predicting Survival", J Clin Oncol., 24(36):5637-44.

Cheang et al. (2008), "Basal-Like Breast Cancer Defined by Five Biomarkers Has Superior Prognostic Value than Triple-Negative Phenotype", Clin Cancer Res., 14(5):1368-76.

Cheang et al. (2009), "Ki67 Index, HER2 Status, and Prognosis of Patients With Luminal B Breast Cancer", J Natl Cancer Inst., 101 (10):736-50.

Cheang et al., "PAM50 HER2-Enriched Subtype Enriches for Tumor Response to Neoadjuvant Anthracyclines/Taxane and Trastuzumab/Taxane Containing Regimens in HER2-Positive Breast Cancer." Cancer Res. 71. 24S (2011):11Os. (Abstract #S5-2).

Cheang et al: "Gene expression profiling of breast cancer" Annual Review of Pathology: Mechanisms of Disease 2008 US, vol. 3, 2008, pp. 67-97.

Cheang, M. C. U. et al., "Responsiveness of Intrinsic Subtypes to Adjuvant Anthracycline Substitution in the NCIC.CTG MA.5 Randomized Trial," Clinical Cancer Research, vol. 18, No. 8, 20 (2012), pp. 2402-2412.

Chen, et al., "Discordant Protein and mRNA Expression in Lunch Adenocarcinomas." Molecular and Cellular Proteomics 1.4 (2002) p. 304-313.

Cheung et al, "Genetics of Quantitative Variation in Human Gene Expression" in The Genome of *Homo sapiens*, Cold Spring Harbor Symposia Quant Bioi, vol. 68, pp. 403-407 (2003).

Chia et al. (2008), "Human Epidermal Growth Factor Receptor 2 Overexpression As a Prognostic Factor in a Large Tissue Microarray Series of Node-Negative Breast Cancers", J Clin Oncol., 26(35):5697-704.

Chia, S., et al., "Ten-year outcomes in a population-based cohort of node-negative, lymphatic, and vascular invasion-negative early breast cancers without adjuvant systemic therapies" J Clin Oncol 22:1630-1637 (2004).

Clark, G. M., et al., "Mitosin (a new proliferation marker) correlates with clinical outcome in node-negative breast cancer" Cancer Res 57:5505-5508 (1997).

Constantine et al., "Use of genechip high-density oligonucleotide arrays for gene expression monitoring", Life Science News, Amersham Life Science, US, Jan. 1, 1998, pp. 11-14.

Cox and Oakes (1984), "Proportional hazards model", Analysis of Survival Data, Chapman & Hall (London, England), pp. 91-111.

Cronin et al. (2007), "Analytical Validation of the Oncotype OX Genomic Diagnostic Test for Recurrence Prognosis and Therapeutic Response Prediction in Node-Negative, Estrogen Receptor-Positive Breast Cancer", Clin Chem, 53:1084-91.

Cronin, M., et al., "Measurement of gene expression in archival paraffin-embedded tissues: development and performance of a 92-gene reverse transcriptase-polymerase chain reaction assay" Am J Pathol 164:35-42 (2004).

Dabney, A R. "Classification of microarrays to nearest centroids," Bioinformatics 21:4148-54, 2005.

Dalton, L. W., et al., "Histologic grading of breast carcinoma. A reproducibility study" Cancer 73:2765-2770 (1994).

Dhanasekaran, et al., "Delineation of prognostic biomarkers in prostate cancer" Nature 412:822-826 (2001).

Diehn, M., et al., "SOURCE: a unified genomic resource of functional annotations, ontologies, and gene expression data" Nucleic Acids Res 31:219-223 (2003).

Dudoit, S. et al., "A prediction-based resampling method for estimating the number of clusters in a dataset," Genome Bioi 3(7):1-20, 2002.

Ebbert et al., "Characterization of uncertainty in the classification of multivariate assays: application to PAM50 centroid- based genomic predictors for breast cancer treatment plans," Journal of Clinical Bioinformatics (2011); 1(37): 1-9.

Efron, B., et al., "An Introduction to the Bootstrap" Boca Raton, Fla.: CRC Press LLC. pp. 1-16 (1998).

Eggert A, et al., "Relative quantitative RT-PCR protocol for TrkB expression in neuroblastoma using GAPD as an internal control" Biotechniques 28:681-682, 686, 688-691 (2000).

Eisen, M.B. et al., "Cluster analysis and display of genome-wide expression patterns," Proc Natl Acad Sci USA 95:14863-8, 1998.

Elston, C. W., et al., "Pathological prognostic factors in breast cancer. I. The value of histological grade in breast cancer: experience from a large study with long-term follow-up" Histopathology 19:403-410 (1991).

Enard et al, "Intra-and Interspecific Variation in Primate Gene Expression Patterns," Science 296, 340 (2002).

Extended European Search Report issued by the European Patent Office for Application No. 12757489.5 dated Jul. 18, 2014, 10 pages.

Extended European Search Report issued by the European Patent Office for Application No. 13180605.1, dated Oct. 23, 2013, 10 pages.

Fan et al. (2006), "Concordance among Gene-Expression-Based Predictors for Breast Cancer", N. Engl. J. Med., 355:560-69.

Ferree et al., "Abstract LB-327: Analytical performance of the nCounter analysis system for gene expression cancer signatures," American Association for Cancer Research (2011); 71(8): 1-2.

Fisher, B., et al., "A randomized clinical trial evaluating tamoxifen in the treatment of patients with node-negative breast cancer who have estrogen-receptor-positive tumors" N Engl J Med 320:479-484 (1989).

Fisher, E. R., et al., "Correlation of primary breast cancer histopathology and estrogen receptor content" Breast Cancer Res Treat 1:37-41 (1981).

Fitzgibbons, P. L., et al., "Prognostic factors in breast cancer. College of American Pathologists Consensus Statement 1999" Arch Pathol Lab Med 124:966-978 (2000).

Frank, S. G., et al., "Profiling Breast Cancer using Real-Time Quantitative PCR". In Rapid Cycle Real-Time PCR: Methods and Applications Edited by S. Meuer W, C., Nakagawara, K. Heidelberg, Germany, Springer pp. 95-106 (2004).

Frierson, H. F., Jr., et al., "Interobserver reproducibility of the Nottingham modification of the Bloom and Richardson histologic grading scheme for infiltrating ductal carcinoma" Am J Clin Pathol 103:195-198 (1995).

Gaedcke et al., "Predominance of the basal type and HER-2/neu type in brain metastasis from breast cancer," Modern Pathology 20(8): 864-870 (2007).

Geiss, G. K. et al., "Direct Multiplexed Measurement of Gene Expression with Color-Coded Probe Pairs," Nature Biotechnology USA 26(3):317-325, 2008.

GenBank Accession No. AB091343.1, Sep. 22, 2005.

(56)         References Cited

OTHER PUBLICATIONS

GenBank Accession No. AB209631.1, Oct. 17, 2008.
GenBank Accession No. AJ249248.1, Oct. 7, 2008.
GenBank Accession No. AK093306.1, Jul. 3, 2008.
GenBank Accession No. AK095281.1, Jan. 9, 2008.
GenBank Accession No. AK098106.1, Jan. 9, 2008.
8enBank Accession No. AK123010.1, Jul. 3, 2008.
8en8ank Accession No. 8C006428.1, Jul. 15, 2006.
8en8ank Accession No. 8C013732.1, Sep. 12, 2002.
8en8ank Accession No. 8C032677.2, Sep. 16, 2003.
8en8ank Accession No. 8C035498.2, Jul. 15, 2006.
8en8ank Accession No. 8C036503.1, Jul. 17, 2006.
8enBank Accession No. 8C041846.1, Jul. 17, 2006.
8en8ank Accession No. 8C042437.1, Mar. 18, 2009.
8en8ank Accession No. 8E904476.1, Jan. 12, 2011.
8enBank Accession No. 88256659.1, Feb. 13, 2001.
8en8ank Accession No. 88765502.1, May 15, 2001.
GenBank Accession No. BX647539.1, Aug. 3, 2004.
GenBank Accession No. M21389.1, Jun. 11, 1993.
GenBank Accession No. M92424.1, Jan. 13, 1995.
GenBank Accession No. NM_000125.2, Mar. 16, 2008.
GenBank Accession No. NM_000422.1, Aug. 10, 2008.
GenBank Accession No. NM_000424.2, Nov. 17, 2006.
GenBank Accession No. NM_000526.3, Jun. 29, 2008.
GenBank Accession No. NM_000633.2, May 20, 2012.
GenBank Accession No. NM_000662.4, May 10, 2009.
GenBank Accession No. NM_000712.3, Apr. 21, 2012.
GenBank Accession No. NM_000926, May 13, 2012.
GenBank Accession No. NM_001005862.1, May 20, 2012.
GenBank Accession No. NM_001034.1, Oct. 22, 2008.
GenBank Accession No. NM_001040135.1, April1, 2012.
GenBank Accession No. NM_001071.1, Apr. 6, 2008.
GenBank Accession No. NM_001122742.1, May 20, 2012.
GenBank Accession No. NM_001123066.3, Apr. 29, 2012.
GenBank Accession No. NM_001238.1, May 15, 2011.
GenBank Accession No. NM_001254.3, Apr. 29, 2012.
GenBank Accession No. NM_001255.1, Oct. 15, 2006.
GenBank Accession No. NM_001453.1, Apr. 22, 2012.
GenBank Accession No. NM_001793.3, Apr. 29, 2008.
GenBank Accession No. NM_002011.3, Apr. 21, 2012.
GenBank Accession No. NM_002417.2, Apr. 23, 2006.
GenBank Accession No. NM_002467.3, May 17, 2009.
GenBank Accession No. NM_003012.3, Jul. 12, 2009.
GenBank Accession No. NM_004219.2, May 20, 2012.
GenBank Accession No. NM_004323.3, Nov. 18, 2006.
GenBank Accession No. NM_004448.2, May 20, 2012.
GenBank Accession No. NM_004496.2, Apr. 21, 2012.
GenBank Accession No. NM_006101.1, Aug. 10, 2008.
GenBank Accession No. NM_006533.1, Nov. 17, 2006.
GenBank Accession No. NM_006623.2, Oct. 22, 2008.
GenBank Accession No. NM_006845.2, Oct. 22, 2007.
GenBank Accession No. NM_006878.2, Feb. 19, 2009.
GenBank Accession No. NM_007019.2, May 19, 2012.
GenBank Accession No. NM_012319.2, Jun. 3, 2007.
GenBank Accession No. NM_014176.1, Nov. 17, 2006.
GenBank Accession No. NM_014321.2, Oct. 16, 2010.
GenBank Accession No. NM_014373.1, Feb. 11, 2008.
GenBank Accession No. NM_014791.2, Jan. 23, 2012.
GenBank Accession No. NM_016343.3, Jan. 1, 2012.
GenBank Accession No. NM_016463.5, Nov. 17, 2006.
GenBank Accession No. NM_016835.3, Apr. 19, 2010.
GenBank Accession No. NM_018131.3, Feb. 10, 2008.
GenBank Accession No. NM_018685.2, Mar. 25, 2012.
GenBank Accession No. NM_020445.4, Apr. 1, 2012.
GenBank Accession No. NM_024101.4, Oct. 18, 2005.
GenBank Accession No. NM_031423.3, Apr. 29, 2012.
GenBank Accession No. NM_130398.3, Apr. 30, 2012.
GenBank Accession No. NM_138788.3, Mar. 25, 2012.
GenBank Accession No. NM_145697.1, Aug. 20, 2006.

Genestie, C., et al., "Comparison of the prognostic value of Scarff-Bioom-Richardson and Nottingham histological grades in a series of 825 cases of breast cancer: major importance of the mitotic count as a component of both grading systems" Anticancer Res 18:571-576 (1998).
Gennari et al., "HER2 Status and Efficacy of Adjuvant Anthracyclines in Early Breast Cancer: A Pooled Analysis of Randomized Trials," Journal of National Cancer Institute, (2008), 100:14-20.
Gennari, A, "A pooled analysis on the interaction between HER-2 expression and responsiveness of breast cancer to adjuvant chemotherapy," Breast Cancer Res Treat. vol. 100, Suppl 1, (2006) p. S19, 2 pages.
Glas et al. (2006), "Converting a breast cancer microarray signature into a high-throughput diagnostic test", BMC Genomics, 7:278.
Grambsch and Therneau (1994), "Proportional Hazards Tests and Diagnostics Based on Weighted Residuals", Biometrika, 81 (3):515-26.
Greenough, R. B., "Varying degrees of malignancy in cancer of the breast" J Cancer Res 9:453-463 (1925).
Gruvberger, S., et al., "Estrogen receptor status in breast cancer is associated with remarkably distinct gene expression patterns" Cancer Res 61:5979-5984 (2001).
Guatelli et al., "Isothermal, in vitro Amplification of Nucleic Acids by a Multienzyme Reaction Modeled After Retroviral Replication." PNAS. 87.5 (1990):1874-1878.
Hannemann, et al., "Classification of ductal carcinoma in situ by gene expression profiling," Breast Cancer Research. (2006). 8:R61.
Harris et al., Genome-Wide Profiling of Archived Material from CALGB 9840 and 9342 for Paclitaxel (P) and Trastuzumab (T) Response Biomarkers Using Gene Expression and Copy Number Analysis. Cancer Res. 69. 24S (2009). (Poster #4032).
Hastak, et al., "Synergistic Chemosensitivity of Triple-Negative Breast Cancer Cell Lines to Poly(ADP-Ribose) Polymerase Inhibition, Gemcitabine, and Cisplatin" Cancer Res, (2010), 70(20): 7970-7980.
Hatzis et al., "A Genomic Predictor of Response and Survival Following Taxane-Anthracycline Chemotherapy for Invasive Breast Cancer." JAMA. 305.18 (2011):1873-1881.
Hayes et al. (2007), "HER2 and Response to Paclitaxel in Node-Positive Breast Cancer", N Engl J Med., 357(15):1496-506.
Henson, D. E., et al., "Relationship among outcome, stage of disease, and histologic grade for 22,616 cases of breast cancer. The basis for a prognostic index" Cancer 68:2142-2149 (1991).
Herschkowitz, J. I. et al., "Identification of conserved gene expression features between murine mammary carcinoma models and human breast tumors," Genome Bioi 8:R76, 2007.
Hess, K. R. et al., "Pharmacogenomic predictor of sensitivity to preoperative chemotherapy with paclitaxel and fluorouracil, doxorubicin, and cyclophosphamide in breast cancer," J Clin Oncol 24:4236-44, 2006.
Horiguchi et al., "Pathological Complete Response and Prognosis in Patients Receiving Neoadjuvant Paclitaxel and T:rastuzurnab with and without Anthracyclines for Stage II and III, HER2-positive Operable Breast Cancer: A Single-institute Experience," Anticancer Research (2011) 31: 3041-3046.
Horimoto et al., "Low FOXA1 expression predicts good response to neo-adjuvant chemotherapy resulting in good outcomes for luminal HER2-negative breast cancer cases," British Journal of Cancer 112(2):345-351 (2014).
Hoshikawa et al., Hypoxia Induces Different Genes in the Lungs of Rats Compared with Mice, Physiol Genomics (2003) 12:209-219.
Hu Z. et al; "The molecular portraits of breast tumors are conserved across microarray platforms" Bmc Genomics, Biomed Central, vol. 7, No. 1, Apr. 27, 2006, p. 96.
International Preliminary Report on Patentability and Written Opinion issued by the International Searching Authority for PCT Application No. PCT/US2012/030940, dated Oct. 9, 2012, 6 pages.
International Preliminary Report on Patentability and Written Opinion issued by the International Searching Authority for PCT Application No. PCT/US2012/067317, dated Jun. 3, 2014, 8 pages.
International Preliminary Report on Patentability and Written Opinion issued by the International Searching Authority for PCT Application No. PCT/US2013/048551, dated Dec. 31, 2014, 15 pages.

(56) References Cited

OTHER PUBLICATIONS

International Preliminary Report on Patentability and Written Opinion issued by the International Searching Authority for PCT Application No. PCT/US2006/044737, dated Jul. 26, 2007, 7 pages.
International Preliminary Report on Patentability and Written Opinion issued by the International Searching Authority for PCT Application No. PCT/US2009/045820, dated Nov. 30, 2010, 8 pages.
International Preliminary Report on Patentability and Written Opinion issued by the International Searching Authority for PCT Application No. PCT/US2013/042157, dated Dec. 16, 2014, 9 pages.
International Search Report issued by the International Search Authority dated Nov. 25, 2009, in connection with corresponding international patent application No. PCT/US2009/045820.
International Search Report issued by the International Searching Authority for PCT Application No. PCT/US2012/030940, dated Oct. 10, 2012, 5 pages.
International Search Report issued by the International Searching Authority for PCT Application No. PCT/US2012/067317, dated Jul. 12, 2013, 7 pages.
International Search Report issued by the International Searching Authority for Application No. PCT/US2013/048551, dated Mar. 4, 2014, 7 pages.
International Search Report issued by the International Searching Authority for Application No. PCT/US2014/054760, dated Dec. 19, 2014, 5 pages.
International Search Report issued by the International Searching Authority for Application No. PCT PCT/US2006/044737, dated Jul. 26, 2007, 4 pages.
International Search Report issued by the International Searching Authority for Application No. PCT/US2013/042157, dated Dec. 17, 2013, 5 pages.
International Search Report issued by the International Searching Authority for PCT Application No. PCT/US2013/069665, dated Apr. 24, 2014, 6 pages.
International Search Report issued by the International Searching Authority for PCT Application No. PCT/EP2015/078987, dated April4, 2016, 5 pages.
Isakoff. "Triple Negative Breast Cancer: Role of Specific Chemotherapy Agents." Cancer J. 16.1 (2010) :53-61.
Ishida, S., et al., "Role for E2F in control of both DNA replication and mitotic functions as revealed from DNA microarray analysis" Mol Cell Bioi 21:4684-4699 (2001).
Iwahashi, H., et al., "Synergistic anti-apoptotic activity between Bcl-2 and SMN implicated in spinal muscular atrophy" Nature 390:413-417 (1997).
Jorgensen et al., "PAM50 breast cancer intrinsic subtypes and effect of gemcitabine in advanced breast cancer patients." Acta Oncologica (2013) Early Online, 1-12.
Kapp et al.: "Discovery and validation of breast cancer subtypes" BMC Genomics, vol. 7, No. 1, Sep. 11, 2006, p. 231.
Kelly, et al., "Agreement in risk prediction between the 21-gene recurrence score assay (Oncotype OX®) and the PAM50 breast cancer intrinsic Classifier™ in early-stage estrogen receptor-positive breast cancer." The Oncologist. (2012). 17:492-498.
Kollias, J., et al., "The prognosis of small primary breast cancers" Eur J Cancer 35:908-912 (1999).
Koshy et al., "Cisplatin-Gemcitabine Therapy In Metastatic Breast Cancer: Improved Outcome in Triple Negative Breast Cancer Patients Compared to Non-Triple Negative Patients." The Breast, (2010), 19(3):246-248.
Kristt D, et al., "Overexpression of cyclin D1 mRNA in colorectal carcinomas and relationship to clinicopathological features: an in situ hybridization analysis" Pathol Oncol Res 6:65-70 (2000).
Kulkarni, et al., "Digital Multiplexed Gene Expression Analysis Using the NanoString nCounter System," Current Protocols in Molecular Biology. (2011) 25B. 10.1-25B.10-17.
Kwoh et al., "Transcription-Based Amplification System and Detection of Amplified Human Immunodeficiency Virus Type 1 With a Bead-Based Sandwich Hybridization Format." PNAS. 86.4 (1989):1173-1177.

Laping, N. J., et al., "Identification of a novel nuclear guanosine triphosphate-binding protein differentially expressed in renal disease" JAm Soc Nephrol12:883-890 (2001).
Layfield et al., "Assessment of Tissue Estrogen and Progesterone Receptor Levels: A Survey of Current Practice, Techniques, and Quantitation Methods." Breast J. 6 (2000):189-196.
Lee et al., "Prospective Comparison of Clinical and Genomic Multivariate Predictors of Response to Neoadjuvant Chemotherapy in Breast Cancer." Clin. Cancer Res. 16.2 (2010):711-718.
Liedtke et al., "Genomic Grade Index Is Associated With Response to Chemotherapy in Patients With Breast Cancer." J. Clin. Oncol. 27.19 (2009):3185-3191.
Liu, Y et al., "Statistical significance of clustering for high dimension low sample size data," Journal of the American Statistical Association 103(483): 1281-1293, 2008.
Lizardi et al., "Exponential Amplification of Recombinant-RNA Hybridization Probes." Nat. Biotechnol. 6 (1988):1197-1202.
Loi et al. (2007), "Definition of Clinically Distinct Molecular Subtypes in Estrogen Receptor-Positive Breast Carcinomas Through Genomic Grade", J Clin Oncol., 25(10):1239-46.
Makretsov, N. A, et al., "Hierarchical clustering analysis of tissue microarray immunostaining data identifies prognostically significant groups of breast carcinoma" Clin Cancer Res 10:6143-6151 (2004).
Malkov, et al., "Multiplexed measurements of gene signatures in different analytes using the NanoString nCounter™ Assay System," BMC Research Notes. (2009) 2:80.
Manders, P., et al., "The prognostic value of the mitotic activity index in patients with primary breast cancer who were not treated with adjuvant systemic therapy" Breast Cancer Res Treat 77:77-84 (2003).
Martinet al. "PAM50 Proliferation Index Predicts Response to Weekly Adjuvant Paclitaxel in Node-Positive Operable Breast Cancer." Breast Cancer Res. 71. 24S (2011):177s. (Poster #P1-06-04).
Martinet al., "Randomized Phase 3 Trial of Fluorouracil, Epirubicin, and Cyclophosphamide Alone or Followed by Paclitaxel for Early Breast Cancer," J. Natl Cancer Inst. 100(11):805-14 (2008).
Martin, K., et al., "Prognostic Breast Cancer Signature Identified from 3D Culture Model Accurately Predicts Clinical Outcome across Independent Datasets," PLOS ONE vol. 3, No. 8, p. e2994, Abstract (2008).
Medioni et al., "Neoadjuvant Dose-Dense Gemcitabine plus Docetaxel and Vinorelbine plus Epirubicin for Operable Breast Cancer: Improved Prognosis in Triple-Negative Tumors," Drugs R D (2011) 11 (2): 147-157.
Michels, J. J., et al., "Proliferative activity in primary breast carcinomas is a salient prognostic factor" Cancer 100:455-464 (2004).
Michiels et al., "Prediction of Cancer Outcome with Microarrays: A Multiple Random Validation Strategy," Lancet. 365:488-492 (2005).
Miller, C. L., et al., "Methods to optimize the generation of eDNA from postmortem human brain tissue" Brain Res Brain Res Protoe 10:156-167 (2003).
Mischel, P. S., et al., "Molecular analysis of glioblastoma: pathway profiling and its implications for patient therapy" Cancer Bioi Ther 2:242-247 (2003).
Mullins et al.: "Agreement in breast cancer classification between microarray and quantitative reverse transcription PCR from fresh-frozen and formal in-fixed, paraffin-embedded tissues" Clinical Chemistry, vol. 53, No. 7, Jul. 2007, pp. 1273-1279.
NanoString Technologies 2010, "NanoString Exclusively Licenses Worldwide Rights to Intrinsic Subtyping Gene Signature for Breast Cancer," Press Release dated Dec. 6, 2010; 2 pages.
NanoString Technologies 2011, "Data Supporting Utility of the PAM50 Assay for Breast Cancer Gene Expression Profiling to be Presented at ASCO," Press Release dated Jun. 3, 2011; 4 pages.
NanoString Technologies 2011a, "NanoString Embarks on First in Series of Clinical Studies for Breast Cancer Intrinsic Subtyping Assay," Press Release dated Aug. 3, 2011; 2 pages.
NanoString Technologies, "NanoString Initiates Second Clinical Validation Study for Breast Cancer Assay," Press Release dated May 16, 2012: 1 page.

(56)                References Cited

OTHER PUBLICATIONS

Neve, R. M. et al., "A collection of breast cancer cell lines for the study of functionally distinct cancer subtypes," Cancer Cell10:515-27, 2006.
Nielsen et al., "A Comparison of PAM50 Intrinsic Subtyping with Immunohistochemistry and Clinical Prognostic Factors in Tamoxifen-Treated Estrogen Receptor-Positive Breast Cancer." Clin. Cancer Res. 16.21(2010):5222-5232.
Nielsen et al., "Gemcitabine Plus Docetaxel Versus Docetaxel in Patients With Predominantly Human Epidermal Growth Factor Receptor 2-Negative Locally Advanced or Metastatic Breast Cancer: A Randomized, Phase III Study by the Danish Breast Cancer Cooperative Group" J. of Clinical Oncology, vol. 29, No. 36 (2011) pp. 4748-4754.
Nielsen, T. 0., et al., "Immunohistochemical and clinical character-ization of the basal-like subtype of invasive breast carcinoma" Clin Cancer Res 10:5367-5374 (2004).
Oh et al. (2006), "Estrogen-Regulated Genes Predict Survival in Hormone Receptor-Positive Breast Cancers", J Clin Oncol., 24(11):1656-64.
Olivotto et al. (2005), "Population-Based Validation of the Prognostic Model ADJUVANT! for Early Breast Cancer", J Clin Oncol, 23:2716-25.
Paik et al.: "A Mutigene Assay to Predict Recurrence of Tamoxifen-treated Node-Negative Breast Cancer" N Engl J Med., vol. 351, No. 27, Dec. 30, 2004, pp. 2817-2826.
Paik, S. et al., "Gene expression and benefit of chemotherapy in women with node-negative, estrogen receptor-positive breast cancer," J Clin Oncol 24:3726-34, 2006.
Panaro, N.J., et al., "Evaluation of DNA fragment sizing and quantification by the Agilent 2100 Bioanalyzer" Clin Chem 46:1851-1853 (2000).
Parker et al., "Breast Cancer Molecular Subtypes Predict Response to Anthracycline/Taxane-Based Chemotherapy," J. Cancer Research, (2009), 69:Supp 3; abstract 2019.
Parker et al., "Breast cancer molecular subtypes predict response to anthracycline/taxane-based chemotherapy," Poster at 2009 San Anto-nio Breast Cancer Symposium, #2019 (2009).
Parker et al: "Supervised risk predictor of breast cancer based on intrinsic subtypes." J Clin Oncol, Mar. 10, 2009, vol. 27, No. 8, Mar. 10, 2009 (Mar. 10, 2009) pp. 1160-1167.
Perou et al.: "Molecular portraits of human breast tumours" Nature, vol. 406, No. 6797, Aug. 17, 2000, pp. 747-752.
Perou, C. M., et al., "Distinctive gene expression patterns in human mammary epithelial cells and breast cancers" PNAS 96:9212-9217 (1999).
Perou, C. M., et al., "Tumor classification using gene expression patterns from DNA microarrays" New Technologies for life sci-ences: A Trends Guide pp. 67-76 (2000).
Perreard et al: "Classification and risk stratification of invasive breast carcinomas using a real-time quantitative RT-PCR assay" Breast Cancer Research, Current Science, vol. 8, np. 2, Apr. 20, 2006, p. R23.
Pollack, J. R., et al., "Genome-wide analysis of DNA copy-number changes using eDNA microarrays" Nature Genetics 23:41-46 (1999).
Pollack, J. R., et al., "Microarray analysis reveals a major direct role of DNA copy number alteration in the transcriptional program of human breast tumors" PNAS 99:12963-12968 (2002).
Prat et al., "Deconstructing the molecular portraits of breast cancer." Molecular Oncology. vol. 5, pp. 5-23 (2011).
Prat, A, et al., "PAM50 assay and the three-gene model for identi-fying the major and clinically relevant molecular subtypes of breast cancer". Breast Cancer Research and Treatment 135(1):301-306 (2012).
Prat, et al., "Phenotypic and molecular characterization of the claudin-low intrinsic subtype of breast cancer," Breast Cancer Research. (2010). 12:R68.
Pritchard et al., "HER2 and Responsiveness of Breast Cancer to Adjuvant Chemotherapy," New England J Medicine, (2006), 354:2103-2111.

Quackenbush. "Microarray Data Normalization and Transforma-tion." Nat. Genet. 32 (2002):496-501.
Rakha, E. et al., "Are triple-negative and basal-like breast cancer synonymous?" Clin Cancer Res 14(2):618, 2008.
Rasmussen, R., "Quantification on the LightCycler." in Rapid Cycle Real-Time PCR: Methods and Applications Edited by Mever et al, Springer Verlag, pp. 21-34 (2001).
Redana et al., "Trastuzumab with either docetaxel or vinorelbine as first-line treatment for patients with HER2-positive advanced breast cancer: a retrospective comparison," BMC Cancer (2010) 10(28): 1-9.
Robbins, P., et al., "Histological grading of breast carcinomas: a study of interobserver agreement" Hum Pathol26:873-879 (1995).
Rodriguez et al., "Molecular Profiling of Chronic Lymphocitic Leukemia. Comparison of e-DNA and OliQo Microarray Plat-forms." Report of CNIO MeetinQ Microarrays 2004:, paQe 15 (2004).
Rodriguez-Lescure et al., "PAM50 Proliferation Index Predicts Response to Weekly Adjuvant Paclitaxel in Node-Positive Operable Breast Cancer." Breast Cancer Res. 71. 24S (2011):177s. (Poster #P1-06-04).
Ross et al. (2008), "Chemosensitivity and Stratification by a Five Monoclonal Antibody Immunohistochemistry Test in the NSABPB14 and B20Trials", Clin Cancer Res., 14(20):6602-9.
Ross, D. T., et al., "Systematic variation in gene expression patterns in human cancer cell lines" Nat Genet 24:227-235 (2000).
Ross, J.S. et al., "The Her-2/neu gene and protein in breast cancer 2003: biomarker and target of therapy." Oncologist. 8(4):307-25, 2003.
Roux, S., et al., "Effects of prostaglandins on human hematopoietic osteoclast precursors" Endocrinology 138:1476-1482 (1997).
Rouzier et al. (2005), "Breast Cancer Molecular Subtypes Respond Differently to Preoperative Chemotherapy", Clin Cancer Res., 11 (16):5678-85.
Rouzier, R. et al., "Nomograms to predict pathologic complete response and metastasis-free survival after preoperative chemo-therapy for breast cancer," J Clin Oncol23:8331-9, 2005.
Santalucia, J., "A unified view of polymer, dumbbell, and oligo-nucleotide DNA nearest-neighbor thermodynamics." PNAS 95:1460-1465 (1998).
Schena et al., "Quantitative Monitoring of Gene Expression Patterns with a Complementary DNA Microarray." Science. 270.5235 (1995):467-470.
Schwanhausser, et al., "Global quantification of mammalian gene expression control." Nature. (2011). 473:337-342.
Schwarz, G. "Estimating the dimension of a model" The Annals of Statistics 6:461-464 (1978).
Sheather, S. J. et al., "A Reliable Data-Based Bandwidth Selection Method for Kernel Density Estimation," Journal of the Royal Statistical Society 53:683-690, 1991.
Singletary, S. E., et al., "Staging system for breast cancer revisions for the 6th edition of the AJCC Cancer Staging Manual." Surg Clin North Am 83:803-819 (2003).
Slonim, "From Patterns to Pathways: Gene Expression Data Analy-sis Comes of Age." Nat. Genet. Suppl. 32 (2002):502-508.
Sorlie et al. (2003), "Repeated observation of breast tumor subtypes in independent gene expression data sets", PNAS, 100(14):8418-23.
Sorlie et al.: "Gene expression patterns of breast carcinomas dis-tinguish tumor subclasses with clinical implications" PNAS, vol. 98, No. 19, Sep. 11, 2001, pp. 10869-10874.
Sotiriou et al., "Gene Expression Profiling in Breast Cancer: Under-standing the Molecular Basis of Histologic Grade To Improve Prognosis", J Natl Cancer Inst, 98:262-272 (2006).
Sotiriou, C., et al., "Breast cancer classification and prognosis based on gene expression profiles from a population-based study" PNAS 100:10393-10398 (2003).
Spanakis, E., "Problems related to the interpretation of autoradiographic data on gene expression using common constitutive transcripts as controls" Nucleic Acids Res 21:3809-3819 (1993).
Spruance et al., "Hazard Ratio in Clinical Trials." Antimicrob. Agents Chemother. 48.8 (2004):2787-2792.

(56) References Cited

OTHER PUBLICATIONS

Storey, J. D. et al., "Statistical methods for identifying differentially expressed genes in DNA microarrays," Methods Mol Biol224:149-57, 2003.

Supplementary European Search Report issued for EP12854489 and completed on Jun. 17, 2015.

Suzuki, T., "Control selection for RNA quantitation" Biotechniques 29:332-337 (2000).

Szabo, A, et al., "Statistical modeling for selecting housekeeper genes" Genome Bioi 5:R59 (2004).

Taylor-Papadimitriou, J., et al., "Keratin expression in human mammary epithelial cells cultured from normal and malignant tissue: relation to in vivo phenotypes and influence of medium" J Cell Sci 94:403-113 (1989).

Thisted, "What is a P-Value?" Unpublished manuscript, University of Chicago, Chicago, IL. pp. 1-6 (1998).

Thuerigen et al., "Gene Expression Signature Predicting Pathologic Complete Response with Gemcitabine, Epirubicin, and Docetaxel in Primary Breast Cancer." J. Clin. Oncol., (2006), 24(12): 1839-1845.

Tibshirani et al: "Diagnosis of multiple cancer types by shrunken centroids of gene expression" PNAS, vol. 99, No. 10, May 14, 2002, pp. 6567-6572.

Troyanskaya, 0., et al., Missing value estimation methods for DNA microarrays Bioinformatics 17:520-525 (2001).

Truong et al. (2005), The Prognostic Significance of the Percentage of Positive/Dissected Axillary Lymph Nodes in Breast Cancer Recurrence and Survival in Patients with One to Three Positive Axillary Lymph Nodes, Cancer, 103(10):2006-14.

Tubbs, R. R., et al., "Discrepancies in clinical laboratory testing of eligibility for trastuzumab therapy: apparent immunohistochemical false-positives do not get the message" J Clin Oncol19:2714-2721 (2001).

Van De Vijver, M. J. et al., "A gene-expression signature as a predictor of survival in breast cancer," N Engl J Med 347:1999-2009, 2002.

Van't Veer et al. (2005), "Gene Expression Profiling of Breast Cancer: A New Tumor Marker", J Clin Oncol. 23(8):1631-5.

Van't Veer et al: "Gene expression profiling predicts clinical outcome of breast cancer" Nature, vol. 415, No. 6871 Jan. 31, 2002 (Jan. 31, 2002), pp. 530-536.

Vandesompele J., et al., "Accurate normalization of real-time quantitative RT-PCR data by geometric averaging of multiple internal control genes" Genome Bioi 3: Research 0034 (2002).

Weigelt et al., "Breast cancer molecular profiling with single sample predictors: a retrospective analysis", Lancet Oncol. 11: 339-49 (2010).

Weis et al., "Detection of Rare mRNAs via Quantitative RT-PCR." Trends in Genet. 8.8 (1992):263-264.

Welsh, J. B., et al., "Analysis of gene expression profiles in normal and neoplastic ovarian tissue samples identifies candidate molecular markers of epithelial ovarian cancer" PNAS 98:1176-1181 (2001).

West, M., et al., "Predicting the clinical status of human breast cancer by using gene expression profiles" PNAS '98:11462-11467 (2001).

Whitfield, M. L., et al., "Identification of genes periodically expressed in the human cell cycle and their expression in tumors" Mol Bioi Cell 13:1977-2000 (2002).

Wittwer, C.T., et al., "Real-time PCR". In Molecular Microbiology: Diagnostic Principles and Procedures, PersinQ et al., editors. WashinQton, D.C.: ASM Press (2004).

Wolff et al., "American Society of Clinical Oncology/College of American Pathologists Guideline Recommendations for Human Epidermal Growth Factor Receptor 2 Testing in Breast Cancer." Arch. Pathol. Lab. Med. 131 (2007):18-43.

Written Opinion issued by the International Searching Authority for Application No. PCT/US2014/054760, dated Dec. 19, 2014, 7 pages.

Wu et al., "Response and Prognosis of Taxanes and Anthracyclines Neoadjuvant Chemotherapy in Patients with Triple-Negative Breast Cancer." J. Cancer Res. Clin. Oncol. 137.10 (2011):1505-1510.

Yang, Y. H., et al., "Normalization for eDNA microarray data: a robust composite method addressing single and multiple slide systematic variation" Nucleic Acids Res 30:e15 (2002).

Dixon et al. (2002) "Neoadjuvant endocrine therapy of breast cancer: a surgical perspective". *Eur J Cancer.* 38( 17), pp. 2214-2221.

* cited by examiner

FIG. 1A                    FIG. 1B
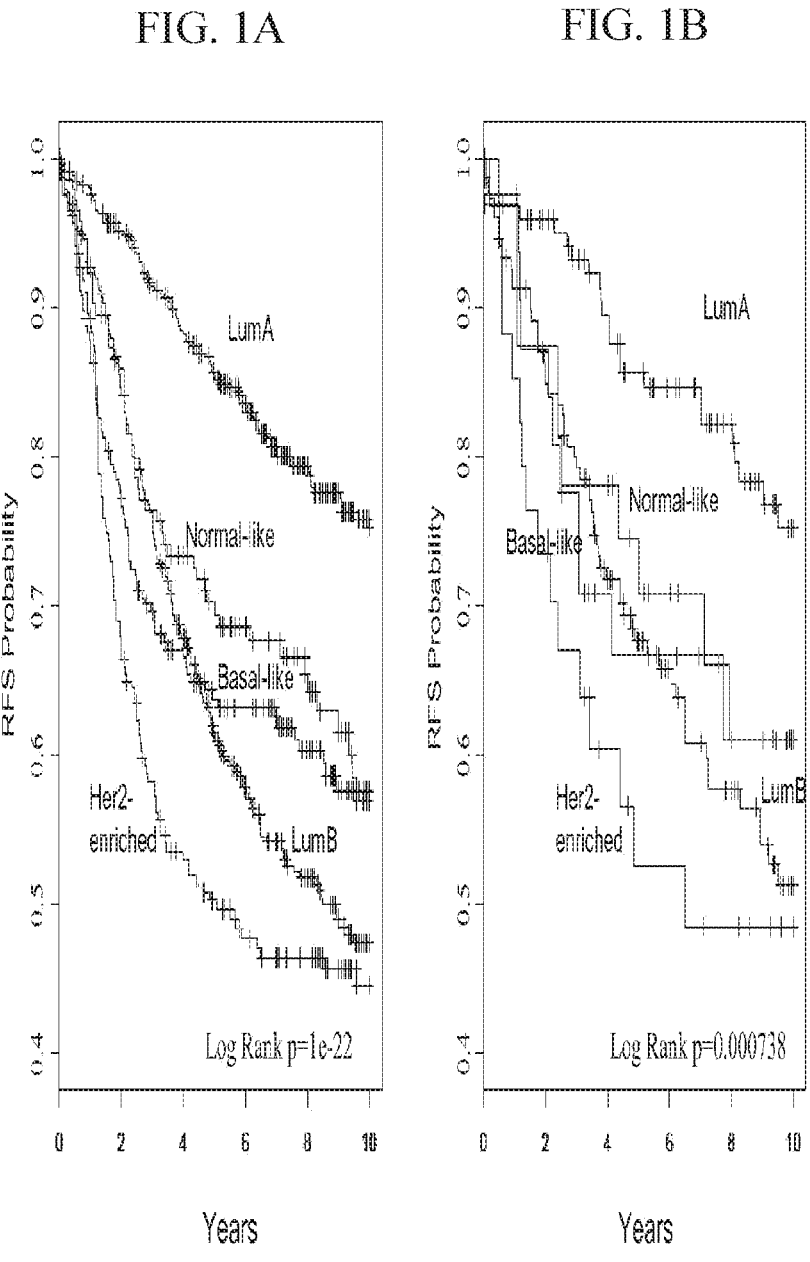
Years                      Years

Node-negative, no adjuvant systemic

FIG. 5A                                                        FIG. 5B
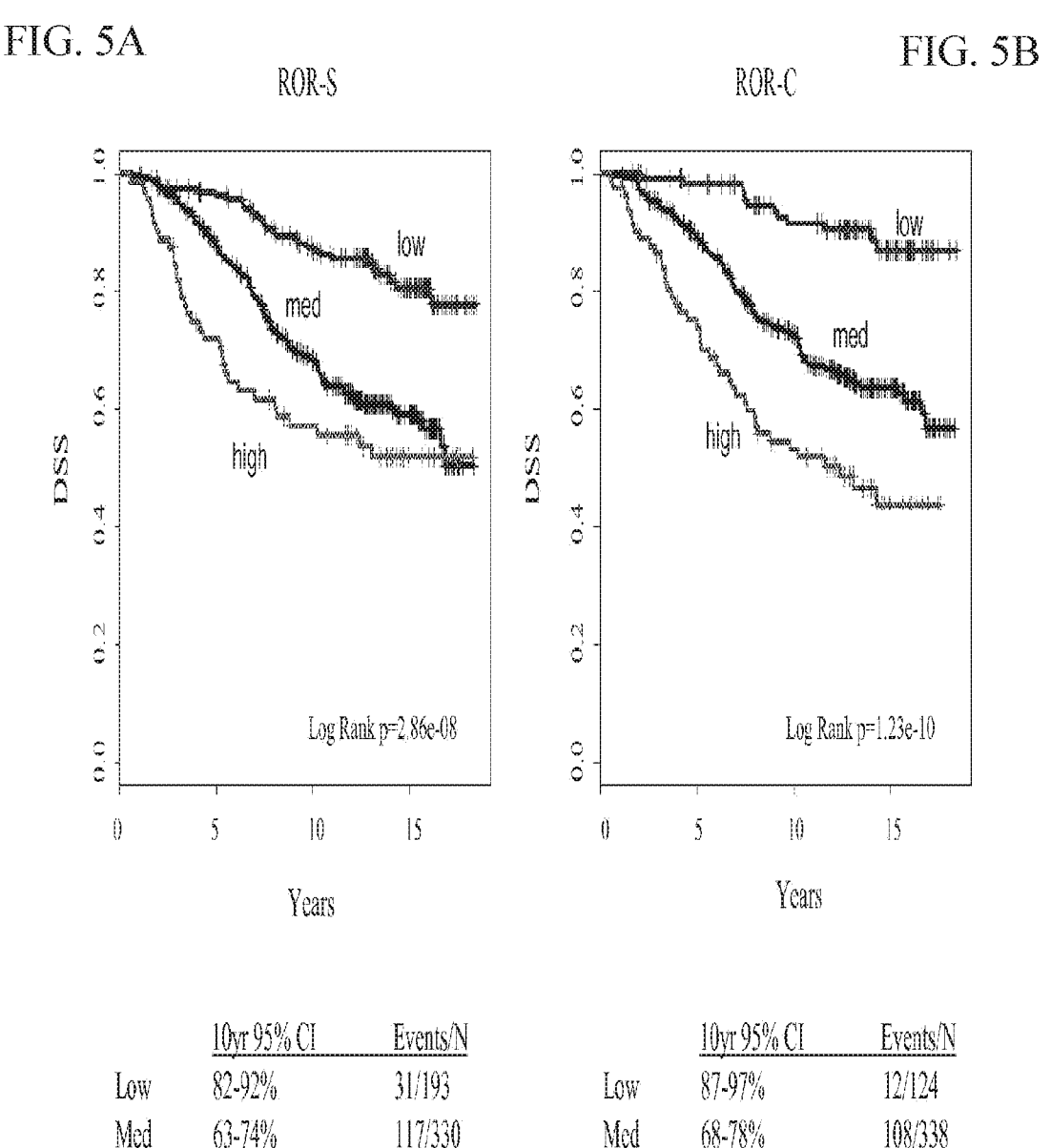
| | 10yr 95% CI | Events/N | | 10yr 95% CI | Events/N |
|---|---|---|---|---|---|
| Low | 82-92% | 31/193 | Low | 87-97% | 12/124 |
| Med | 63-74% | 117/330 | Med | 68-78% | 108/338 |
| High | 45-69% | 33/72 | High | 43-65% | 42/83 |

FIG. 6A                                                          FIG. 6B
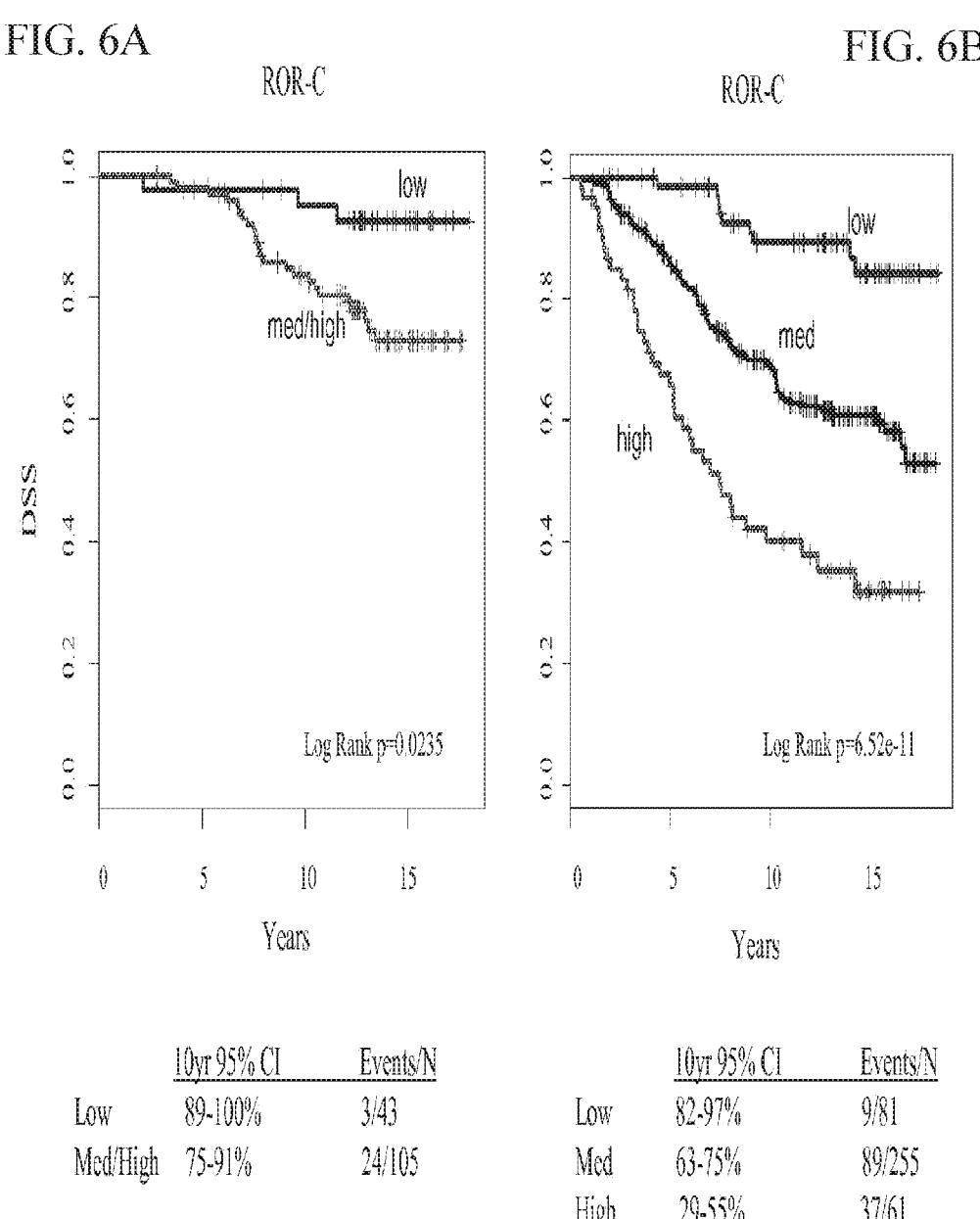
|  | 10yr 95% CI | Events/N |
|---|---|---|
| Low | 89-100% | 3/43 |
| Med/High | 75-91% | 24/105 |
|  | 10yr 95% CI | Events/N |
|---|---|---|
| Low | 82-97% | 9/81 |
| Med | 63-75% | 89/255 |
| High | 29-55% | 37/61 |

| | 10yr 95% CI | Events/N | | | 10yr 95% CI | Events/N |
|---|---|---|---|---|---|---|
| Low/N- | 89-100% | 3/43 | | Med/N- | 73-91% | 19/83 |
| Low/N+ | 82-97% | 9/80 | | Med/N+ | 64-76% | 84/245 |

FIG. 7C                                                           FIG. 7D
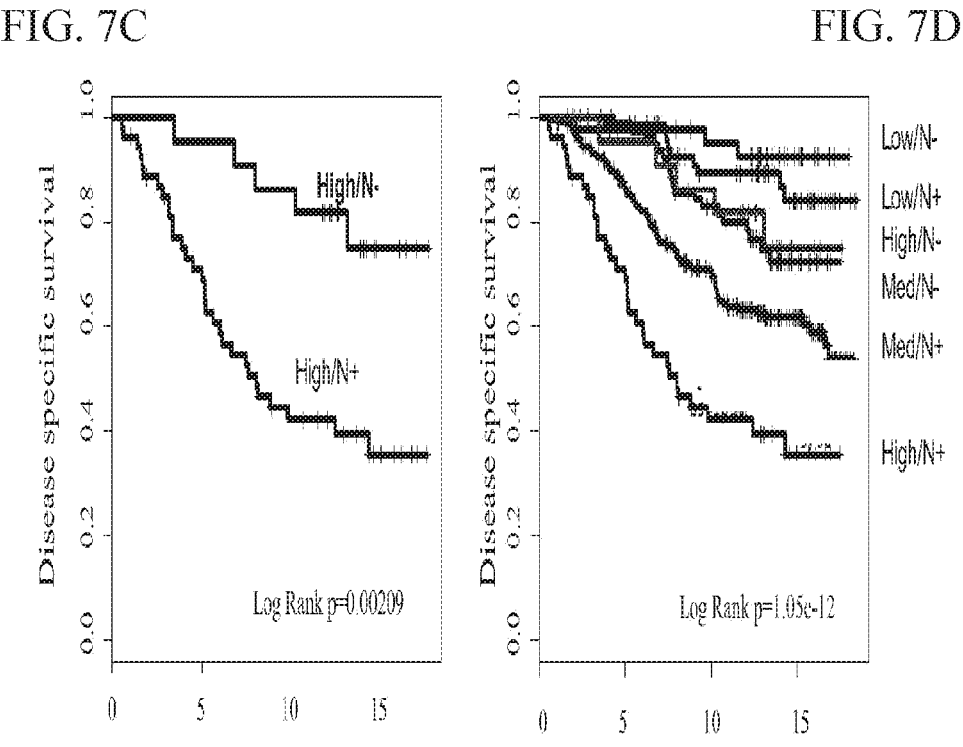
| | 10yr 95% CI | Events/N |
|---|---|---|
| High/N- | 67-100% | 5/22 |
| High/N+ | 31-59% | 31/54 |
| | 10yr 95% CI | Events/N |
|---|---|---|
| Low/N- | 89-100% | 3/43 |
| Low/N+ | 82-97% | 9/80 |
| Med/N- | 73-91% | 19/83 |
| Med/N+ | 64-76% | 84/245 |
| High/N- | 67-100% | 5/22 |
| High/N+ | 31-59% | 31/54 |

METHODS FOR ASSAYING ENRICHED NUCLEIC ACIDS

CROSS-REFERENCE TO RELATED APPLICATIONS

This application is a continuation of U.S. patent application Ser. No. 18/158,396, filed Jan. 23, 2023, which claims the benefit of application Ser. No. 16/656,984, filed Oct. 18, 2019, now abandoned, which claims the benefit of U.S. patent application Ser. No. 14/931,594, filed Nov. 3, 2015, now abandoned, which claims the benefit of U.S. patent application Ser. No. 12/995,450, filed Feb. 22, 2011, now U.S. Pat. No. 9,631,239, issued Apr. 25, 2017, which claims the benefit of International Application No. PCT/US2009/045820, filed Jun. 1, 2009, which claims priority under 35 U.S.C. § 119 to U.S. Provisional Application Ser. No. 61/057,508, filed May 30, 2008. The contents of the applications are incorporated herein by reference in their entireties.

GOVERNMENT INTEREST

This invention was made with government support under grant numbers CA058223, CA095614, CA097769, and CA114722 awarded by The National Institutes of Health. The government has certain rights in the invention.

SEQUENCE LISTING

A Sequence Listing is provided herewith as a Sequence Listing XML, "VERA-2-5_Sequence_Listing" created on Oct. 2, 2024, and having a size of 127,612 bytes. The contents of the Sequence Listing XML are incorporated herein by reference in their entirety.

FIELD OF THE INVENTION

The present invention relates to methods for classifying breast cancer specimens into subtypes and for evaluating prognosis and response to therapy for patients afflicted with breast cancer.

BACKGROUND OF THE INVENTION

Breast cancer is the second most common cancer among women in the United States, second only to skin cancer. A woman in the U.S. has a one in eight chance of developing breast cancer during her lifetime, and the American Cancer Society estimates that more than 178,480 new cases of invasive breast cancer will be reported in the U.S. in 2007. Breast cancer is the second leading cause of cancer deaths in women, with more than 40,000 deaths annually.

Improved detection methods, mass screening, and advances in treatment over the last decade have significantly improved the outlook for women diagnosed with breast cancer. Today, approximately 80% of breast cancer cases are diagnosed in the early stages of the disease when survival rates are at their highest. As a result, about 85% percent of breast cancer patients are alive at least five years after diagnosis. Despite these advances, approximately 20% of women diagnosed with early-stage breast cancer have a poor ten-year outcome and will suffer disease recurrence, metastasis or death within this time period.

Significant research has focused on identifying methods and factors for assessing breast cancer prognosis and predicting therapeutic response (See generally, Ross and Hortobagyi, eds. (2005) Molecular Oncology of Breast Cancer (Jones and Bartlett Publishers, Boston, Mass.) and the references cited therein). Prognostic indicators include conventional factors, such as tumor size, nodal status and histological grade, as well as molecular markers that provide some information regarding prognosis and likely response to particular treatments. For example, determination of estrogen (ER) and progesterone (PgR) steroid hormone receptor status has become a routine procedure in assessment of breast cancer patients. See, for example, Fitzgibbons et al., Arch. Pathol. Lab. Med. 124:966-78, 2000. Tumors that are hormone receptor positive are more likely to respond to hormone therapy and also typically grow less aggressively, thereby resulting in a better prognosis for patients with ER+/PgR+ tumors. Overexpression of human epidermal growth factor receptor 2 (HER-2/neu), a transmembrane tyrosine kinase receptor protein, has been correlated with poor breast cancer prognosis (see, e.g., Ross et al., The Oncologist 8:307-25, 2003), and HER-2 expression levels in breast tumors are used to predict response to the anti-HER-2 monoclonal antibody therapeutic trastuzumab (Herceptin®, Genentech, South San Francisco, Calif.).

SUMMARY OF THE INVENTION

Methods for classifying and for evaluating prognosis and treatment of a subject with breast cancer are provided. The methods include prediction of breast cancer subtype using a supervised algorithm trained to stratify subjects on the basis of breast cancer intrinsic subtype. The prediction model is based on the gene expression profile of the intrinsic genes listed in Table 1. In some embodiments, the algorithm is a nearest centroid algorithm, similar to the Prediction Analysis of Microarray (PAM) algorithm. The algorithm can be trained based on data obtained from the gene expression profiles deposited as accession number GSE10886 in the National Center for Biotechnology Information Gene Expression Omnibus. This prediction model, herein referred to as the PAM50 classification model, can be used to accurately predict the intrinsic subtype of a subject diagnosed with or suspected of having breast cancer.

Further provided are compositions and methods for predicting outcome or response to therapy of a subject diagnosed with or suspected of having breast cancer. These methods are useful for guiding or determining treatment options for a subject afflicted with breast cancer. Methods of the invention further include means for evaluating gene expression profiles, including microarrays and quantitative polymerase chain reaction assays, as well as kits comprising reagents for practicing the methods of the invention.

BRIEF DESCRIPTION OF THE DRAWINGS

FIGS. 1A to 1C shows outcomes based on subtype predictions using the PAM50 classifier. The PAM50 classification for LumA, LumB, HER2-enriched, Basal-like, and Normal-like shows prognostic significance for 1451 patients across all 5 test sets combined (FIG. 1A), in 376 patients given endocrine therapy alone (FIG. 1B), and in 701 node negative patients given no adjuvant systemic therapy (FIG. 1C).

(FIG. 2A) risk of relapse scores plotted for each breast cancer subtype: low risk scores $<-0.1$, moderate risk scores between $-0.1$ and $0.2$, and high risk scores $\geq 0.2$. (FIG. 2B) Kaplan-Meier plots and significance of the risk score for all 1286 test samples, (FIG. 2C) 376 patients that received adjuvant endocrine therapy only, and (FIG. 2D) 560 patients that were node-negative and received no adjuvant systemic therapy.

FIGS. 4A and 4B shows association of PAM50 intrinsic subtype, determined by qPCR from paraffin blocks, with (FIG. 4A) relapse free survival and (FIG. 4B) disease-specific survival among 702 women with invasive breast carcinoma treated with adjuvant tamoxifen.

FIGS. 5A and 5B shows Kaplan-Meier analysis of breast cancer disease-specific survival for patients stratified into low, medium and high risk categories by applying the Risk-Of-Relapse algorithm to qPCR data generated from paraffin blocks. (FIG. 5A) ROR-S, (FIG. 5B) ROR-C.

FIGS. 6A and 6B shows Kaplan-Meier analysis of breast cancer disease-specific survival for patients stratified into low, medium and high risk categories (as defined previously on independent material by applying the ROR-C algorithm to women with (FIG. 6A) node negative disease, and (FIG. 6B) node positive disease).

FIGS. 7A to 7D shows Kaplan-Meier analysis of breast cancer disease-specific survival for patients stratified into node negative or node positive categories among women with a low risk ROR-C (FIG. 7A), women with moderate risk ROR-C (FIG. 7B); women with high risk ROR-C (FIG. 7C). For direct comparison, all curves are superimposed in the lower right panel. Among women with low ROR-C, there is no significant difference in outcome by nodal status (FIG. 7D).

(FIG. 10B) the Adjuvant Predicted BCSS 70-80%, ROR-S Low vs. Med/High; and, (FIG. 10C) Adjuvant Predicted BCSS <70%, ROR-S Low vs. Med/High.

DETAILED DESCRIPTION OF THE INVENTION

Overview

Figure 1C:
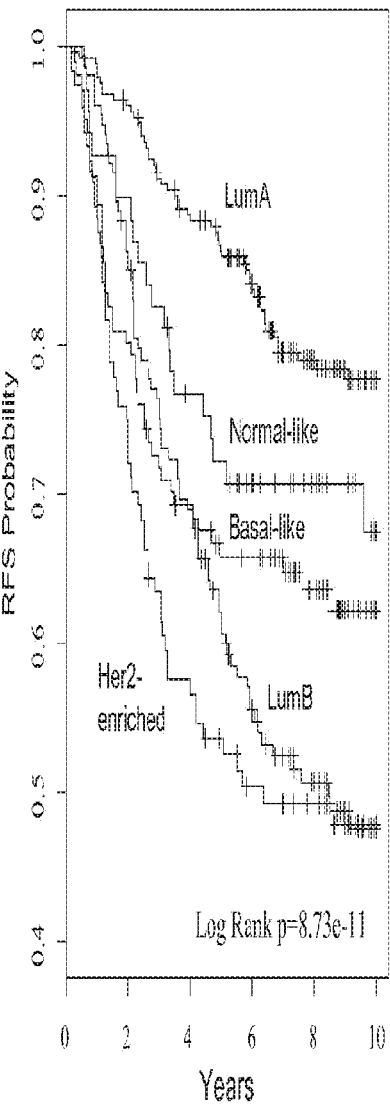
Figures 2A, 2B, 2C, 2D:
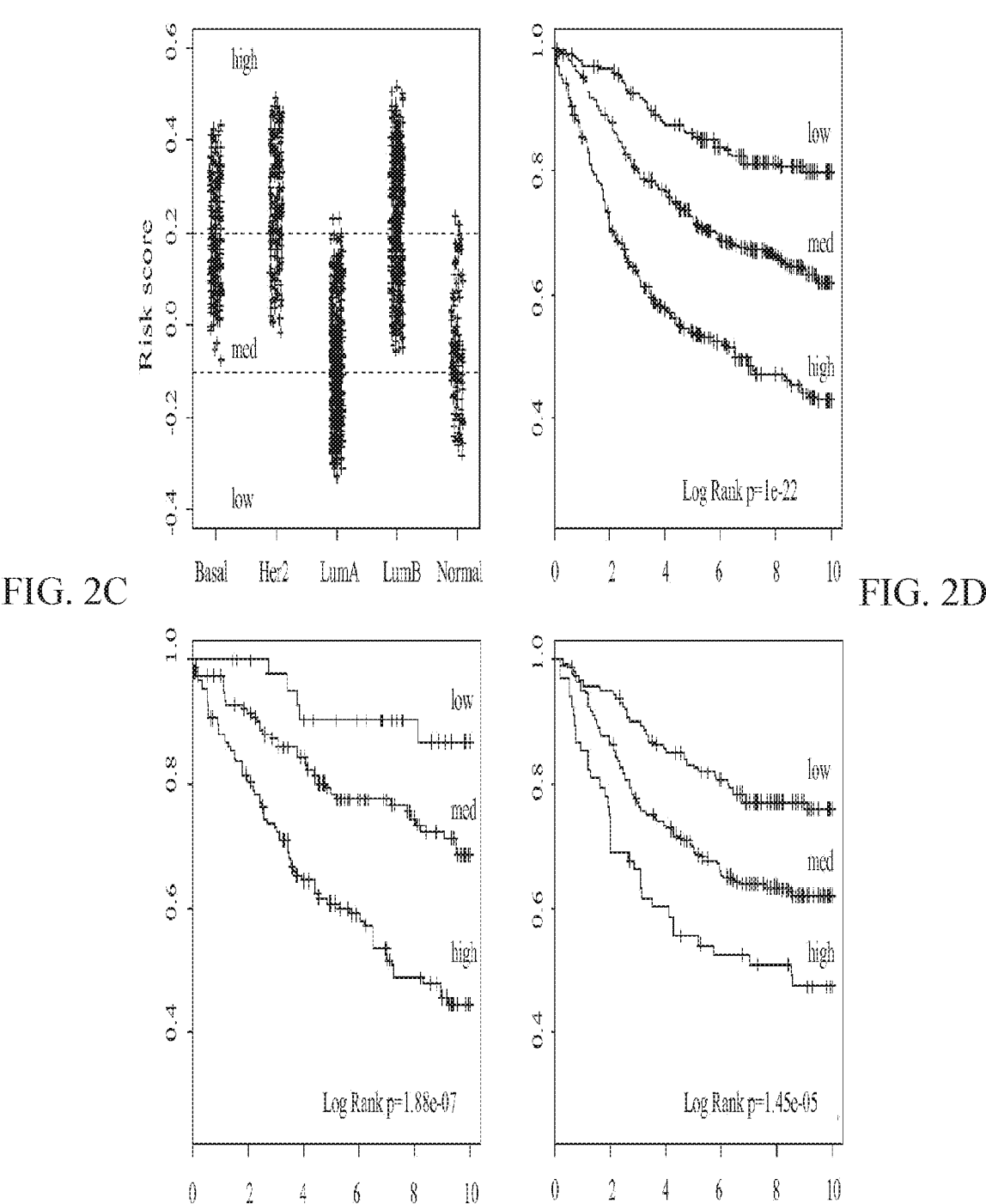
FIGS. 2A to 2D shows risk classification for test cases using a full model of intrinsic subtypes and two clinical variables.

Despite recent advances, the challenge of cancer treatment remains to target specific treatment regimens to distinct tumor types with different pathogenesis, and ultimately personalize tumor treatment in order to maximize outcome. In particular, once a patient is diagnosed with cancer, such as breast cancer, there is a need for methods that allow the physician to predict the expected course of disease, including the likelihood of cancer recurrence, long-term survival of the patient and the like, and select the most appropriate treatment options accordingly.

For the purposes of the present invention, "breast cancer" includes, for example, those conditions classified by biopsy or histology as malignant pathology. The clinical delineation of breast cancer diagnoses is well-known in the medical arts. One of skill in the art will appreciate that breast cancer refers to any malignancy of the breast tissue, including, for example, carcinomas and sarcomas. Particular embodiments of breast cancer include ductal carcinoma in situ (DCIS), lobular carcinoma in situ (LCIS), or mucinous carcinoma. Breast cancer also refers to infiltrating ductal (IDC) or infiltrating lobular carcinoma (ILC). In most embodiments of the invention, the subject of interest is a human patient suspected of or actually diagnosed with breast cancer.

Breast cancer is a heterogeneous disease with respect to molecular alterations and cellular composition. This diversity creates a challenge for researchers trying to develop classifications that are clinically meaningful. Gene expression profiling by microarray has provided insight into the complexity of breast tumors and can be used to provide prognostic information beyond standard pathologic parameters (1-7).

Expression profiling of breast cancer identifies biologically and clinically distinct molecular subtypes which may require different treatment approaches [van't Veer 2005][Loi 2007][Cheang 2008a]. The major intrinsic subtypes of breast cancer referred to as Luminal A, Luminal B, HER2-enriched, Basal-like have distinct clinical features, relapse risk and response to treatment [Sorlie 2003]. The "intrinsic" subtypes known as Luminal A (LumA), Luminal B (LumB), HER2-enriched, Basal-like, and Normal-like were discovered using unsupervised hierarchical clustering of microarray data (1, 8). Intrinsic genes, as described in Perou et al. (2000) Nature 406:747-752, are statistically selected to have low variation in expression between biological sample replicates from the same individual and high variation in expression across samples from different individuals. Thus, intrinsic genes are the classifier genes for breast cancer classification. Although clinical information was not used to derive the breast cancer intrinsic subtypes, this classification has proved to have prognostic significance (1, 6, 9, 10).

Breast tumors of the "Luminal" subtype are ER positive and have a similar keratin expression profile as the epithelial cells lining the lumen of the breast ducts (Taylor-Papadimitriou et al. (1989) J Cell Sci 94:403-413; Perou et al (2000) New Technologies for Life Sciences: A Trends Guide 67-76, each of which is herein incorporated by reference in its entirety). Conversely, ER-negative tumors can be broken into two main subtypes, namely those that overexpress (and are DNA amplified for) HER-2 and GRB7 (HER-2-enriched) and "Basal-like" tumors that have an expression profile similar to basal epithelium and express Keratin 5, 6B, and 17. Both these tumor subtypes are aggressive and typically more deadly than Luminal tumors; however, there are subtypes of Luminal tumors with different outcomes. The Luminal tumors with poor outcomes consistently share the histopathological feature of being higher grade and the molecular feature of highly expressing proliferation genes.

The translation of the intrinsic subtypes into a clinical assay has been challenging because unsupervised clustering is better suited to organizing large numbers of samples and genes than classifying individual samples using small gene sets.

Thus, provided herein are improved methods and compositions for classifying breast cancer intrinsic subtypes. The methods utilize a supervised algorithm to classify subject samples according to breast cancer intrinsic subtype. This algorithm, referred to herein as the PAM50 classification model, is based on the gene expression profile of a defined subset of intrinsic genes that has been identified herein as superior for classifying breast cancer intrinsic subtypes, and for predicting risk of relapse and/or response to therapy in a subject diagnosed with breast cancer. The subset of genes, along with primers specific for their detection, is provided in Table 1.

In some embodiments, at least about 40 of the genes listed in Table 1 are used in the PAM50 classification model. In other embodiments, at least 41, at least 43, at least 44, at least 45, at least 46, at least 47, at least 48, at least 49, or all 50 of the intrinsic genes listed in Table 1 are used in the model. The methods disclosed herein are not intended for use with one or only a few of the genes listed in Table 1. In fact, it is the combination of substantially all of the intrinsic genes that allows for the most accurate classification of intrinsic subtype and prognostication of outcome or therapeutic response to treatment. Thus, in various embodiments, the methods disclosed herein encompass obtaining the genetic profile of substantially all the genes listed in Table 1. "Substantially all" may encompass at least 47, at least 48, at least 49, or all 50 of the genes listed in Table 1. Unless otherwise specified, "substantially all" refers to at least 49 of the genes listed in Table 1. It will also be understood by one of skill in the art that one subset of the genes listed in Table 1 can be used to train an algorithm to predict breast cancer subtype or outcome, and another subset of the genes used to characterize an individual subject. Preferably, all 50 genes are used to train the algorithm, and at least 49 of the genes are used to characterize a subject.

TABLE 1

| PAM50 Intrinsic Gene List | | | | | |
|---|---|---|---|---|---|
| GENE | REPRESENTATIVE GENBANK ACCESSION NUMBER | FORWARD PRIMER | SEQ ID NO: | REVERSE PRIMER | SEQ ID NO: |
| ACTR3B | NM_020445\| NM_001040135 | AAAGATTCCTGGG ACCTGA | 1 | TGGGGCAGTTCTGTA TTACTTC | 51 |
| ANLN | NM_018685 | ACAGCCACTTTCA GAAGCAAG | 2 | CGATGGTTTTGTACA AGATTTCTC | 52 |
| BAG1 | NM_004323 | CTGGAAGAGTTGA ATAAAGAGC | 3 | GCAAATCCTTGGGCA GA | 53 |
| BCL2 | NM_000633 | TACCTGAACCGGC ACCTG | 4 | GCCGTACAGTTCCAC AAAGG | 54 |
| BIRC5 | NM_001012271 | GCACAAAGCCATT CTAAGTC | 5 | GACGCTTCCTATCAC TCTATTC | 55 |
| BLVRA | BX647539 | GCTGGCTGAGCAG AAAG | 6 | TTCCTCCATCAAGAG TTCAACA | 56 |
| CCNB1 | NM_031966 | CTTTCGCCTGAGCC TATTT | 7 | GGGCACATCCAGAT GTTT | 57 |
| CCNE1 | BC035498 | GGCCAAAATCGAC AGGAC | 8 | GGGTCTGCACAGACT GCAT | 58 |
| CDC20 | BG256659 | CTGTCTGAGTGCC GTGGAT | 9 | TCCTTGTAATGGGGA GACCA | 59 |
| CDC6 | NM_001254 | GTAAATCACCTTCT GAGCCT | 10 | ACTTGGGATATGTGA ATAAGACC | 60 |
| CDCA1 | NM_031423 | GGAGGCGGAAGAA ACCAG | 11 | GGGGAAAGACAAAG TTTCCA | 61 |
| CDH3 | BC041846 | GACAAGGAGAATC AAAAGATCAGC | 12 | ACTGTCTGGGTCCAT GGCTA | 62 |
| CENPF | NM_016343 | GTGGCAGCAGATC ACAA | 13 | GGATTTCGTGGTGGG TTC | 63 |
| CEP55 | AB091343 | CCTCACGAATTGCT GAACTT | 14 | CCACAGTCTGTGATA AACGG | 64 |
| CXXC5 | BC006428 | CATGAAATAGTGC ATAGTTTGCC | 15 | CCATCAACATTCTCT TTATGAACG | 65 |
| EGFR | NM_005228 | ACACAGAATCTAT ACCCACCAGAGT | 16 | ATCAACTCCCAAACG GTCAC | 66 |
| ERBB2 | NM_001005862 | GCTGGCTCTCACA CTGATAG | 17 | GCCCTTACACATCGG AGAAC | 67 |

TABLE 1 -continued

| | PAM50 Intrinsic Gene List | | | | |
|---|---|---|---|---|---|
| GENE | REPRESENTATIVE GENBANK ACCESSION NUMBER | FORWARD PRIMER | SEQ ID NO: | REVERSE PRIMER | SEQ ID NO: |
| ESR1 | NM_001122742 | GCAGGGAGAGGAG TTTGT | 18 | GACTTCAGGGTGCTG GAC | 68 |
| EXO1 | NM_130398 | CCCATCCATGTGA GGAAGTATAA | 19 | TGTGAAGCCAGCAA TATGTATC | 69 |
| FGFR4 | AB209631 | CTTCTTGGACCTTG GCG | 20 | TATTGGGAGGCAGG AGGTTTA | 70 |
| FOXA1 | NM_004496 | GCTACTACGCAGA CACG | 21 | CTGAGTTCATGTTGC TGACC | 71 |
| FOXC1 | NM_001453 | GATGTTCGAGTCA CAGAGG | 22 | GACAGCTACTATTCC CGTT | 72 |
| GPR160 | AJ249248 | TTCGGCTGGAAGG AACC | 23 | TATGTGAGTAAGCTC GGAGAC | 73 |
| GRB7 | NM_005310 | CGTGGCAGATGTG AACGA | 24 | AGTGGGCATCCCGTA GA | 74 |
| HSPC150 (UBE2T) | NM_014176 | GGAGATCCGTCAA CTCCAAA | 25 | AGTGGACATGCGAG TGGAG | 75 |
| KIF2C | NM_006845 | TGGGTCGTGTCAG GAAAC | 26 | CACCGCTGGAAACT GAAC | 76 |
| KNTC2 | NM_006101 | CGCAGTCATCCAG AGATGTG | 27 | CGTGCACATCCATGA CCTT | 77 |
| KRT14 | BC042437 | ACTCAGTACAAGA AAGAACCG | 28 | GAGGAGATGACCTT GCC | 78 |
| KRT17 | AK095281 | GTTGGACCAGTCA ACATCTCTG | 29 | GCCATAGCCACTGCC ACT | 79 |
| KRT5 | M21389 | TGTGGCTCATTAG GCAAC | 30 | CTTCGACTGGACTCT GT | 80 |
| MAPT | NM_001123066 | GACTCCAAGCGCG AAAAC | 31 | CAGACATGTTGGTAT TGCACATT | 81 |
| MDM2 | M92424 | CCAACAAATATT CATGGTTCTTG | 32 | AGGCGATCCTGGGA AATTAT | 82 |
| MELK | NM_014791 | CCAGTAGCATTGT CCGAG | 33 | CCCATTTGTCTGTCT TCAC | 83 |
| MIA | BG765502 | GTCTCTGGTAATGC ACACT | 34 | CTGATGGTTGAGGCT GTT | 84 |
| MKI67 | NM_002417 | GTGGAATGCCTGC TGACC | 35 | CGCACTCCAGCACCT AGAC | 85 |
| MLPH | NM_024101 | AGGGGTGCCCTCT GAGAT | 36 | TCACAGGGTCAAACT TCCAGT | 86 |
| MMP11 | NM_005940 | CGAGATCGCCAAG ATGTT | 37 | GATGGTAGAGTTCCA GTGATT | 87 |
| MYBL2 | BX647151 | AGGCGAACACACA ACGTC | 38 | TCTGGTCACGCAGGG CAA | 88 |
| MYC | NM_002467 | AGCCTCGAACAAT TGAAGA | 39 | ACACAGATGATGGA GATGTC | 89 |
| NAT1 | BC013732 | ATCGACTGTGTAA ACAACTAGAGAAGA | 40 | AGTAGCTACATCTCC AGGTTCTCTG | 90 |
| ORC6L | NM_014321 | TTTAAGAGGGCAA TGGAAGG | 41 | CGGATTTTATCAACG ATGCAG | 91 |

TABLE 1 -continued

PAM50 Intrinsic Gene List

| GENE | REPRESENTATIVE GENBANK ACCESSION NUMBER | FORWARD PRIMER | SEQ ID NO: | REVERSE PRIMER | SEQ ID NO: |
|---|---|---|---|---|---|
| PGR | NM_000926 | TGCCGCAGAACTC ACTTG | 42 | CATTTGCCGTCCTTC ATCG | 92 |
| PHGDH | AK093306 | CCTCAGATGATGC CTATCCA | 43 | GCAGGTCAAAACTCT CAAAG | 93 |
| PTTG1 | BE904476 | CAGCAAGCGATGG CATAGT | 44 | AGCGGGCTTCTGTAA TCTGA | 94 |
| RRM2 | AK123010 | AATGCCACCGAAG CCTC | 45 | GCCTCAGATTTCAAC TCGT | 95 |
| SFRP1 | BC036503 | TCGAACTGAAGGC TATTTACGAG | 46 | CTGCTGAGAATCAA AGTGGGA | 96 |
| SLC39A6 | NM_012319 | GTCGAAGCCGCAA TTAGG | 47 | GGAACAAACTGCTCT GCCA | 97 |
| TMEM45B | AK098106 | CAAACGTGTGTTCT GGAAGG | 48 | ACAGCTCTTTAGCAT TTGTGGA | 98 |
| TYMS | BQ056428 | TGCCCTGTATGATG TCAGGA | 49 | GGGACTATCAATGTT GGGTTCTC | 99 |
| UBE2C | BC032677 | GTGAGGGGTGTCA GCTCAGT | 50 | CACACAGTTCACTGC TCCACA | 100 |

"Gene expression" as used herein refers to the relative levels of expression and/or pattern of expression of a gene. The expression of a gene may be measured at the level of DNA, cDNA, RNA, mRNA, or combinations thereof "Gene expression profile" refers to the levels of expression of multiple different genes measured for the same sample. An expression profile can be derived from a biological sample collected from a subject at one or more time points prior to, during, or following diagnosis, treatment, or therapy for breast cancer (or any combination thereof), can be derived from a biological sample collected from a subject at one or more time points during which there is no treatment or therapy for breast cancer (e.g., to monitor progression of disease or to assess development of disease in a subject at risk for breast cancer), or can be collected from a healthy subject. Gene expression profiles may be measured in a sample, such as samples comprising a variety of cell types, different tissues, different organs, or fluids (e.g., blood, urine, spinal fluid, sweat, saliva or serum) by various methods including but not limited to microarray technologies and quantitative and semi-quantitative RT-PCR techniques.

Clinical Variables

The PAM50 classification model described herein may be further combined with information on clinical variables to generate a continuous risk of relapse (ROR) predictor. As described herein, a number of clinical and prognostic breast cancer factors are known in the art and are used to predict treatment outcome and the likelihood of disease recurrence. Such factors include, for example, lymph node involvement, tumor size, histologic grade, estrogen and progesterone hormone receptor status, HER-2 levels, and tumor ploidy.

In one embodiment, risk of relapse (ROR) score is provided for a subject diagnosed with or suspected of having breast cancer. This score uses the PAM50 classification model in combination with clinical factors of lymph node status (N) and tumor size (T). Assessment of clinical variables is based on the American Joint Committee on Cancer (AJCC) standardized system for breast cancer staging. In this system, primary tumor size is categorized on a scale of 0-4 (T0: no evidence of primary tumor; T1: ≤2 cm; T2: >2 cm-≤5 cm; T3: >5 cm; T4: tumor of any size with direct spread to chest wall or skin). Lymph node status is classified as N0-N3 (N0: regional lymph nodes are free of metastasis; N1: metastasis to movable, same-side axillary lymph node(s); N2: metastasis to same-side lymph node(s) fixed to one another or to other structures; N3: metastasis to same-side lymph nodes beneath the breastbone). Methods of identifying breast cancer patients and staging the disease are well known and may include manual examination, biopsy, review of patient's and/or family history, and imaging techniques, such as mammography, magnetic resonance imaging (MRI), and positron emission tomography (PET).

Using the PAM50 classification methods of the present invention, the prognosis of a breast cancer patient can be determined independent of or in combination with assessment of these clinical factors. In some embodiments, combining the PAM50 breast cancer intrinsic subtype classification methods disclosed herein with evaluation of these clinical factors may permit a more accurate risk assessment. The methods of the invention may be further coupled with analysis of, for example, estrogen receptor (ER) and progesterone receptor (PgR) status, and/or HER-2 expression levels. Other factors, such as patient clinical history, family history and menopausal status, may also be considered when evaluating breast cancer prognosis via the methods of the invention.

Sample Source

In one embodiment of the present invention, breast cancer subtype is assessed through the evaluation of expression patterns, or profiles, of the intrinsic genes listed in Table 1 in one or more subject samples. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the invention. Accordingly, a subject can be diagnosed with breast cancer, can present with one or more symptoms of breast cancer, or a predisposing factor, such as a family (genetic) or medical history (medical) factor, for breast cancer, can be undergoing treatment or therapy for breast cancer, or the like. Alternatively, a subject can be healthy with respect to any of the aforementioned factors or criteria. It will be appreciated that the term "healthy" as used herein, is relative to breast cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more cancers other than breast cancer. However, the healthy controls are preferably free of any cancer.

In particular embodiments, the methods for predicting breast cancer intrinsic subtypes include collecting a biological sample comprising a cancer cell or tissue, such as a breast tissue sample or a primary breast tumor tissue sample. By "biological sample" is intended any sampling of cells, tissues, or bodily fluids in which expression of an intrinsic gene can be detected. Examples of such biological samples include, but are not limited to, biopsies and smears. Bodily fluids useful in the present invention include blood, lymph, urine, saliva, nipple aspirates, gynecological fluids, or any other bodily secretion or derivative thereof. Blood can include whole blood, plasma, serum, or any derivative of blood. In some embodiments, the biological sample includes breast cells, particularly breast tissue from a biopsy, such as a breast tumor tissue sample. Biological samples may be obtained from a subject by a variety of techniques including, for example, by scraping or swabbing an area, by using a needle to aspirate cells or bodily fluids, or by removing a tissue sample (i.e., biopsy). Methods for collecting various biological samples are well known in the art. In some embodiments, a breast tissue sample is obtained by, for example, fine needle aspiration biopsy, core needle biopsy, or excisional biopsy. Fixative and staining solutions may be applied to the cells or tissues for preserving the specimen and for facilitating examination. Biological samples, particularly breast tissue samples, may be transferred to a glass slide for viewing under magnification. In one embodiment, the biological sample is a formalin-fixed, paraffin-embedded breast tissue sample, particularly a primary breast tumor sample. In various embodiments, the tissue sample is obtained from a pathologist-guided tissue core sample as described in Example 4.

Expression Profiling

In various embodiments, the present invention provides methods for classifying, prognosticating, or monitoring breast cancer in subjects. In this embodiment, data obtained from analysis of intrinsic gene expression is evaluated using one or more pattern recognition algorithms. Such analysis methods may be used to form a predictive model, which can be used to classify test data. For example, one convenient and particularly effective method of classification employs multivariate statistical analysis modeling, first to form a model (a "predictive mathematical model") using data ("modeling data") from samples of known subtype (e.g., from subjects known to have a particular breast cancer intrinsic subtype. LumA, LumB, Basal-like, HER2-enriched, or normal-like), and second to classify an unknown sample (e.g., "test sample") according to subtype.

Pattern recognition methods have been used widely to characterize many different types of problems ranging, for example, over linguistics, fingerprinting, chemistry and psychology. In the context of the methods described herein, pattern recognition is the use of multivariate statistics, both parametric and non-parametric, to analyze data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. However, this type of approach may not be suitable for developing a clinical assay that can be used to classify samples derived from subjects independent of the initial sample population used to train the prediction algorithm.

The other approach is termed "supervised" whereby a training set of samples with known class or outcome is used to produce a mathematical model which is then evaluated with independent validation data sets. Here, a "training set" of intrinsic gene expression data is used to construct a statistical model that predicts correctly the "subtype" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each subtype in terms of its intrinsic gene expression profile. It is also possible to obtain confidence limits on any predictions, for example, a level of probability to be placed on the goodness of fit (see, for example, Kowalski et al., 1986). The robustness of the predictive models can also be checked using cross-validation, by leaving out selected samples from the analysis.

The PAM50 classification model described herein is based on the gene expression profile for a plurality of subject samples using the intrinsic genes listed in Table 1. The plurality of samples includes a sufficient number of samples derived from subjects belonging to each subtype class. By "sufficient samples" or "representative number" in this context is intended a quantity of samples derived from each subtype that is sufficient for building a classification model that can reliably distinguish each subtype from all others in the group. A supervised prediction algorithm is developed based on the profiles of objectively-selected prototype samples for "training" the algorithm. The samples are selected and subtyped using an expanded intrinsic gene set according to the methods disclosed in International Patent Publication WO 2007/061876, which is herein incorporated by reference in its entirety. Alternatively, the samples can be subtyped according to any known assay for classifying breast cancer subtypes. After stratifying the training samples according to subtype, a centroid-based prediction algorithm is used to construct centroids based on the expression profile of the intrinsic gene set described in Table 1.

In one embodiment, the prediction algorithm is the nearest centroid methodology related to that described in Narashiman and Chu (2002) PNAS 99:6567-6572, which is herein incorporated by reference in its entirety. In the present invention, the method computes a standardized centroid for each subtype. This centroid is the average gene expression for each gene in each subtype (or "class") divided by the within-class standard deviation for that gene. Nearest centroid classification takes the gene expression profile of a new sample, and compares it to each of these class centroids. Subtype prediction is done by calculating the Spearman's rank correlation of each test case to the five centroids, and assigning a sample to a subtype based on the nearest centroid.

Detection of Intrinsic Gene Expression

Any methods available in the art for detecting expression of the intrinsic genes listed in Table 1 are encompassed herein. By "detecting expression" is intended determining the quantity or presence of an RNA transcript or its expression product of an intrinsic gene.

Methods for detecting expression of the intrinsic genes of the invention, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the intrinsic genes listed in Table 1. In preferred embodiments, PCR-based methods, such as reverse transcription PCR (RT-PCR) (Weis et al., TIG 8:263-64, 1992), and array-based methods such as microarray (Schena et al., Science 270:467-70, 1995) are used. By "microarray" is intended an ordered arrangement of hybridizable array elements, such as, for example, polynucleotide probes, on a substrate. The term "probe" refers to any molecule that is capable of selectively binding to a specifically intended target biomolecule, for example, a nucleotide transcript or a protein encoded by or corresponding to an intrinsic gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Many expression detection methods use isolated RNA. The starting material is typically total RNA isolated from a biological sample, such as a tumor or tumor cell line, and corresponding normal tissue or cell line, respectively. If the source of RNA is a primary tumor, RNA (e.g., mRNA) can be extracted, for example, from frozen or archived paraffin-embedded and fixed (e.g., formalin-fixed) tissue samples (e.g., pathologist-guided tissue core samples).

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56: A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MASTERPURE® Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155).

Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present invention, or any derivative DNA or RNA. Hybridization of an mRNA with the probe indicates that the intrinsic gene in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probes are immobilized on a solid surface and the mRNA is contacted with the probes, for example, in an Agilent gene chip array. A skilled artisan can readily adapt known mRNA detection methods for use in detecting the level of expression of the intrinsic genes of the present invention.

An alternative method for determining the level of intrinsic gene expression product in a sample involves the process of nucleic acid amplification, for example, by RT-PCR (U.S. Pat. No. 4,683,202), ligase chain reaction (Barany, Proc. Natl. Acad. Sci. USA 88:189-93, 1991), self-sustained sequence replication (Guatelli et al., Proc. Natl. Acad. Sci. USA 87:1874-78, 1990), transcriptional amplification system (Kwoh et al., Proc. Natl. Acad. Sci. USA 86:1173-77, 1989), Q-Beta Replicase (Lizardi et al., Bio/Technology 6:1197, 1988), rolling circle replication (U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers.

In particular aspects of the invention, intrinsic gene expression is assessed by quantitative RT-PCR. Numerous different PCR or QPCR protocols are known in the art and exemplified herein below and can be directly applied or adapted for use using the presently-described compositions for the detection and/or quantification of the intrinsic genes listed in Table 1. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real-time fluorescence measurement capabilities, for example, SMARTCYCLER® (Cepheid, Sunnyvale, Calif.), ABI PRISM 7700® (Applied Biosystems, Foster City, Calif.), ROTOR-GENE® (Corbett Research, Sydney, Australia), LIGHTCYCLER® (Roche Diagnostics Corp, Indianapolis, Ind.), ICYCLER® (Biorad Laboratories, Hercules, Calif.) and MX4000R (Stratagene, La Jolla, Calif.).

Quantitative PCR (QPCR) (also referred as real-time PCR) is preferred under some circumstances because it provides not only a quantitative measurement, but also reduced time and contamination. In some instances, the availability of full gene expression profiling techniques is limited due to requirements for fresh frozen tissue and specialized laboratory equipment, making the routine use of such technologies difficult in a clinical setting. However, QPCR gene measurement can be applied to standard formalin-fixed paraffin-embedded clinical tumor blocks, such as those used in archival tissue banks and routine surgical pathology specimens (Cronin et al. (2007) Clin Chem 53:1084-91) [Mullins 2007] [Paik 2004]. As used herein, "quantitative PCR (or "real time QPCR") refers to the direct monitoring of the progress of PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

In another embodiment of the invention, microarrays are used for expression profiling. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, for example, U.S. Pat. Nos. 6,040,138, 5,800,992 and 6,020, 135, 6,033,860, and 6,344,316. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992. Arrays can be packaged in such a manner as to allow for diagnostics or other manipulation of an all-inclusive device. See, for example, U.S. Pat. Nos. 5,856,174 and 5,922,591.

In a specific embodiment of the microarray technique, PCR amplified inserts of cDNA clones are applied to a substrate in a dense array. The microarrayed genes, immobilized on the microchip, are suitable for hybridization under stringent conditions. Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance.

With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93:106-49, 1996). Microarray analysis can be performed by commercially available equipment, following manufacturer's protocols, such as by using the Affymetrix GenChip technology, or Agilent ink jet microarray technology. The development of microarray methods for large-scale analysis of gene expression makes it possible to search systematically for molecular markers of cancer classification and outcome prediction in a variety of tumor types.

Data Processing

It is often useful to pre-process gene expression data, for example, by addressing missing data, translation, scaling, normalization, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill").

"Translation" of the descriptor coordinate axes can be useful. Examples of such translation include normalization and mean centering. "Normalization" may be used to remove sample-to-sample variation. For microarray data, the process of normalization aims to remove systematic errors by balancing the fluorescence intensities of the two labeling dyes. The dye bias can come from various sources including differences in dye labeling efficiencies, heat and light sensitivities, as well as scanner settings for scanning two channels. Some commonly used methods for calculating normalization factor include: (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush (2002) Nat. Genet. 32 (Suppl.), 496-501). In one embodiment, the intrinsic genes disclosed herein can be normalized to control housekeeping genes. For example, the housekeeping genes described in U.S. Patent Publication 2008/0032293, which is herein incorporated by reference in its entirety, can be used for normalization.

Exemplary housekeeping genes include MRPL19, PSMC4, SF3A1, PUM1, ACTB, GAPD, GUSB, RPLP0, and TFRC. It will be understood by one of skill in the art that the methods disclosed herein are not bound by normalization to any particular housekeeping genes, and that any suitable housekeeping gene(s) known in the art can be used.

Many normalization approaches are possible, and they can often be applied at any of several points in the analysis. In one embodiment, microarray data is normalized using the LOWESS method, which is a global locally weighted scatterplot smoothing normalization function. In another embodiment, qPCR data is normalized to the geometric mean of set of multiple housekeeping genes.

"Mean centering" may also be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

In one embodiment, data is collected for one or more test samples and classified using the PAM50 classification model described herein. When comparing data from multiple analyses (e.g., comparing expression profiles for one or more test samples to the centroids constructed from samples collected and analyzed in an independent study), it will be necessary to normalize data across these data sets. In one embodiment, Distance Weighted Discrimination (DWD) is used to combine these data sets together (Benito et al. (2004) Bioinformatics 20(1):105-114, incorporated by reference herein in its entirety). DWD is a multivariate analysis tool that is able to identify systematic biases present in separate data sets and then make a global adjustment to compensate for these biases; in essence, each separate data set is a multi-dimensional cloud of data points, and DWD takes two points clouds and shifts one such that it more optimally overlaps the other.

The methods described herein may be implemented and/ or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

Calculation of Risk of Relapse

Provided herein are methods for predicting breast cancer outcome within the context of the intrinsic subtype and optionally other clinical variables. Outcome may refer to overall or disease-specific survival, event-free survival, or outcome in response to a particular treatment or therapy. In particular, the methods may be used to predict the likelihood of long-term, disease-free survival. "Predicting the likelihood of survival of a breast cancer patient" is intended to assess the risk that a patient will die as a result of the underlying breast cancer. "Long-term, disease-free survival" is intended to mean that the patient does not die from or suffer a recurrence of the underlying breast cancer within a period of at least five years, or at least ten or more years, following initial diagnosis or treatment.

In one embodiment, outcome is predicted based on classification of a subject according to subtype. This classification is based on expression profiling using the list of intrinsic genes listed in Table 1. As discussed in Example 1, tumor subtype according to the PAM50 model was more indicative of response to chemotherapy than standard clinical marker classification. Tumors classified as HER2+ using clinical markers but not HER2-enriched using the PAM50 model had a lower pathological complete response (pCR) to a regimen of paclitaxel, 5-fluorouracil, adriamycin, and cyclophosphamide (T/FAC) than tumors classified as HER2+ clinically and belonging to the HER2-enriched expression subtype. Similarly, Basal-like tumors that were not clinically scored as triple-negative (ER-, PgR- and HER2-) had a higher pCR compared to triple-negative tumors that were not Basal-like by PAM50. Thus, the PAM50 model can be used to more accurately predict response to chemotherapy than standard clinical markers.

In addition to providing a subtype assignment, the PAM50 bioinformatics model provides a measurement of the similarity of a test sample to all four subtypes which is translated into a Risk Of Relapse (ROR) score that can be used in any patient population regardless of disease status and treatment options. The intrinsic subtypes and ROR also have value in the prediction of pathological complete response in women treated with, for example, neoadjuvant taxane and anthracycline chemotherapy [Rouzier 2005]. Thus, in various embodiments of the present invention, a risk of relapse (ROR) model is used to predict outcome. Using these risk models, subjects can be stratified into low, medium, and high risk of relapse groups. Calculation of ROR can provide prognostic information to guide treatment decisions and/or monitor response to therapy.

In some embodiments described herein, the prognostic performance of the PAM50-defined intrinsic subtypes and/or other clinical parameters is assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard (i.e., risk) of individuals given their prognostic variables (e.g., intrinsic gene expression profile with or without additional clinical factors, as described herein). The "hazard ratio" is the risk of death at any given time point for patients displaying particular prognostic variables. See generally Spruance et al., Antimicrob. Agents & Chemo. 48:2787-92, 2004.

The PAM50 classification model described herein can be trained for risk of relapse using subtype distances (or correlations) alone, or using subtype distances with clinical variables as discussed supra. In one embodiment, the risk score for a test sample is calculated using intrinsic subtype distances alone using the following equation: $ROR=0.05*Basal+0.11*Her2+-0.25*LumA+0.07*LumB+-0.11*Normal$, where the variables "Basal," "Her2," "LumA," "LumB," and "Normal" are the distances to the centroid for each respective classifier when the expression profile from a test sample is compared to centroids constructed using the gene expression data deposited with the Gene Expression Omnibus (GEO) as accession number GSE2845. It is also possible that other data sets could be used to derive similar Cox Model coefficients. When using the intrinsic gene list set forth in Table 1 to develop a prediction model from a sample set other than the samples used to derive the dataset deposited as GSE2845, the methods described in Example 1 or Example 3 can be used to construct a formula for calculating the risk of relapse from this alternate sample set.

Risk score can also be calculated using a combination of breast cancer subtype and the clinical variables tumor size (T) and lymph nodes status (N) using the following equation: $ROR$ $(full)=0.05*Basal+0.1*Her2+-0.19*LumA+0.05*LumB+-0.09*Normal+0.16*T+0.08*-N$, again when comparing test expression profiles to centroids constructed using the gene expression data deposited with GEO as accession number GSE2845.

In yet another embodiment, risk score for a test sample is calculated using intrinsic subtype distances alone using the following equation: $ROR-S=0.05*Basal+0.12*Her2+-0.34*LumA+0.0.23*LumB$, where the variables "Basal," "Her2," "LumA," and "LumB" are as described supra and the test expression profiles are compared to centroids constructed using the gene expression data deposited with GEO as accession number GSE2845.

In yet another embodiment, risk score can also be calculated using a combination of breast cancer subtype and the clinical variable tumor size (T) using the following equation (where the variables are as described supra): $ROR-C=0.05*Basal+0.11*Her2+-0.23*LumA+0.09*LumB+0.17*T$.

Prediction of Response to Therapy

Breast cancer is managed by several alternative strategies that may include, for example, surgery, radiation therapy, hormone therapy, chemotherapy, or some combination thereof. As is known in the art, treatment decisions for individual breast cancer patients can be based on endocrine responsiveness of the tumor, menopausal status of the patient, the location and number of patient lymph nodes involved, estrogen and progesterone receptor status of the tumor, size of the primary tumor, patient age, and stage of the disease at diagnosis. Analysis of a variety of clinical factors and clinical trials has led to the development of recommendations and treatment guidelines for early-stage breast cancer by the International Consensus Panel of the St. Gallen Conference (2005). See, Goldhirsch et al., Annals Oncol. 16:1569-83, 2005. The guidelines recommend that patients be offered chemotherapy for endocrine non-responsive disease; endocrine therapy as the primary therapy for endocrine responsive disease, adding chemotherapy for some intermediate- and all high-risk groups in this category; and both chemotherapy and endocrine therapy for all patients in the uncertain endocrine response category except those in the low-risk group.

Stratification of patients according to risk of relapse using the PAM50 model and risk score disclosed herein provides an additional or alternative treatment decision-making factor. The methods comprise evaluating risk of relapse using the PAM50 classification model optionally in combination with one or more clinical variables, such as node status, tumor size, and ER status. The risk score can be used to guide treatment decisions. For example, a subject having a low risk score may not benefit from certain types of therapy, whereas a subject having a high risk score may be indicated for a more aggressive therapy.

The methods of the invention find particular use in choosing appropriate treatment for early-stage breast cancer patients. The majority of breast cancer patients diagnosed at an early-stage of the disease enjoy long-term survival following surgery and/or radiation therapy without further adjuvant therapy. However, a significant percentage (approximately 20%) of these patients will suffer disease recurrence or death, leading to clinical recommendations that some or all early-stage breast cancer patients should receive adjuvant therapy. The methods of the present invention find use in identifying this high-risk, poor prognosis population of early-stage breast cancer patients and thereby determining which patients would benefit from continued and/or more aggressive therapy and close monitoring following treatment. For example, early-stage breast cancer patients assessed as having a high risk score by the methods disclosed herein may be selected for more aggressive adjuvant therapy, such as chemotherapy, following surgery and/or radiation treatment. In particular embodiments, the methods of the present invention may be used in conjunction with the treatment guidelines established by the St. Gallen Conference to permit physicians to make more informed breast cancer treatment decisions.

In various embodiments, the PAM50 classification model provides information about breast cancer subtypes that cannot be obtained using standard clinical assays such as immunohistochemistry or other histological analyses. For example, subjects scored as estrogen receptor (ER)-positive and/or progesterone-receptor (PR)-positive would be indicated under conventional guidelines for endocrine therapy. As discussed in Example 2, the model disclosed herein is capable of identifying a subset of these ER+/PgR+ cases that are classified as Basal-like, which may indicate the need for more aggressive therapy that would not have been indicated based on ER or PgR status alone.

Thus, the methods disclosed herein also find use in predicting the response of a breast cancer patient to a selected treatment. "Predicting the response of a breast cancer patient to a selected treatment" is intended to mean assessing the likelihood that a patient will experience a positive or negative outcome with a particular treatment. As used herein, "indicative of a positive treatment outcome" refers to an increased likelihood that the patient will experience beneficial results from the selected treatment (e.g., complete or partial remission, reduced tumor size, etc.). "Indicative of a negative treatment outcome" is intended to mean an increased likelihood that the patient will not benefit from the selected treatment with respect to the progression of the underlying breast cancer.

In some embodiments, the relevant time for assessing prognosis or disease-free survival time begins with the surgical removal of the tumor or suppression, mitigation, or inhibition of tumor growth. In another embodiment, the PAM50-based risk score is calculated based on a sample obtained after initiation of neoadjuvant therapy such as endocrine therapy. The sample may be taken at any time following initiation of therapy, but is preferably obtained after about one month so that neoadjuvant therapy can be switched to chemotherapy in unresponsive patients. It has been shown that a subset of tumors indicated for endocrine treatment before surgery is non-responsive to this therapy. The model provided herein can be used to identify aggressive tumors that are likely to be refractory to endocrine therapy, even when tumors are positive for estrogen and/or progesterone receptors. In this embodiment, a proliferation-weighted PAM50 risk score is obtained according the following equation: RSp=(−0.0129*Basal)+(0.106*Her2)+(−0.112*LumA)+(0.039*LumB)+(−0.069*Norma−1)+(0.272*Prolif), where the proliferation score ("prolif") is assigned as the mean measurement of the following genes (after normalization): CCNB1, UBE2C, BIRCS, KNTC2, CDC20, PTTG1, RRM2, MKI67, TYMS, CEP55, and CDCA1. All other variables are the same as the RS equations described infra. As discussed in Example 2, assessment of risk score after initiation of therapy is more predictive of outcome to treatment, at least in a population of ER+ patients undergoing neoadjuvant endocrine therapy.

Kits

The present invention also provides kits useful for classifying breast cancer intrinsic subtypes and/or providing prognostic information. These kits comprise a set of capture probes and/or primers specific for the intrinsic genes listed in Table 1, as well as reagents sufficient to facilitate detection and/or quantitation of the intrinsic gene expression product. The kit may further comprise a computer readable medium.

In one embodiment of the present invention, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the invention comprise a substrate having a plurality of capture probes that can specifically bind an intrinsic gene expression product. The number of capture probes on the substrate varies with the purpose for which the array is intended. The arrays may be low-density arrays or high-density arrays and may contain 4 or more, 8 or more, 12 or more, 16 or more, 32 or more addresses, but will minimally comprise capture probes for the 50 intrinsic genes listed in Table 1.

Techniques for the synthesis of these arrays using mechanical synthesis methods are described in, e.g., U.S. Pat. No. 5,384,261, incorporated herein by reference in its entirety for all purposes. The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation on the device. See, for example, U.S. Pat. Nos. 5,856,174 and 5,922,591 herein incorporated by reference.

In another embodiment, the kit comprises a set of oligonucleotide primers sufficient for the detection and/or quantitation of each of the intrinsic genes listed in Table 1. The oligonucleotide primers may be provided in a lyophilized or reconstituted form, or may be provided as a set of nucleotide sequences. In one embodiment, the primers are provided in a microplate format, where each primer set occupies a well (or multiple wells, as in the case of replicates) in the microplate. The microplate may further comprise primers sufficient for the detection of one or more housekeeping genes as discussed infra. The kit may further comprise reagents and instructions sufficient for the amplification of expression products from the genes listed in Table 1.

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation:

EXPERIMENTAL

Example 1

Methods

Samples and Clinical Data:

Patient cohorts for training and test sets consisted of samples with data already in the public domain (Loi et al. (2007) J. Clin. Oncol. 25:1239-1246; va de Vijver et al. (2002) N Engl J Med 247:1999-2009; Wang et al (2005) Lancet 365:671-679; Ishvina et al. (2006) Cancer Res 66:10292-10301; and Hess et al (2006) J Clin Oncol 24:4236-4244, each of which is incorporated by reference in its entirety) and fresh frozen and formalin-fixed paraffin-embedded (FFPE) tissues collected under institutional review board-approved protocols at the respective institutions.

A training set of 189 breast tumor samples and 29 normal samples was procured as fresh frozen and FFPE tissues under approved IRB protocols at the University of North Carolina at Chapel Hill, The University of Utah, Thomas Jefferson University, and Washington University. The training set, which was gene expression profiled by microarray and qRT-PCR, had a median follow-up of 49 months and represents heterogeneously treated patients in accordance with the standard of care dictated by their stage, ER and HER2 status. A test set of 279 breast cancers with long-term, disease-specific survival was gene expression profiled from FFPE by qRT-PCR. The clinical data for the training and test set assayed by qRT-PCR are provided in Tables 2 and 3.

Nucleic Acid Extraction:

Total RNA was purified from fresh frozen samples for microarray using the Qiagen RNeasy Midi Kit according to the manufacturer's protocol (Qiagen, Valencia Calif.). The integrity of the RNA was determined using an Agilent 2100 Bioanalyzer (Agilent Technologies, Palo Alto, Calif.). The High Pure RNA Paraffin Kit (Roche Applied Science, Indianapolis, Ind.) was used to extract RNA from FFPE tissues (2×10 micron or 1.5 mm punches) for qRT-PCR. Contaminating DNA was removed using Turbo DNase (Ambion, Austin, Tex.). The yield of total RNA was assessed using the Nanoprop ND-1000 Spectrophotometer (Nanoprop Technologies, Inc., Rockland, Del.).

Reverse Transcription and Real-Time Quantitative POR:

First-strand cDNA was synthesized from 1.2 µtotal RNA using Superscript III reverse transcriptase (1st Strand Kit; Invitrogen, Carlsbad, Calif.) and a mixture of random hexamers and gene specific primers. The reaction was held at 55° C. for 60 minutes and then 70° C. for 15 minutes. The cDNA was washed on a QIAquick PCR purification column (Qiagen Inc., Valencia, Calif.) and stored at −80° C. in 25 mM Tris, 1 mM EDTA until further use. Each 54, PCR reaction included 1.25 ng (0.625 ng/µL) cDNA from samples of interest or 10 ng (5 ng/µL) for reference, 2 pmol of both upstream and downstream primers, and 2× LightCycler 480 SYBR Green I Master Mix (Roche Applied Science, Indianapolis, Ind.). Each run contained a single gene profiled in duplicate for test samples, reference sample, and negative control. The reference sample cDNA was comprised of an equal contribution of Human Reference Total RNA (Stratagene, La Jolla, Calif.) and the breast cell lines MCF7, ME16C, and SKBR3. PCR amplification was performed with the LightCycler 480 (Roche Applied Science, Indianapolis, Ind.) using an initial denaturation step (95° C., 8 minutes) followed by 45 cycles of denaturation (95° C., 4 seconds), annealing (56° C., 6 seconds with 2.5° C./s transition), and extension (72° C., 6 seconds with 2° C./see transition). Fluorescence (530 nm) from the dsDNA dye SYBR Green I was acquired each cycle after the extension step. The specificity of the PCR was determined by post-amplification melting curve analysis—samples were cooled to 65° C. and slowly heated at 2° C./s to 99° C. while continuously monitoring fluorescence (10 acquisitions/1° C.). The relative copy number for each gene was determined from a within run calibrator set at 10 ng and using a PCR efficiency of 1.9. Each of the PAM50 classifier genes was normalized to the geometric mean of 5 housekeepers.

Microarray:

Total RNA isolation, labeling and hybridizations on Agilent human 1Av2 microarrays or custom designed Agilent human 22 k arrays were performed using the protocol described in Hu et al (6). All microarray data have been deposited into the GEO under the accession number of GSE10886. Sources for all microarray training and test data sets are given in Table 4.

Pre-Processing of Microarray Data:

Microarray data for the training set (189 samples) were extracted from the University of North Carolina (UNC) microarray database. Raw signal intensities from both channels were lowess normalized by chip and probes were excluded from data analysis if they did not have signal intensity of at least 30 in both channels for at least 70% of the experiments. The normalized data for this set have been placed on GEO (GSE10886). The training set was median-centered and gene symbols were assigned using the manufacturer provided annotation. Duplicate gene symbols were collapsed by averaging within each sample.

Normalized data for all test sets were downloaded from GEO (GSE2845, GSE6532, GSE4922, GSE2034, GSE10886) or the publicly-available data found at the world wide web (www) at bioinformatics.mdanderson [dot] org/pubdata (see Table 5). All intensity measures (ratios for the NKI data) were log-transformed. Prior to nearest centroid calculation, the Hess et al. (see the world wide web (www) at bioinformatics.mdanderson [dot] org/pubdata), van de Vijver et al. (GSE2845), and Wang et al. (GSE2034) datasets were median centered to minimize platform effects. Adjustment in this way assumes a relatively similar sampling of the population as the training set. The Loi et al. (GSE6532) and Ivshina et al. (GSE4922) datasets were heavily enriched for ER+ samples relative to the training set, thus the underlying assumption may be violated for these sets. In these two instances the genes in the training set were centered to the median of the ER+ samples (as opposed to the median across all samples). As with the training set, gene symbols were assigned using the manufacturer provided annotation, and duplicate gene symbols were collapsed by averaging within each sample.

Identification of Prototypical Intrinsic Subtype Samples and Genes:

An expanded "intrinsic" gene set, comprised primarily of genes found in 4 previous studies (1, 6, 9, 11), was initially used to identify prototypical tumor samples. The Normal-like class was represented using true "normals" from reduction mammoplasty or grossly uninvolved tissue. 189 breast tumors across 1906 "intrinsic" genes were analyzed by hierarchical clustering (median centered by feature/gene, Pearson correlation, average linkage) (12) and the sample dendrogram was analyzed using "SigClust" (13). The SigClust algorithm statistically identifies significant/unique groups by testing the null hypothesis that a group of samples is from a single cluster, where a cluster is characterized as a multivariate normal distribution. SigClust was run at each node of the dendrogram beginning at the root and stopping when the test was no longer significant (p>0.001).

Gene Set Reduction Using Prototype Samples and qRT-PCR:

122 breast cancers from 189 individuals profiled by qRT-PCR and microarray had prototypical profiles as determined by SigClust (Table 2). A minimized gene set was derived from these prototypical samples using the qRT-PCR data for 161 genes that passed FFPE performance criteria established in Mullins et al (14). Several minimization methods were employed including top "N" t-test statistics for each group (15), top cluster index scores (16), and the remaining genes after 'shrinkage' of modified t-test statistics (17). Cross-validation (random 10% left out in each of 50 cycles) was used to assess the robustness of the minimized gene sets. The "N" t-test method was selected due to having the lowest CV error.

Sample Subtype Prediction:

Minimized gene sets were compared for reproducibility of classification across 3 centroid-based prediction methods: Prediction Analysis of Microarray (PAM) (17), a simple nearest centroid (6), and Classification of Nearest Centroid (ClaNC) (18). Subtype prediction was done by calculating the Spearman's rank correlation of each test case to five centroids (LumA, LumB, HER2-enriched, Basal-like, and Normal-like) and class was assigned based upon the nearest centroid. Centroids were constructed as described for the PAM algorithm (17) using the data provided in GSE10886; however, no "shrinkage" was used and the Spearman's rank correlation was used for the distance measure. This method was selected as the classifier because of its reproducibility of subtype predictions from large and minimized gene sets. The final 50-gene classifier (henceforth called PAM50) was used to make subtype predictions onto 6 microarray datasets and 1 qRT-PCR dataset (Table 4). The Hess et al dataset (19) does not have outcome data and is evaluated based on clinical markers, subtypes, and neo-adjuvant response.

Prognosis Using Clinical and Molecular Subtype Data:

The prognostic significance of the intrinsic subtype classification was assessed along with standard clinical variables (tumor size (T), node status (N), and ER status) using univariate and multivariate analyses with time to relapse (i.e., any event) as the endpoint. Likelihood ratio tests were performed to compare models of available clinical data, subtype data, and combined clinical and molecular variables. Categorical survival analyses were performed using a log rank test and visualized with Kaplan-Meier plots.

Developing Risk Models with Clinical and Molecular Data:

Models were trained for risk of relapse (ROR) predictions using subtype alone, and subtype with clinical information. In both cases, a multivariate Cox model using Ridge regression was fit to the untreated subset of the NKI295 cohort (20). A risk score was assigned to each test case using correlation to the subtype alone (ROR; model 1) or using a full model with subtype correlation and two clinical variables (ROR (full); model 2):

(1) $ROR=0.05*Basal+0.11*Her2+-0.25*LumA+0.07*LumB+-0.11*Normal$ (2) $ROR (full)=0.05*Basal+0.1*Her2+-0.19*LumA+0.05*LumB+-0.09*Normal +0.16*T+0-0.08*N$ The sum of the coefficients from the Cox model is the "risk of relapse" score for each patient. In order to classify samples into specific risk groups, thresholds were chosen from the NKI training set that required no LumA sample to be in the high risk group and no Basal-like sample to be in the low risk group. Thresholds were determined from the training set and remained unchanged when evaluating test cases. Predictions for the subtype only and combined models were compared using the C Index (see the world wide web (www) at lib.stat.cmu [dot] edu/S/Harrell/Design.html). SiZer analysis was performed to characterize the relationship between the ROR score and relapse free survival (21). The 95% confidence intervals for the ROR score are local versions of binomial confidence intervals, with the local sample size computed from a Gaussian kernel density estimator, based on the Sheather-Jones choice of window width (22).

Results

Creating a New Subtype Model Based Upon Prototypical Samples and Genes:

There have been numerous studies that have analyzed interactions between breast cancer intrinsic subtypes and prognosis (1, 6, 9), genetic alterations (23), and drug response (24). The purpose of the methods described here was to standardize and validate a classification for the intrinsic subtypes for clinical and research purposes. "SigClust" objectively identified five intrinsic breast subtypes from clustered microarray data. These prototypes were then used to derive a minimal 50-gene set (PAM50). Finally, the best classification method was selected and used with the PAM50 to predict subtypes on multiple test sets from microarray and qRT-PCR data. Of the 5 microarray studies with outcome data (Table 4), the UNC cohort had significantly worse outcomes than the others. Subtype predictions onto a combined microarray test set showed prognostic significance across all patients, in patients given endocrine treatment alone, and in node negative patients receiving no systemic adjuvant therapy (FIGS. 1A to 1C).

Molecular and clinical predictors of survival were assessed in univariate and multivariate analyses on 1451 patients (Table 5). In univariate analysis, the LumA, LumB, and HER2-enriched subtypes were all found to be significant, as were the clinical variables ER, T, and N. The LumA and HER2-enriched subtypes and the clinical variables were also significant in multivariate analyses, suggesting that the most comprehensive model should include subtype and clinical information. Testing this hypothesis revealed that the combined model accounts for significantly more variation in survival than either the subtype or clinical variables alone (p<0.0001 for both tests).

Distribution of Biological Subtypes Across ER Positive and ER-Negative Tumors:

Of all ER-positive tumors in the combined microarray test set, 73% were Luminal (A and B), 10% were HER2-enriched, and 5% were Basal-like (Table 6). Conversely when ER-negative tumors were considered, approximately 13% were Luminal (A and B), 31% were HER2-enriched and 48% were Basal-like. Tumors identified as the Normal-like subtype were divided almost equally between ER-positive (11%) and ER-negative (8%) tumors. Therefore, while subtype representation markedly changed in distribution depending on ER-status, all subtypes were represented in both ER-positive and ER-negative categories. Outcome plots for the subtypes in ER-positive cases alone were significant for relapse free survival and followed the same trends as seen when considering all invasive breast disease.

Subtypes and Response to Neoadjuvant T FAC Treatment:

The Hess et al. study that performed microarray on tumors from patients given a regimen of paclitaxel, 5-fluorouracil, adriamycin, and cyclophosphamide (T/FAC) (19) allowed investigation of the relationship between the PAM50 subtypes, clinical markers, and how each relates to pathological complete response (pCR). For HER2 status, 64% of tumors that were HER2-positive by clinical assay (FISH+ and/or IHC 3+, referred to as HER2+clin) were classified into the HER2-enriched expression subtype, with the rest of the HER2+clin mostly associated with the Luminal subtypes. Tumors that were HER2+clin but not of the HER2-enriched expression subtype had a low pCR rate (16%) versus those that were HER2+clin and HER2-enriched expression subtype (52%).

Another relevant clinical distinction is the classification of "triple-negative" tumors (ER−, PgR− and HER2−), of which 65% were called Basal-like by the PAM50, with the remainder being called HER2-enriched (15%), LumA (4%), LumB (4%), and Normal-like (12%). The PAM50 classification of Basal-like appears superior to the clinical triple-negative with respect to pCR rate in that Basal-like tumors that were not scored as triple-negative had a 50% pCR compared to triple-negative tumors that were not Basal-like by PAM50 (22% pCR, Table 7).

Figures 3A, 3B:
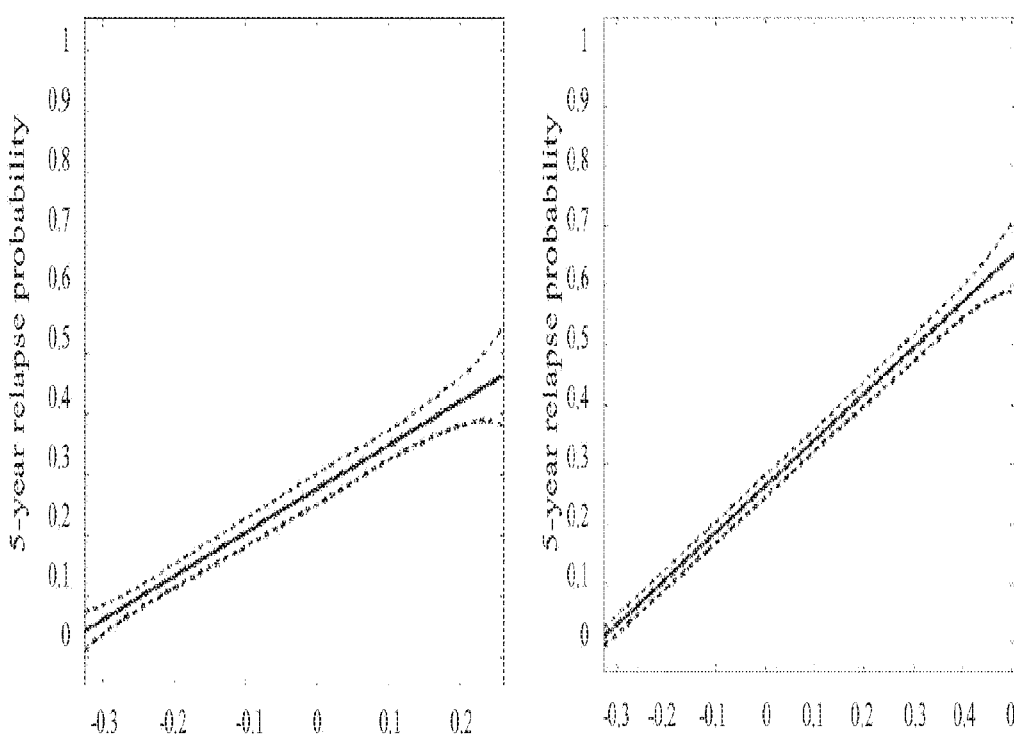
FIGS. 3A and 3B shows the linear score for prognosis using the subtype-clinical model for risk of relapse at 5 years. Linear fit with 95% confidence intervals calibrates the risk of relapse score. The continuous risk model with subtype and clinical variables (T and N) was calibrated from 657 patients with ER-positive early stage breast cancer (FIG. 3A), and in 1286 patients with ER-positive and ER-negative disease and stage 1-3 (FIG. 3B).
Figures 7A, 7B:
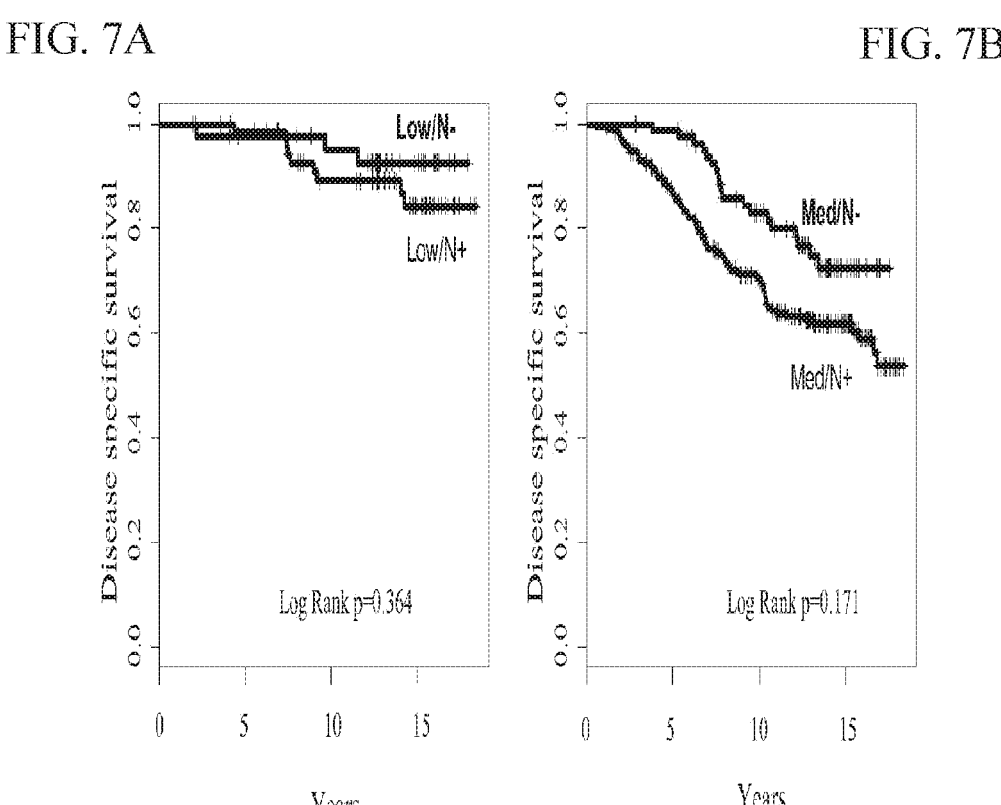
Figure 8:
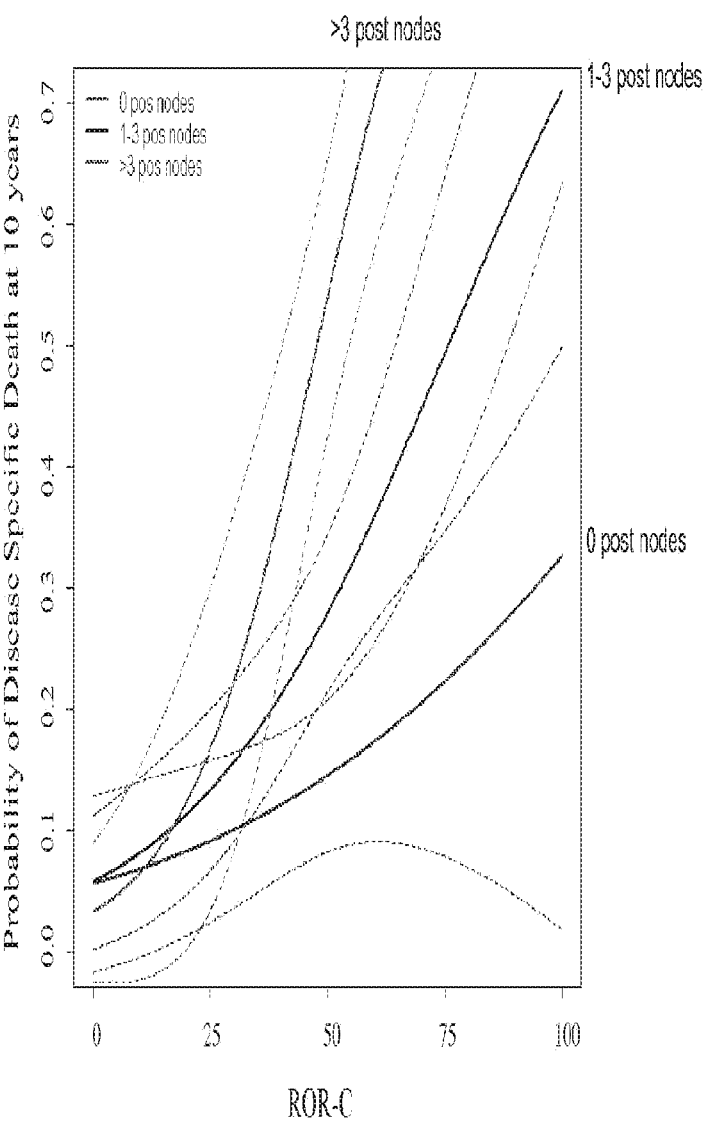
FIG. 8 shows that an analysis of the ROR-C model versus probability of survival, stratified by the number of involved lymph nodes, reveals good outcomes regardless of nodal status category among patients with ROR-C values less than 25, who have overlapping 95% confidence intervals (denoted by dashed lines)

Risk Prediction Based on Biological Subtype:

A supervised risk classifier was developed to predict outcomes within the context of the intrinsic subtypes and clinical variables. An untreated cohort was selected from the NKI microarray dataset to train the risk of relapse (ROR) model and select cut-offs. Two Cox models (one based upon subtype alone and another based upon subtype, tumor size, and node status) were validated using the combined microarray test set. Excluding clinical variables, the subtype only model performed well at stratifying patients into low, medium, and high risk of relapse groups (c-index=0.65 [0.61-0.69]); however, the full model (subtype, tumor size, node status) performed better (c-index-0.70 [0.66-0.74]), and, in practice, stage is a parameter that needs to be accounted for (FIGS. 2A to 2D). FIGS. 3A and 3B show the probability of relapse-free survival at 5 years plotted as a continuous linear scale using the full model.

The PAM50 classifier, assayed by qRT-PCR, was applied to a heterogeneously treated cohort archived between 1976 and 1995. The subtype classifications followed the same survival trends as seen in the microarray data and the ROR score was significant for long-term relapse predictions. This old age sample set was also scored for standard clinical markers (ER and HER2) by immunohistochemistry (IHC) and compared to the gene expression-based test. Analysis of ESR1 and ERBB2 by gene expression showed high sensitivity and specificity as compared to the IHC assay.

Discussion

The PAM50 classifier was developed using a statistically derived gene and sample set and was validated across multiple cohorts and platforms with the intent of delivering a clinical diagnostic test for the intrinsic subtypes of breast cancer. The large and diverse test sets allowed evaluation of the performance of the assay at a population level and in relation to standard molecular markers. An important finding from these analyses is that all of the intrinsic subtypes are present within both clinically defined ER-positive and ER-negative tumor subsets, with the subtype designations in the ER-positive patients showing prognostic significance. Thus, the molecular subtypes are not simply another method of classification based upon ER status.

There were also other important findings concerning individual subtypes. For example, some of the tumors classified into the HER2-enriched expression subtype were not HER2+clin, suggesting the presence of an ER-negative non-Basal subtype that is not driven by HER2 gene amplification. It was also found that about 10% of breast cancers were classified as Normal-like and can be either ER-positive or ER-negative and have an intermediate prognosis. Since these tumors were predicted by training on normal breast tissue, the Normal-like class may be an artifact of having a high percentage of normal "contamination" in the tumor specimen. Other possibilities are that these are slow growing Basal-like tumors that lack high expression of the proliferation genes, or are a potential new subtype that has been referred to as claudin-low tumors (25). Detailed histological, immunohistochemical, and additional gene expression analyses of these cases are needed to resolve these issues.

Discrepancies between subtype and standard molecular markers have important therapeutic implications. For instance, a patient with a Basal-like subtype tumor that was scored ER or PgR-positive would likely be treated by endocrine therapy and would not be eligible for protocols that aim to develop Basal-like specific therapies (e.g., platinum containing regimens). These analyses of the Hess et al. dataset (19) showed that no patient with the LumA subtype had a pCR when administered an aggressive neoadjuvant regimen whereas the pCR rate of the Basal-like tumors was 59%. Furthermore, there has been debate about whether the triple-negative (ER−, PR−, HER2−) phenotype is the same as the Basal-like expression subtype26. A recent tissue microarray study of 3744 tumors confirmed the poor prognosis of triple-negative cases, but also revealed that tumors lacking all markers did not behave the same as those that were positive for one or two Basal-like markers (i.e., CK5/6 or HER1) (27). In agreement with the idea that the Basal-like diagnosis should be made independent of clinical ER and PgR status, a higher therapeutic response to T/FAC was found in those subjects identified as Basal-like but non-triple negative (50%) versus those identified as triple-negative but not Basal-like (22%). This suggests that the Basal-like subtype designation may ultimately prove superior to the triple-negative definition in identifying tumors with a high degree of chemotherapy sensitivity.

Providing an absolute subtype classification is somewhat artificial as tumors do not exist as discrete biological entities. Classification of tumors into low-medium-high risk groups based upon distance to each subtype centroid (i.e., the ROR model) was an attempt to deal with this issue and yielded significant survival segregation. This was true when combining all test cases, or after stratification into cohorts given endocrine therapy only, or no systemic adjuvant treatment. One of the major benefits of the ROR predictor is the identification of LumA patients that are at a very low risk of relapse, and for whom the benefit from adjuvant chemotherapy is unlikely. In this context the ROR predictor based on subtypes provides similar information as the OncotypeDx Recurrence Score for ER-positive, node negative patients (4, 5). However the PAM50 based assay provides a risk of relapse score for all patients, including those with ER-negative disease.

In summary, this subtype predictor and ROR classifier effectively identifies molecular features in breast tumors that are important for prognosis and treatment. The qRT-PCR assay can be performed using archived breast tissues, which will be useful for retrospective studies and prospective clinical trials.

TABLE 2

Clinical and Subtype Data for Prototype samples from Microarray/
qRT-PCR Training Sets

| Patient ID | GEO accession | Subtype Assignment (SigClust) | qPCR_name | Dx Age | Ethnicity | pT* | pN^ | M | Grade% | Overall Survival | Vital Status | ER (IHC)** | PR (IHC)** | HER2 (status)^^ |
|---|---|---|---|---|---|---|---|---|---|---|---|---|---|---|
| 1 | GSM275694 | Basal-like | BR000161BPE_UU | NA | NA | NA | NA | NA | NA | NA | NA | NA | NA | NA |
| 3 | GSM140985 | Basal-like | BR000572BPE_UU | 45 | AA | 3 | 0 | 0 | 3 | NA | NA | 0 | 0 | NA |
| 7 | GSM140999 | Basal-like | BR010235BPE_UU | 36 | AA | 1 | 0 | 0 | 3 | 49 | 0 | 0 | 0 | 0 |
| 10 | GSM275782 | Basal-like | BR010532BPE_UU | 47 | AA | 3 | 1 | 0 | 3 | 14 | 1 | 0 | 0 | 0 |
| 11 | GSM80221 | Basal-like | BR020018BPE_UU | 55 | C | 2 | 0 | 0 | 3 | 31 | 0 | 0 | 0 | 0 |
| 12 | GSM141096 | HER2-enriched | BR020155BPE_UU | 38 | NA | 3 | 1 | 0 | 3 | 42 | 0 | 0 | 0 | 1 |
| 13 | GSM141099 | HER2-enriched | BR020306BPE_UU | 42 | C | 4 | 2 | 1 | 3 | 22 | 1 | 1 | 1 | 1 |
| 14 | GSM141102 | LumB | BR020439BPE_UU | 53 | C | 4 | 1 | 1 | 3 | 16 | 1 | 1 | 0 | 0 |

TABLE 2-continued

Clinical and Subtype Data for Prototype samples from Microarray/
qRT-PCR Training Sets

| Pa-tient ID | GEO accession | Subtype Assign-ment (SigClust) | qPCR_name | Dx Age | Eth-nicity | pT* | pN^ | M | Grade% | Over-all Sur-vival | Vital Status | ER (IHC)** | PR (IHC)** | HER2 (status)^^ |
|---|---|---|---|---|---|---|---|---|---|---|---|---|---|---|
| 15 | GSM275783 | LumA | BR020464BPE_UU | 44 | C | 2 | 0 | 0 | 1 | 2 | 0 | 1 | 1 | 0 |
| 16 | GSM141105 | Basal-like | BR020578BPE_UU | 76 | AA | 4 | 0 | 0 | 3 | 5 | 1 | 0 | 0 | 1 |
| 18 | GSM141110 | Basal-like | BR030459BPE_UU | 30 | C | 3 | 0 | 0 | 3 | 37 | 0 | 0 | 0 | 0 |
| 19 | GSM275771 | LumA | BR030584BPE_UU | 54 | C | 1 | 1 | NA | NA | NA | 0 | 1 | 1 | 0 |
| 21 | GSM141114 | LumB | BR040114BPE_UU | 56 | C | 2 | 0 | 0 | 2 | 16 | 0 | 1 | 1 | 0 |
| 22 | GSM141117 | LumB | BR040182BPE_UU | 88 | C | 2 | 1 | 0 | 3 | 16 | 0 | 1 | 1 | 1 |
| 23 | GSM141121 | HER2-enriched | BR040269BPE_UU | 46 | C | 2 | 0 | 0 | 3 | 17 | 0 | 0 | 0 | 1 |
| 28 | GSM34523 | Basal-like | PB00205PE_UU | 39 | C | NA | NA | 1 | 3 | 5 | 1 | 0 | 0 | 0 |
| 29 | GSM52895 | LumA | PB00284PE_UU | 34 | C | 1 | 0 | 0 | 1 | 54 | 0 | 1 | 1 | 0 |
| 30 | GSM34565 | Basal-like | PB00297PE_UU | 55 | AA | 2 | 0 | 0 | 3 | 55 | 0 | 0 | 0 | 0 |
| 31 | GSM34481 | HER2-enriched | PB00311PE_UU | 47 | C | 2 | 1 | 0 | 3 | 50 | 0 | 1 | 1 | 0 |
| 32 | GSM34497 | HER2-enriched | PB00314PE_UU | 50 | C | 3 | 1 | 0 | 3 | 52 | 0 | 0 | 0 | 1 |
| 33 | GSM34527 | Basal-like | PB00334PE_UU | 50 | AA | 1 | 0 | 0 | 3 | 54 | 0 | 0 | 0 | 0 |
| 35 | GSM34544 | HER2-enriched | PB00376PE_UU | 50 | AA | 2 | 0 | 0 | 3 | 49 | 0 | 0 | 0 | 0 |
| 37 | GSM34549 | LumA | PB00441PE_UU | 83 | C | 1 | 0 | 0 | 2 | 14 | 0 | 1 | 1 | 0 |
| 38 | GSM34528 | HER2-enriched | PB00455PE_UU | 52 | AA | 3 | 1 | 0 | 2 | 46 | 0 | 0 | 0 | 1 |
| 39 | GSM52884 | LumA | PB00479PE_UU | 50 | NA | 2 | 0 | 0 | NA | NA | 0 | 1 | 1 | 0 |
| 41 | GSM50157 | Basal-like | UB00028PE_UU | 46 | C | 1 | 0 | 0 | 3 | 59 | 0 | 0 | 0 | 0 |
| 42 | GSM34437 | Basal-like | UB00029PE_UU | 59 | C | 2 | 0 | 0 | 3 | 59 | 0 | 0 | 0 | 0 |
| 43 | GSM34431 | HER2-enriched | UB00037PE_UU | 42 | C | 1 | 1 | 0 | 3 | 58 | 0 | 0 | 1 | 0 |
| 44 | GSM34548 | LumA | UB00038PE_UU | 50 | C | 1 | 0 | 0 | 2 | 57 | 0 | 1 | 1 | 0 |
| 47 | GSM34428 | LumA | UB00044PE_UU | 49 | C | 2 | 1 | 0 | 2 | 59 | 0 | 1 | 1 | 0 |
| 50 | GSM34557 | LumA | UB00056PE_UU | 63 | C | 1 | 1 | 0 | 2 | 56 | 0 | 1 | 1 | 0 |
| 53 | GSM34532 | HER2-enriched | UB00060PE_UU | 72 | C | 3 | 3 | 0 | 3 | 49 | 0 | 0 | 0 | 1 |
| 56 | GSM34450 | Basal-like | UB00067PE_UU | 80 | C | 1 | 1 | 0 | 3 | 38 | 1 | 0 | 0 | 0 |
| 57 | GSM34451 | LumA | UB00069PE_UU | 40 | C | 1 | 0 | 0 | 2 | 7 | 0 | NA | NA | 0 |
| 58 | GSM34452 | Basal-like | UB00071PE_UU | 60 | C | 1 | 0 | 0 | 3 | 50 | 0 | 0 | 0 | 0 |
| 60 | GSM141079 | LumA | UB00081LPE_UU | 65 | C | NA | 1 | 0 | 2 | 44 | 0 | 1 | 1 | 0 |
| 61 | GSM141081 | LumA | UB00082PE_UU | 43 | C | 1 | 1 | 0 | 1 | 40 | 0 | 1 | 1 | 0 |
| 63 | GSM141084 | LumB | UB00088PE_UU | 69 | C | 2 | 2 | 0 | 2 | 38 | 1 | 1 | 1 | 1 |
| 64 | GSM141085 | LumA | UB00091PE_UU | 77 | C | 1 | 0 | 0 | 2 | 36 | 0 | 1 | 1 | 0 |
| 65 | GSM141088 | LumA | UB00099PE_UU | 50 | C | 3 | 1 | 0 | 2 | 35 | 0 | 1 | 1 | 0 |
| 66 | GSM141070 | Basal-like | UB00100PE_UU | 49 | C | 1 | 0 | 0 | 3 | 34 | 0 | NA | NA | 0 |
| 67 | GSM141071 | Basal-like | UB00110PE_UU | 76 | C | 2 | 0 | 0 | 3 | 31 | 0 | 0 | 0 | 0 |
| 68 | GSM141072 | Basal-like | UB00116PE_UU | 67 | C | 2 | 0 | NA | 3 | 34 | 0 | 0 | 0 | 1 |
| 69 | GSM141073 | HER2-enriched | UB00117PE_UU | 72 | other | NA | 0 | 0 | 3 | 31 | 0 | 0 | 0 | 1 |
| 72 | GSM275802 | Basal-like | WU00328-16563PE_UU | 59 | C | 2 | 0 | 0 | 3 | 82 | 0 | 0 | 0 | 0 |
| 73 | GSM275803 | HER2-enriched | WU00431-16439PE_UU | 73 | C | 4 | 1 | 0 | 3 | 44 | 1 | 0 | 0 | 1 |
| 74 | GSM275800 | HER2-enriched | WU00441-19793PE_UU | 49 | C | 3 | 1 | 0 | 2 | 27 | 1 | 1 | 1 | 1 |
| 75 | GSM275804 | LumA | WU00509-19794PE_UU | 57 | C | 2 | 1 | 0 | 3 | 51 | 0 | 0 | 0 | 0 |
| 76 | GSM275805 | HER2-enriched | WU00531-19795PE_UU | 75 | C | 2 | 0 | 0 | 1 | 81 | 0 | 1 | 0 | 0 |
| 78 | GSM275807 | LumB | WU00556-21032PE_UU | 46 | C | 2 | 1 | 0 | 2 | 88 | 0 | 1 | 1 | 0 |
| 82 | GSM275810 | Basal-like | WU00899-18760PE_UU | 47 | AA | 2 | 0 | 0 | 3 | 83 | 0 | 1 | 1 | 0 |
| 86 | GSM275813 | Basal-like | WU01407-16456PE_UU | 39 | AA | 2 | 0 | 0 | 3 | 80 | 0 | 0 | 0 | 0 |
| 88 | GSM275815 | HER2-enriched | WU01500-18755PE_UU | 88 | C | 1 | 0 | 0 | 3 | 70 | 0 | 1 | 0 | 0 |
| 89 | GSM275816 | HER2-enriched | WU01502-16455PE_UU | 74 | C | 2 | 2 | 0 | 3 | 88 | 0 | 1 | 0 | 0 |
| 90 | GSM275817 | HER2-enriched | WU01511-19773PE_UU | 50 | AA | 1 | 1 | 0 | 3 | 82 | 0 | 0 | 0 | 1 |
| 91 | GSM275818 | LumA | WU01520-21957PE_UU | 58 | C | 2 | 1 | 0 | 2 | 77 | NA | 1 | 1 | NA |
| 92 | GSM275819 | HER2-enriched | WU01540-14690PE_UU | 46 | C | 3 | 1 | 0 | 3 | 20 | 1 | NA | NA | 0 |
| 93 | GSM275799 | LumB | WU01576-19797PE_UU | 64 | O | 2 | 1 | 0 | 3 | 56 | 0 | 1 | 1 | 0 |

TABLE 2-continued

Clinical and Subtype Data for Prototype samples from Microarray/
qRT-PCR Training Sets

| Patient ID | GEO accession | Subtype Assignment (SigClust) | qPCR_ name | Dx Age | Eth- nicity | pT* | pN^ | M | Grade% | Over- all Sur- vival | Vital Status | ER (IHC)** | PR (IHC)** | HER2 (status)^^ |
|---|---|---|---|---|---|---|---|---|---|---|---|---|---|---|
| 95 | GSM275821 | LumB | WU01587-16348PE_UU | 72 | C | 1 | 0 | 1 | 2 | 82 | 0 | 1 | 0 | 0 |
| 96 | GSM275822 | LumB | WU01613-16349PE_UU | 78 | C | 2 | 2 | 0 | 3 | 17 | 0 | 1 | 1 | 0 |
| 97 | GSM275823 | Basal-like | WU01680-16347PE_UU | 47 | C | 2 | 0 | 0 | 3 | 77 | 0 | 0 | 0 | 1 |
| 99 | GSM275825 | Basal-like | WU01790-16344PE_UU | 32 | AA | 3 | 1 | 0 | 3 | 15 | 0 | 0 | 0 | 1 |
| 101 | GSM275792 | Basal-like | WU01887-16342PE_UU | 73 | AA | 2 | 0 | 0 | 3 | 78 | 0 | 0 | 1 | 0 |
| 104 | GSM275829 | Basal-like | WU02104-16341PE_UU | 57 | C | 2 | 1 | 0 | 3 | 51 | 0 | 0 | 0 | 0 |
| 105 | GSM275830 | Basal-like | WU02132-18761PE_UU | 57 | C | 3 | 1 | 0 | 3 | 76 | 0 | 0 | 0 | 0 |
| 107 | GSM275832 | HER2-enriched | WU02338-21961PE_UU | 42 | C | 2 | 1 | 0 | 3 | 59 | 1 | 1 | 1 | 1 |
| 108 | GSM275833 | Basal-like | WU02390-16330PE_UU | 46 | C | 2 | 0 | 1 | 3 | 9 | 1 | 0 | 0 | 0 |
| 109 | GSM275834 | Basal-like | WU02455-14693PE_UU | 44 | C | 3 | 0 | 0 | 3 | 15 | 1 | 0 | 0 | 0 |
| 110 | GSM275797 | HER2-enriched | WU02468-21279PE_UU | 63 | AA | 1 | 2 | 0 | 3 | 72 | 0 | NA | NA | 1 |
| 113 | GSM275795 | HER2-enriched | WU02769-16337PE_UU | 73 | C | 1 | 0 | 0 | 2 | 69 | 0 | 1 | 0 | 1 |
| 114 | GSM275837 | Basal-like | WU02771-14694PE_UU | 43 | C | 3 | 0 | 0 | 3 | 16 | 1 | 0 | 0 | 1 |
| 116 | GSM275839 | Basal-like | WU02843-19762PE_UU | 46 | C | 1 | 0 | 0 | 3 | 75 | 0 | 0 | 0 | 1 |
| 118 | GSM275841 | Basal-like | WU02948-16566PE_UU | 44 | C | 1 | 0 | 0 | 3 | 62 | 0 | 0 | 0 | 0 |
| 120 | GSM275842 | HER2-enriched | WU03064-16462PE_UU | 74 | AA | 2 | 0 | 0 | 3 | 70 | 0 | 1 | 1 | 1 |
| 121 | GSM275843 | Basal-like | WU03292-16446PE_UU | 50 | AA | 3 | 0 | 0 | 3 | 79 | 0 | 0 | 0 | 0 |
| 123 | GSM275791 | HER2-enriched | WU03456-16361PE_UU | 52 | AA | 1 | 0 | 0 | 3 | 67 | 0 | 1 | 1 | 0 |
| 125 | GSM275846 | LumB | WU0353-16451PE_UU | 82 | C | 2 | 0 | 0 | 3 | 60 | 0 | 1 | 1 | 0 |
| 126 | GSM275796 | HER2-enriched | WU03653-16448PE_UU | 49 | C | 1 | 2 | 0 | 3 | 102 | 0 | 0 | 0 | 1 |
| 127 | GSM275847 | Basal-like | WU03661-16447PE_UU | 53 | AA | 4 | 1 | 0 | 3 | 3 | 1 | 1 | 1 | 0 |
| 128 | GSM275788 | LumA | WU03662-16452PE_UU | 75 | AA | 2 | 0 | 0 | 3 | 45 | 0 | 0 | 0 | 0 |
| 129 | GSM275848 | Basal-like | WU03685-16502PE_UU | 42 | AA | 2 | 0 | 0 | 3 | 65 | 0 | 0 | 0 | 0 |
| 131 | GSM275850 | Basal-like | WU03714-21262PE_UU | 66 | AA | 1 | 0 | 0 | 3 | 72 | 0 | 1 | 1 | 0 |
| 132 | GSM275793 | HER2-enriched | WU03721-16570PE_UU | 29 | C | 2 | 1 | 0 | 3 | 13 | 0 | 1 | 0 | 1 |
| 134 | GSM275852 | Basal-like | WU03791-16497PE_UU | 61 | C | 1 | 1 | 0 | 3 | 62 | 0 | 0 | 0 | 0 |
| 135 | GSM275853 | Basal-like | WU03831-21959PE_UU | 51 | AA | 2 | 1 | 0 | 3 | 68 | 0 | 0 | 0 | 1 |
| 139 | GSM275857 | Basal-like | WU03885-16469PE_UU | 52 | AA | 2 | 1 | 0 | 3 | 26 | 1 | 1 | 1 | 0 |
| 140 | GSM275858 | HER2-enriched | WU03946-14842PE_UU | 72 | C | 2 | 1 | 0 | 2 | 15 | NA | 0 | 1 | 1 |
| 141 | GSM275789 | Basal-like | WU04000-16466PE_UU | 49 | AA | 1 | 2 | 0 | 3 | 24 | 1 | NA | NA | 0 |
| 144 | GSM275861 | HER2-enriched | WU04038-16465PE_UU | 51 | AA | 2 | 1 | 0 | 2 | 62 | 0 | 1 | 1 | 1 |
| 146 | GSM275863 | Basal-like | WU04327-19803PE_UU | 73 | C | 1 | 0 | 0 | 2 | 69 | 0 | 1 | 0 | 1 |
| 147 | GSM275864 | LumB | WU04532-16463PE_UU | 75 | AA | 2 | 1 | 0 | 3 | 53 | 0 | 1 | 0 | 1 |
| 148 | GSM275864 | Basal-like | WU04834-16461PE_UU | 42 | AA | 2 | 0 | 0 | 3 | 65 | 0 | 0 | 0 | 0 |
| 149 | GSM275866 | Basal-like | WU04952-19753PE_UU | 64 | AA | 2 | 1 | 0 | 3 | 62 | 0 | 0 | 0 | 0 |
| 152 | GSM275872 | LumA | WU05094-16580PE_UU | 29 | C | 1 | 1 | 0 | 1 | 60 | 0 | 1 | 1 | 0 |

TABLE 2-continued

Clinical and Subtype Data for Prototype samples from Microarray/
qRT-PCR Training Sets

| Patient ID | GEO accession | Subtype Assignment (SigClust) | qPCR_ name | Dx Age | Ethnicity | pT* | pN^ | M | Grade% | Overall Survival | Vital Status | ER (IHC)** | PR (IHC)** | HER2 (status)^^ |
|---|---|---|---|---|---|---|---|---|---|---|---|---|---|---|
| 153 | GSM275873 | HER2-enriched | WU05118-19759PE_UU | 54 | C | 1 | 0 | 0 | 3 | 64 | 0 | 1 | 0 | 1 |
| 155 | GSM275875 | HER2-enriched | WU05162-21960PE_UU | 43 | C | 2 | 0 | 0 | 3 | 95 | 1 | NA | NA | NA |
| 156 | GSM275876 | Basal-like | WU05191-14791PE_UU | 51 | AA | 4 | 1 | 1 | 2 | 46 | 1 | NA | NA | 1 |
| 157 | GSM275877 | HER2-enriched | WU05196-16573PE_UU | 59 | C | 1 | 0 | 0 | 2 | 56 | 0 | 0 | 0 | 0 |
| 158 | GSM275878 | HER2-enriched | WU05207-16473PE_UU | 72 | AA | 4 | 1 | 0 | 3 | 59 | 0 | 1 | 0 | 1 |
| 159 | GSM275879 | Basal-like | WU05125-16503PE_UU | 79 | AA | 2 | 0 | 0 | 3 | 48 | 0 | 0 | 0 | 0 |
| 160 | GSM275880 | HER2-enriched | WU05337-14835PE_UU | 51 | C | 2 | 1 | 0 | 3 | 14 | 1 | 0 | 0 | 0 |
| 161 | GSM275881 | HER2-enriched | WU05415-16357PE_UU | 52 | C | 2 | 0 | 0 | 3 | 48 | 0 | 1 | 1 | 0 |
| 163 | GSM275883 | Basal-like | WU05478-16356PE_UU | 41 | C | 2 | 0 | 0 | 3 | 54 | 0 | 0 | 0 | 0 |
| 165 | GSM275885 | Basal-like | WU05641-16354PE_UU | 40 | AA | 2 | 0 | 0 | 3 | 54 | 0 | 0 | 0 | 0 |
| 167 | GSM275887 | Basal-like | WU05991-14687PE_UU | 70 | AA | 4 | 1 | 0 | 3 | 19 | 1 | 0 | 0 | 0 |
| 168 | GSM275888 | Basal-like | WU06036-16352PE_UU | 42 | AA | 2 | 0 | 0 | 3 | 50 | 0 | 0 | 0 | NA |
| 169 | GSM275889 | Basal-like | WU06397-19805PE_UU | 64 | C | 2 | 0 | 0 | 3 | 54 | 0 | 0 | 0 | 0 |
| 170 | GSM275890 | HER2-enriched | WU06398-19767PE_UU | 34 | C | 1 | 1 | 0 | 3 | 4 | 0 | 1 | 1 | 1 |
| 171 | GSM275891 | HER2-enriched | WU06416-19781PE_UU | 74 | C | 1 | 0 | 0 | 3 | 51 | 0 | 0 | 0 | 0 |
| 172 | GSM275892 | LumA | WU06545-18758PE_UU | 69 | C | 3 | 0 | 0 | 3 | 49 | 0 | 1 | 1 | 0 |
| 173 | GSM275893 | HER2-enriched | WU0659-14689PE_UU | 42 | AA | 4 | 2 | 0 | 3 | 35 | 1 | 0 | 0 | 0 |
| 174 | GSM275894 | Basal-like | WU06580-16575PE_UU | 44 | AA | 2 | 0 | 0 | 3 | 48 | 0 | 0 | 0 | 0 |
| 175 | GSM275895 | LumB | WU06611-16475PE_UU | 46 | C | 2 | 0 | 0 | 3 | 51 | 0 | 1 | 1 | 1 |
| 177 | GSM275897 | Basal-like | WU06857-15260PE_UU | 40 | AA | 2 | 1 | 0 | 3 | 11 | 1 | 0 | 0 | 0 |
| 178 | GSM275898 | LumA | WU07407-19770PE_UU | 66 | C | 2 | 1 | 0 | 3 | 5 | 0 | 1 | 1 | 0 |
| 180 | GSM275900 | LumA | WU07509-19782PE_UU | 57 | AA | 1 | 1 | 0 | 2 | 22 | 0 | 1 | 1 | 0 |
| 182 | GSM275902 | LumA | WU07512-14793PE_UU | 83 | C | 1 | NA | 0 | 2 | 21 | 0 | 1 | 1 | 0 |
| 184 | GSM275904 | Basal-like | WU07558-16584PE_UU | 41 | AA | 1 | 0 | 0 | 3 | 29 | 0 | 0 | 0 | 0 |
| 185 | GSM275905 | Basal-like | WU07589-16582PE_UU | 70 | AA | 2 | 1 | 0 | 3 | 19 | 0 | 0 | 0 | 0 |
| 187 | GSM275907 | LumA | WU07791-19784PE_UU | 78 | C | 1 | 0 | 0 | 2 | 53 | 0 | 1 | 1 | 1 |
| 188 | GSM275908 | LumA | WU07805-19777PE_UU | 41 | C | 2 | 1 | 0 | 3 | 58 | 0 | 1 | 1 | 0 |
| 189 | GSM275909 | Basal-like | WU08626-1656PE_UU | 34 | AA | 4 | 1 | 0 | 3 | 37 | 0 | 0 | 0 | 0 |
| 190 | GSM34464 | Basal-like | NA | 61 | NA | 2 | 1 | 0 | 3 | 13 | 1 | 0 | NA | NA |
| 191 | GSM140992 | Basal-like | NA | 29 | NA | 2 | 2 | 0 | 3 | NA | 1 | 0 | NA | NA |
| 192 | GSM50148 | Basal-like | NA | 51 | C | 4 | 2 | 0 | NA | 74 | 1 | 0 | NA | NA |
| 193 | GSM34562 | Basal-like | NA | 50 | C | 1 | 0 | 0 | 3 | 29 | 0 | 1 | 0 | 1 |
| 194 | GSM52896 | LumB | NA | 79 | NA | 2 | 2 | 0 | 3 | 15 | 0 | 1 | NA | 1 |
| 195 | GSM141067 | Normal-like | NA | NA | NA | NA | NA | NA | NA | NA | NA | NA | NA | NA |
| 196 | GSM80240 | Normal-like | NA | NA | NA | NA | NA | NA | NA | NA | NA | NA | NA | NA |
| 197 | GSM34547 | Normal-like | NA | NA | NA | NA | NA | NA | NA | NA | NA | NA | NA | NA |
| 198 | GSM34483 | Normal-like | NA | NA | NA | NA | NA | NA | NA | NA | NA | NA | NA | NA |
| 199 | GSM34482 | Normal-like | NA | NA | NA | VN | NA | NA | NA | NA | NA | NA | NA | NA |
| 200 | GSM140990 | Normal-like | NA | NA | NA | NA | NA | NA | NA | NA | NA | NA | NA | NA |
| 201 | GSM140991 | Normal-like | NA | NA | NA | NA | NA | NA | NA | NA | NA | NA | NA | NA |
| 202 | GSM275777 | Normal-like | NA | NA | NA | NA | NA | NA | NA | NA | NA | NA | NA | NA |
| 203 | GSM275778 | Normal-like | NA | NA | NA | NA | NA | NA | NA | NA | NA | NA | NA | NA |

TABLE 2-continued

Clinical and Subtype Data for Prototype samples from Microarray/
qRT-PCR Training Sets

| Patient ID | GEO accession | Subtype Assignment (SigClust) | qPCR_ name | Dx Age | Eth-nicity | pT* | pN^ | M | Grade% | Overall Survival | Vital Status | ER (IHC)** | PR (IHC)** | HER2 (status)^^ |
|---|---|---|---|---|---|---|---|---|---|---|---|---|---|---|
| 204 | GSM275781 | Normal-like | NA | NA | NA | NA | NA | NA | NA | NA | NA | NA | NA | NA |
| 205 | GSM275780 | Normal-like | NA | NA | NA | NA | NA | NA | NA | NA | NA | NA | NA | NA |
| 206 | GSM275779 | Normal-like | NA | NA | NA | NA | NA | NA | NA | NA | NA | NA | NA | NA |

*pathologic tumor stage: T1 ≤ 2 cm, T2 > 2 cm-5 cm, T3 > 5 cm, NA = not assessed
^patholgic node stage: N0 = no positive nodes, N1 = positive axillary nodes, NA = not assessed
%histological grade: 0 grades 1&2, 1 = grade 3
**immunohistochemistry: 0 = no to moderate staining, 1 = strong staining in majority of cancer cells
^^immunohistochemistry and fluorescence in-situ hybridization: 0 = negative by IHC (0, 1) or 2+ by IHC and negative by FISH, 1 = 3+ by IHC or 2+ by IHC and positive by FISH

TABLE 3

Clinical and Subtype Data for qRT-PCR Test Set

| Patient ID | Subtype Prediction | pT* | pN^ | Grade% | Overall Survival | Relapse Free Survival | Any Relapse*** | DSS** | ER (IHC)^^ | PR (IHC)^^ | Her2 (IHC)^^ |
|---|---|---|---|---|---|---|---|---|---|---|---|
| 1001 | LumB | 2 | 1 | 1 | 2.3232877 | 0.690411 | 1 | 1 | 1 | 1 | 0 |
| 1002 | Her2-enriched | 2 | NA | 1 | 19.512329 | 2.9753425 | 1 | 1 | 0 | 0 | 0 |
| 1003 | Her2-enriched | 1 | 1 | 1 | 7.0410959 | 5.4 | 1 | 1 | 0 | NA | 1 |
| 1004 | LumB | 2 | 0 | 0 | NA | NA | NA | 1 | 1 | 1 | 0 |
| 1005 | Her2-enriched | 1 | 0 | 0 | 0.939726 | 0.3671233 | 1 | 1 | 0 | NA | NA |
| 1006 | LumB | 2 | 1 | 0 | 0.7178082 | 0.5178082 | 1 | 2 | 1 | 1 | 0 |
| 1007 | LumB | NA | NA | 0 | 3.3287671 | 1.7616438 | 1 | 1 | 1 | 1 | 0 |
| 1008 | Her2-enriched | 2 | NA | 0 | 0.8849315 | 0.7068493 | 1 | 1 | 1 | 0 | 0 |
| 1009 | Basal-like | 3 | 1 | 0 | 5.9917808 | 0.8246575 | 1 | 1 | 0 | 0 | 0 |
| 1010 | LumA | 2 | 1 | NA | 12.273973 | 9.0712329 | 1 | 1 | 1 | 1 | NA |
| 1011 | Her2-enriched | 2 | 1 | 1 | 3.2027397 | 1.2493151 | 1 | 1 | 0 | 0 | 1 |
| 1012 | Normal-like | 1 | 1 | 0 | 25.435616 | 22.709589 | 1 | 1 | 1 | 1 | 0 |
| 1013 | LumB | 2 | 1 | 0 | NA | NA | NA | 1 | 1 | 0 | 0 |
| 1014 | LumB | 2 | 0 | 0 | 16.654795 | 16.654795 | 0 | 2 | 1 | 1 | 0 |
| 1015 | LumA | 2 | 0 | 0 | 4.5150685 | 3.8821918 | 1 | 1 | 1 | 0 | 0 |
| 1016 | Basal-like | 2 | 0 | 1 | 2.0383562 | 1.6712329 | 1 | 1 | 0 | 0 | 0 |
| 1017 | LumA | 2 | 1 | 0 | 10.331507 | 5.9315068 | 1 | 1 | 1 | 0 | 0 |
| 1018 | LumB | 2 | 0 | 0 | 22.230137 | 21.89589 | 1 | 1 | 1 | 1 | 0 |
| 1019 | LumB | 2 | 1 | 0 | 3.0931507 | 1.4520548 | 1 | 1 | 1 | 1 | 0 |
| 1020 | LumA | 2 | 1 | 0 | 4.8630137 | 4.8630137 | 0 | 2 | 1 | 1 | 0 |
| 1021 | LumA | 1 | 0 | 0 | 6.7972603 | 4.9671233 | 1 | 2 | 1 | 1 | 0 |
| 1022 | LumB | 2 | 1 | 0 | 3.9150685 | 1.4164384 | 1 | 1 | 1 | 0 | 0 |
| 1023 | LumA | 2 | 1 | 0 | 25.945205 | 25.945205 | 0 | 3 | 1 | 1 | 0 |
| 1024 | Basal-like | 3 | NA | 1 | 2.4438356 | 1.7753425 | 1 | 1 | 0 | 0 | 0 |
| 1025 | LumA | 1 | 1 | 0 | 2.8767123 | 0.0027397 | 1 | 1 | 1 | 0 | 1 |
| 1026 | LumA | 1 | NA | 0 | 8.0821918 | 8.0821918 | 0 | 2 | 1 | 1 | 0 |
| 1027 | LumB | 1 | 1 | 0 | 25.778082 | 25.778082 | 0 | 3 | 1 | 1 | 0 |
| 1028 | LumA | 2 | 1 | 0 | 9.2520548 | 8.9753425 | 1 | 1 | 1 | 1 | 0 |
| 1029 | Basal-like | 2 | 0 | 1 | 3.4410959 | 1.9726027 | 1 | 1 | 0 | 0 | 0 |
| 1030 | Her2-enriched | 2 | 1 | 0 | 2.9232877 | 1.709589 | 1 | 1 | 1 | 1 | 1 |
| 1031 | LumA | 1 | 1 | 0 | 2.9616438 | 2.8958904 | 1 | 1 | 1 | 0 | 0 |
| 1032 | LumA | 2 | 0 | 0 | 4.509589 | 0.8465753 | 1 | 1 | 1 | 1 | 0 |
| 1033 | LumB | 1 | NA | 1 | 10.312329 | 9.9780822 | 1 | 1 | NA | NA | NA |
| 1034 | LumB | 1 | 0 | 1 | 15.19726 | 15.19726 | 0 | 2 | 1 | 1 | 0 |
| 1035 | Basal-like | 1 | 1 | 1 | 25.339726 | 25.339726 | 0 | 3 | 1 | 1 | 0 |
| 1036 | LumA | 2 | 1 | 0 | 3.4465753 | 1.460274 | 1 | 1 | 1 | NA | 0 |
| 1037 | Basal-like | 1 | 0 | 0 | 11.958904 | 11.958904 | 0 | 2 | 0 | 0 | 0 |
| 1038 | Basal-like | 2 | 1 | 1 | 2.4849315 | 2.2082192 | 1 | 1 | 0 | NA | 0 |
| 1039 | LumA | 2 | NA | 0 | 8.539726 | 6.8136986 | 1 | 1 | 1 | 1 | 0 |
| 1040 | Basal-like | 2 | 0 | 0 | 25.090411 | 25.090411 | 0 | 3 | 0 | 0 | 0 |
| 1041 | LumA | 2 | 1 | 0 | 3.7369863 | 1.7643836 | 1 | 1 | NA | NA | 0 |
| 1042 | Basal-like | 1 | NA | 0 | 2.1780822 | 0.9561644 | 1 | 1 | 1 | 1 | 1 |
| 1043 | LumB | 2 | 1 | 0 | 2.5452055 | 0.5232877 | 1 | 1 | 1 | 1 | 0 |
| 1044 | LumA | 1 | 1 | 0 | 2.630137 | 0.7315068 | 1 | 1 | 1 | 1 | 0 |
| 1045 | Basal-like | 2 | 1 | 1 | 1.4109589 | 1.060274 | 1 | 1 | 0 | 0 | 0 |
| 1046 | Basal-like | 2 | 1 | 1 | 24.835616 | 24.835616 | 0 | 3 | 0 | 0 | 0 |
| 1047 | Basal-like | 2 | 0 | 1 | 14.873973 | 14.536986 | 1 | 1 | 0 | 0 | 0 |
| 1048 | Her2-enriched | 1 | 1 | 1 | 2.3917808 | 1.5506849 | 1 | 1 | 1 | 1 | 0 |
| 1049 | LumA | 2 | 1 | 0 | 19.339726 | 19.339726 | 0 | 2 | 1 | 0 | 0 |
| 1050 | LumB | 2 | 1 | 0 | 13.605479 | 13.605479 | 0 | 2 | 1 | 0 | NA |
| 1051 | LumB | 2 | 1 | 0 | 2.4191781 | 1.4520548 | 1 | 1 | 1 | 1 | 0 |
| 1052 | Basal-like | 2 | 1 | 0 | 12.073973 | 11.739726 | 1 | 1 | NA | NA | 0 |

TABLE 3-continued

Clinical and Subtype Data for qRT-PCR Test Set

| Patient ID | Subtype Prediction | pT* | pN^ | Grade^% | Overall Survival | Relapse Free Survival | Any Relapse*** | DSS** | ER (IHC)^^ | PR (IHC)^^ | Her2 (IHC)^^ |
|---|---|---|---|---|---|---|---|---|---|---|---|
| 1053 | Basal-like | 2 | 1 | 0 | 0.3506849 | 0.0027397 | 1 | 1 | 0 | 0 | 0 |
| 1054 | Basal-like | 1 | 0 | 1 | 24.449315 | 24.449315 | 0 | 3 | 0 | 0 | 0 |
| 1055 | LumB | 2 | 0 | 0 | 6.1589041 | 4.1643836 | 1 | 1 | 1 | 0 | 0 |
| 1056 | LumB | 2 | NA | 0 | 1.2575342 | 0.0109589 | 1 | 1 | 1 | 1 | 0 |
| 1057 | LumA | 2 | 0 | 0 | 7.7753425 | 5.6630137 | 1 | 1 | 1 | 1 | 0 |
| 1058 | Basal-like | 1 | 1 | 1 | 24.323288 | 24.323288 | 0 | 3 | 0 | NA | NA |
| 1059 | LumB | 2 | 1 | 0 | 5.9863014 | 5.0876712 | 1 | 1 | 1 | 1 | 0 |
| 1060 | LumB | 1 | 1 | 1 | 24.115068 | 24.115068 | 0 | 3 | 1 | 1 | 0 |
| 1061 | Basal-like | 2 | 1 | 1 | 4.7972603 | 4.7972603 | 0 | 2 | 0 | 0 | 0 |
| 1062 | Basal-like | 3 | 1 | 1 | 24.084932 | 24.084932 | 0 | 3 | 0 | 0 | 0 |
| 1063 | Basal-like | 2 | 0 | 0 | 24.019178 | 24.019178 | 0 | 3 | 1 | 0 | 0 |
| 1064 | Basal-like | 2 | 0 | 1 | 22.791781 | 22.791781 | 0 | 3 | 0 | NA | NA |
| 1065 | Her2-enriched | 2 | 0 | 0 | 9.5150685 | 9.5150685 | 0 | NA | 0 | 0 | 0 |
| 1066 | Basal-like | 1 | 0 | 1 | 20.945205 | 20.945205 | 0 | 3 | 0 | 0 | 0 |
| 1067 | Normal-like | 2 | 0 | 0 | 10.917808 | 10.917808 | 0 | 2 | NA | NA | 1 |
| 1068 | Her2-enriched | 2 | 0 | 0 | 6.7013699 | 2.9726027 | 1 | 1 | 0 | NA | 0 |
| 1069 | LumB | 3 | 0 | 0 | 11.912329 | 11.912329 | 0 | 2 | 1 | 1 | 0 |
| 1070 | LumB | 2 | 0 | 0 | 20.731507 | 17.008219 | 1 | 3 | 1 | 1 | 0 |
| 1071 | LumB | 1 | NA | 0 | 4.0191781 | 1.2493151 | 1 | 2 | 1 | 1 | 0 |
| 1072 | LumA | 2 | 1 | 0 | 12.441096 | 12.441096 | 0 | 2 | 1 | 1 | 0 |
| 1073 | Her2-enriched | 3 | 0 | 0 | 20.660274 | 20.660274 | 0 | 3 | NA | NA | 1 |
| 1074 | LumA | 1 | NA | 0 | 4.7835616 | 4.4465753 | 1 | 1 | 1 | 0 | 0 |
| 1075 | LumA | 2 | 0 | 0 | 2.7534247 | 2.4246575 | 1 | 1 | 1 | 1 | 0 |
| 1076 | LumA | 2 | 1 | 0 | 20.539726 | 20.539726 | 0 | 3 | 1 | NA | 0 |
| 1077 | LumA | 1 | 1 | 0 | 20.408219 | 12.328767 | 1 | 3 | 1 | 1 | 0 |
| 1078 | Normal-like | 2 | NA | 0 | 2.6630137 | 1.2493151 | 1 | 1 | 1 | NA | 0 |
| 1079 | Her2-enriched | 1 | 1 | 0 | NA | NA | NA | 1 | 0 | 0 | 1 |
| 1080 | Basal-like | 2 | 1 | 0 | NA | NA | NA | 3 | 1 | 1 | 0 |
| 1081 | Normal-like | 2 | 1 | 0 | NA | NA | NA | 1 | 1 | 1 | 0 |
| 1082 | Her2-enriched | 2 | 0 | 0 | NA | NA | NA | 1 | 1 | 1 | 1 |
| 1083 | LumB | 2 | 0 | 1 | NA | NA | NA | 2 | 1 | 1 | NA |
| 1084 | LumA | 1 | 0 | 0 | NA | NA | NA | 3 | NA | NA | 0 |
| 1085 | Basal-like | 3 | 0 | 0 | NA | NA | NA | 1 | 1 | 0 | 0 |
| 1086 | Basal-like | 1 | 0 | 0 | 19.969863 | 19.969863 | 0 | 3 | 0 | 0 | 0 |
| 1087 | Basal-like | 1 | 0 | 1 | 19.657534 | 19.657534 | 0 | 3 | 0 | 0 | 0 |
| 1088 | LumA | 1 | 0 | 0 | 16.238356 | 3.9616438 | 1 | 1 | 1 | 1 | 0 |
| 1089 | Her2-enriched | 2 | 0 | 1 | 19.506849 | 19.506849 | 0 | 3 | 1 | 1 | 1 |
| 1090 | LumA | 1 | 0 | 0 | 8.5945205 | 6.9041096 | 1 | 1 | 0 | 0 | 0 |
| 1091 | LumA | 1 | 0 | 0 | 19.432877 | 2.6082192 | 1 | 3 | 1 | 1 | 0 |
| 1092 | Basal-like | 1 | 0 | NA | 19.405479 | 19.405479 | 0 | 3 | 0 | NA | NA |
| 1093 | LumB | 2 | 0 | 0 | 19.408219 | 16.756164 | 1 | 3 | 1 | NA | 0 |
| 1094 | LumA | 1 | NA | 0 | 19.358904 | 19.358904 | 0 | 3 | 1 | 1 | 0 |
| 1095 | LumB | 2 | 0 | 0 | 19.353425 | 19.353425 | 0 | 3 | 1 | 0 | 0 |
| 1096 | LumA | 2 | 0 | 0 | 13.345205 | 13.345205 | 0 | 2 | 1 | 1 | 0 |
| 1097 | Her2-enriched | 2 | 0 | 0 | 8.3890411 | 5.290411 | 1 | 2 | 1 | 0 | 0 |
| 1098 | Her2-enriched | 1 | 0 | 0 | 6.5863014 | 3.8767123 | 1 | 1 | 0 | NA | 1 |
| 1099 | LumB | 2 | 0 | 1 | 3.7780822 | 3.4438356 | 1 | 1 | 1 | 0 | 1 |
| 1100 | Her2-enriched | 1 | 0 | 0 | 19.20274 | 19.20274 | 0 | 3 | 1 | 0 | 1 |
| 1101 | Basal-like | 2 | 0 | 1 | 19.186301 | 19.186301 | 0 | 3 | 0 | 0 | 1 |
| 1102 | Basal-like | 1 | 0 | 0 | 5.8410959 | 4.7589041 | 1 | 1 | 0 | NA | NA |
| 1103 | Basal-like | 1 | 0 | 0 | 17.734247 | 3.6876712 | 1 | 2 | 1 | NA | NA |
| 1104 | LumA | 2 | 0 | 1 | 9.7917808 | 9.7917808 | 0 | 2 | 1 | NA | 0 |
| 1105 | Basal-like | 1 | 0 | 1 | 19.106849 | 19.106849 | 0 | 3 | 0 | NA | 0 |
| 1106 | Basal-like | 2 | 0 | 1 | 19.09863 | 19.09863 | 0 | 3 | 0 | NA | NA |
| 1107 | LumA | 1 | 0 | 0 | 19.871233 | 19.871233 | 0 | 3 | 1 | 1 | 0 |
| 1108 | Basal-like | 1 | 0 | 1 | 19.808219 | 19.808219 | 0 | 3 | 1 | 0 | NA |
| 1109 | LumB | 2 | 0 | 0 | 19.791781 | 1.6794521 | 1 | 3 | 1 | 1 | 0 |
| 1110 | Her2-enriched | 2 | 0 | 0 | 16.778082 | 16.778082 | 0 | 2 | 1 | 0 | 0 |
| 1111 | LumA | 1 | 0 | 0 | 19.789041 | 19.789041 | 0 | 3 | 1 | 1 | 0 |
| 1112 | LumB | 2 | 0 | 0 | 3.5068493 | 3.3643836 | 1 | 1 | 1 | 1 | 0 |
| 1113 | LumB | 2 | 0 | 1 | 2.3150685 | 0.9369863 | 1 | 2 | 1 | 0 | 0 |
| 1114 | Basal-like | 2 | 0 | 1 | 3.3232877 | 3.3232877 | 1 | 1 | 0 | NA | 0 |
| 1115 | Her2-enriched | 2 | 0 | 1 | 19.986301 | 19.986301 | 0 | 3 | 1 | 1 | 0 |
| 1116 | Basal-like | 2 | 0 | 1 | NA | NA | NA | 2 | 0 | 0 | 0 |
| 1117 | Her2-enriched | 1 | 0 | 1 | 19.758904 | 19.758904 | 0 | 3 | 1 | NA | 1 |
| 1118 | LumB | 1 | 0 | 1 | 19.717808 | 19.717808 | 0 | 3 | 1 | 1 | 0 |
| 1119 | LumB | 1 | 0 | 0 | 4.4054795 | 2.460274 | 1 | 1 | 1 | NA | 0 |
| 1120 | LumB | 2 | 0 | 1 | 5.3342466 | 4.8794521 | 1 | 1 | 1 | 1 | 0 |
| 1121 | LumA | 1 | 0 | 0 | 11.531507 | 11.531507 | 0 | 2 | 1 | 1 | 0 |
| 1122 | Normal-like | 1 | 0 | 0 | 15.424658 | 14.824658 | 1 | 2 | NA | NA | NA |
| 1123 | LumB | 2 | 0 | 0 | 3.8876712 | 3.8794521 | 1 | 1 | 1 | 1 | NA |
| 1124 | Basal-like | 1 | 0 | 0 | 19.252055 | 19.252055 | 0 | 3 | 0 | 0 | 0 |
| 1125 | Normal-like | 1 | 0 | 0 | 19.205479 | 19.205479 | 0 | 3 | 1 | 1 | 0 |
| 1126 | LumB | 1 | 0 | 0 | 20.005479 | 20.005479 | 0 | 3 | 1 | 1 | 0 |

TABLE 3-continued

Clinical and Subtype Data for qRT-PCR Test Set

| Patient ID | Subtype Prediction | pT* | pN^ | Grade% | Overall Survival | Relapse Free Survival | Any Relapse*** | DSS** | ER (IHC)^^ | PR (IHC)^^ | Her2 (IHC)^^ |
|---|---|---|---|---|---|---|---|---|---|---|---|
| 1127 | LumA | 1 | 0 | 0 | 19.950685 | 19.950685 | 0 | 3 | 1 | NA | 0 |
| 1128 | Normal-like | 2 | 1 | 0 | 19.931507 | 2.2657534 | 1 | 3 | 1 | NA | 0 |
| 1129 | LumA | 1 | 0 | 0 | 19.849315 | 4.509589 | 1 | 3 | 1 | 1 | 0 |
| 1130 | Basal-like | NA | 0 | 1 | 8.0630137 | 8.0630137 | 0 | NA | 0 | NA | NA |
| 1131 | Basal-like | 2 | 1 | 1 | 1.030137 | 0.0520548 | 1 | 1 | 0 | 0 | 1 |
| 1132 | Normal-like | 1 | 0 | 0 | 19.608219 | 19.608219 | 0 | 3 | 1 | 1 | 0 |
| 1133 | Her2-enriched | 1 | 1 | 1 | 19.550685 | 19.550685 | 0 | 3 | 1 | 1 | 0 |
| 1134 | Basal-like | 2 | 1 | 0 | 2.0712329 | 1.230137 | 1 | 1 | NA | NA | NA |
| 1135 | LumA | 1 | 1 | 0 | 19.449315 | 19.449315 | 0 | 3 | 1 | 1 | 0 |
| 1136 | LumB | 1 | 1 | 0 | 5.0520548 | 4.4684932 | 1 | 1 | 1 | 1 | 0 |
| 1137 | LumA | 2 | 1 | 0 | 19.331507 | 17.657534 | 1 | 3 | 1 | 1 | 0 |
| 1138 | LumA | 1 | 1 | 0 | 19.331507 | 19.331507 | 0 | 3 | 1 | 1 | 0 |
| 1139 | Basal-like | 1 | 0 | 1 | 19.046575 | 19.046575 | 0 | 3 | NA | 0 | 0 |
| 1140 | Her2-enriched | 1 | 0 | 0 | 18.917808 | 18.917808 | 0 | 3 | 1 | 0 | 0 |
| 1141 | LumB | 3 | NA | 0 | 5.5205479 | 1.8410959 | 1 | 1 | 1 | 1 | 0 |
| 1142 | LumA | 1 | 0 | 0 | 18.649315 | 18.649315 | 0 | NA | 1 | NA | 0 |
| 1143 | LumA | 1 | 0 | 0 | 4.8876712 | 4.8876712 | 0 | 1 | 1 | 1 | 0 |
| 1144 | Basal-like | NA | 1 | 0 | 2.9972603 | 2.9123288 | 1 | 1 | NA | NA | 0 |
| 1145 | LumA | 1 | 0 | 0 | 18.753425 | 18.753425 | 0 | 3 | 1 | 1 | NA |
| 1146 | LumA | 3 | NA | 0 | 3.1917808 | 0.0027397 | 1 | 1 | 1 | 1 | 0 |
| 1147 | Basal-like | 1 | 0 | 1 | 10.79726 | 10.79726 | 0 | 2 | 1 | 0 | 0 |
| 1148 | LumB | 1 | 1 | 0 | 13.542466 | 4.6027397 | 1 | 2 | 1 | 1 | 0 |
| 1149 | LumB | 2 | 1 | 0 | 18.715068 | 18.715068 | 0 | 3 | 1 | 1 | 0 |
| 1150 | Her2-enriched | 2 | 1 | 1 | 2.6027397 | 2.0931507 | 1 | 1 | 0 | NA | 1 |
| 1151 | LumB | NA | NA | 1 | 18.641096 | 18.641096 | 0 | 3 | 1 | 1 | 0 |
| 1152 | LumA | 1 | 0 | 0 | 18.621918 | 18.621918 | 0 | 3 | 1 | 1 | 0 |
| 1153 | LumA | NA | NA | 0 | 1.460274 | 1.460274 | 0 | NA | 1 | NA | 0 |
| 1154 | LumA | 2 | 0 | 0 | 7.3479452 | 7.3479452 | 0 | 2 | 1 | 1 | 0 |
| 1155 | LumA | 1 | 1 | 0 | 7.4246575 | 6.939726 | 1 | 2 | 1 | 1 | 0 |
| 1156 | Normal-like | 2 | 0 | 0 | 18.452055 | 18.452055 | 0 | 3 | 0 | 0 | 0 |
| 1157 | Her2-enriched | 2 | 1 | 1 | 4.62465.75 | 3.7671233 | 1 | 1 | NA | 0 | NA |
| 1158 | LumA | 1 | 1 | 0 | 7.3890411 | 8.060274 | 1 | 1 | 1 | NA | 0 |
| 1159 | Her2-enriched | 3 | NA | 1 | 18.986301 | 0.9863014 | 1 | 3 | 1 | NA | 1 |
| 1160 | Her2-enriched | 2 | 0 | 1 | 17.969863 | 17.969863 | 0 | 3 | 1 | 0 | NA |
| 1161 | LumB | 2 | 1 | 0 | 4.1452055 | 4.1452055 | 0 | 2 | 1 | 0 | 0 |
| 1162 | LumA | 1 | 1 | 0 | 17.909589 | 17.909589 | 0 | 3 | 1 | 1 | 0 |
| 1163 | LumA | 2 | 1 | 0 | 9.3972603 | 9.3972603 | 0 | 2 | 1 | 1 | 0 |
| 1164 | LumA | 2 | 0 | 0 | 7.8109589 | 7.8109589 | 0 | 2 | 1 | 1 | 0 |
| 1165 | Her2-enriched | 2 | 1 | 0 | NA | NA | NA | 1 | 0 | 0 | NA |
| 1166 | Basal-like | 1 | 0 | 1 | 17.378082 | 17.378082 | 0 | 3 | 0 | 0 | 0 |
| 1167 | Her2-enriched | NA | NA | 0 | 17.071233 | 17.071233 | 0 | 3 | 1 | 0 | 0 |
| 1168 | LumA | 1 | 0 | NA | 17.161644 | 17.161644 | 0 | 3 | 1 | 1 | 0 |
| 1169 | Basal-like | 3 | NA | 1 | 10.742466 | 6.5315068 | 1 | 1 | 0 | NA | 0 |
| 1170 | Basal-like | 1 | NA | 1 | NA | NA | NA | 1 | 0 | 0 | 0 |
| 1171 | Her2-enriched | 1 | 1 | 1 | 4.8438356 | 2.7506849 | 1 | 2 | 1 | 1 | 1 |
| 1172 | LumB | 1 | NA | 0 | 7.3972603 | 7.3972603 | 0 | 2 | 1 | 1 | NA |
| 1173 | LumB | 1 | 0 | 1 | 16.934247 | 3.4219178 | 1 | 3 | 1 | 1 | 0 |
| 1174 | LumA | 1 | 0 | 0 | 16.90137 | 16.90137 | 0 | 3 | 1 | 1 | 0 |
| 1175 | LumB | 2 | 1 | 0 | 16.882192 | 16.882192 | 0 | 3 | 1 | 1 | 0 |
| 1176 | Her2-enriched | 2 | NA | 1 | 9.1232877 | 9.1232877 | 0 | 2 | 1 | 1 | 1 |
| 1177 | Basal-like | 1 | 1 | 1 | 2.0986301 | 0.6547945 | 1 | 1 | 0 | 0 | 0 |
| 1178 | Her2-enriched | 2 | 0 | 1 | 2.1534247 | 1.7506849 | 1 | 1 | 0 | 0 | 0 |
| 1179 | Basal-like | 1 | NA | 1 | 0.0493151 | 0.0027397 | 1 | 1 | 0 | 0 | 0 |
| 1180 | LumB | 1 | 0 | 0 | 8.0328767 | 4.7917808 | 1 | 1 | 1 | 0 | 0 |
| 1181 | LumA | 1 | 0 | 0 | 7.8383562 | 7.8383562 | 0 | 2 | 1 | NA | 0 |
| 1182 | Her2-enriched | 3 | 1 | 0 | 16.706849 | 16.706849 | 0 | 3 | 0 | 0 | 0 |
| 1183 | Basal-like | 2 | 1 | 0 | 3.3835616 | 1.0547945 | 1 | 1 | 1 | 1 | NA |
| 1184 | Basal-like | 2 | 0 | 1 | 16.547945 | 16.547945 | 0 | 3 | 0 | 0 | 1 |
| 1185 | Her2-enriched | 2 | 0 | 0 | 16.520548 | 16.520548 | 0 | 3 | 1 | 1 | 1 |
| 1186 | Normal-like | 2 | 1 | 0 | 1.7506849 | 1.7506849 | 0 | 2 | 1 | NA | 0 |
| 1187 | Her2-enriched | 3 | NA | 0 | 1.7150685 | 0.0082192 | 1 | 1 | NA | 0 | 1 |
| 1188 | Basal-like | 2 | 1 | 1 | 16.479452 | 1.8219178 | 1 | 3 | 0 | 0 | 0 |
| 1189 | Normal-like | 2 | 0 | 0 | 11.153425 | 7.0520548 | 1 | 1 | NA | NA | 0 |
| 1190 | LumA | 2 | 0 | 0 | 16.287671 | 16.287671 | 0 | 3 | 1 | 1 | 0 |
| 1191 | LumB | 2 | 0 | 0 | 16.345205 | 16.345205 | 0 | 3 | 1 | 1 | 0 |
| 1192 | LumB | 1 | 0 | 0 | 16.227397 | 16.227397 | 0 | 3 | 1 | NA | NA |
| 1193 | LumA | NA | NA | 0 | 6.2821918 | 6.2821918 | 0 | 2 | 1 | 1 | 0 |
| 1194 | LumA | 3 | NA | 0 | 4.2767123 | 1.2849315 | 1 | 1 | 1 | 1 | 0 |
| 1195 | LumA | 2 | 0 | 0 | 9.7479452 | 9.7479452 | 0 | 2 | 1 | 1 | NA |
| 1196 | LumB | 1 | NA | 0 | 7.0684932 | 7.0684932 | 0 | 2 | 1 | 0 | 0 |
| 1197 | LumA | 1 | 0 | 0 | 5.8027397 | 5.8027397 | 0 | 2 | 1 | 0 | 0 |
| 1198 | LumA | 2 | 1 | 0 | 1.0383562 | 1.0383562 | 0 | 2 | 1 | NA | 0 |
| 1199 | LumB | 2 | 0 | 0 | 7.8520548 | 7.5178082 | 1 | 1 | 1 | 1 | 0 |
| 1200 | LumA | 2 | 0 | 0 | 15.863014 | 15.863014 | 0 | 3 | 1 | 1 | 0 |

TABLE 3-continued

Clinical and Subtype Data for qRT-PCR Test Set

| Patient ID | Subtype Prediction | pT* | pN^ | Grade% | Overall Survival | Relapse Free Survival | Any Relapse*** | DSS** | ER (IHC)^^ | PR (IHC)^^ | Her2 (IHC)^^ |
|---|---|---|---|---|---|---|---|---|---|---|---|
| 1201 | Normal-like | 1 | 0 | 01 | 15.693151 | 15.693151 | 0 | 3 | 1 | 0 | 0 |
| 1202 | LumB | 1 | NA | 0 | 0.030137 | 0.030137 | 0 | 2 | 1 | 0 | 0 |
| 1203 | Her2-enriched | 2 | 1 | 0 | 10.0465.75 | 10.046575 | 0 | 2 | 0 | 0 | 0 |
| 1204 | LumA | 2 | 0 | 0 | 15.210959 | 15.210959 | 0 | 3 | 1 | 1 | 0 |
| 1205 | LumA | 1 | NA | 0 | 15.189041 | 10.890411 | 1 | 3 | 1 | 1 | 0 |
| 1206 | LumA | 2 | 0 | 0 | 15.169863 | 15.169863 | 0 | 3 | 1 | NA | NA |
| 1207 | LumA | 1 | 0 | NA | 2.2794521 | 0.9726027 | 1 | 1 | 1 | NA | 0 |
| 1208 | Her2-enriched | 1 | 0 | 1 | 8.0712329 | 6.0547945 | 1 | 1 | 0 | 0 | 1 |
| 1209 | Basal-like | 2 | 1 | 0 | 4.12876.71 | 3.8630137 | 1 | 1 | 1 | 0 | 0 |
| 1210 | LumB | 1 | 0 | 0 | 15.035616 | 15.035616 | 0 | 3 | 1 | 1 | 0 |
| 1211 | LumB | 3 | NA | 0 | 1.9780822 | 0.9123288 | 1 | 1 | 1 | 1 | 0 |
| 1212 | Basal-like | 1 | 1 | 0 | 15.032877 | 15.032877 | 0 | 3 | 1 | 1 | 0 |
| 1213 | Her2-enriched | 2 | 1 | 0 | 15 | 15 | 0 | 3 | 0 | 0 | 0 |
| 1214 | Basal-like | 1 | 0 | 1 | 14.967123 | 14.967123 | 0 | 3 | 0 | NA | 0 |
| 1215 | Normal-like | 1 | 1 | 0 | 12.073973 | 12.073973 | 0 | 2 | 1 | 0 | NA |
| 1216 | LumA | 2 | 0 | 1 | 8.8 | 8.7835616 | 1 | 2 | 1 | 1 | 0 |
| 1217 | LumA | 1 | 1 | 0 | 14.89863 | 14.375342 | 1 | 3 | 1 | 1 | 0 |
| 1218 | LumA | 2 | 1 | 0 | 7.6767123 | 6.4410959 | 1 | 1 | 1 | NA | 0 |
| 1219 | LumA | 3 | 1 | 0 | 4.1890411 | 1.6493151 | 1 | 1 | 1 | 1 | 0 |
| 1220 | Basal-like | 3 | 1 | 0 | 2.5150685 | 0.4109589 | 1 | 1 | 0 | 0 | 0 |
| 1221 | Normal-like | 1 | 0 | 1 | 14.852055 | 14.852055 | 0 | 3 | 0 | NA | NA |
| 1222 | LumA | 1 | 0 | 0 | 14.772603 | 14.772603 | 0 | 3 | NA | NA | 0 |
| 1223 | Basal-like | 3 | 1 | 1 | 1.5589041 | 1.3260274 | 1 | 2 | 0 | 0 | 0 |
| 1224 | Normal-like | 1 | 0 | 0 | 14.709589 | 14.709589 | 0 | 3 | NA | NA | 0 |
| 1225 | Basal-like | 2 | 1 | 0 | 14.69589 | 13.29589 | 1 | 3 | 1 | 1 | 0 |
| 1226 | LumA | 3 | NA | 0 | 2.5232877 | 0.0410959 | 1 | 1 | 1 | 0 | 0 |
| 1227 | LumA | 1 | 0 | 0 | 14.578082 | 14.578082 | 0 | 3 | 1 | 0 | 0 |
| 1228 | LumB | 2 | 0 | 0 | 14.572603 | 14.572603 | 0 | 3 | 1 | 1 | 0 |
| 1229 | Her2-enriched | 2 | 0 | 1 | 14.613699 | 14.613699 | 0 | 3 | 0 | 0 | 0 |
| 1230 | LumA | 2 | 0 | 0 | 2.0109589 | 2.0109589 | 0 | 2 | 1 | 1 | 0 |
| 1231 | LumA | 1 | 0 | 0 | 14.542466 | 14.542466 | 0 | 3 | 1 | 0 | 0 |
| 1232 | Her2-enriched | 1 | 0 | 1 | 14.534247 | 14.534247 | 0 | 3 | 1 | 1 | 0 |
| 1233 | LumB | 1 | NA | 0 | 4.9123288 | 4.0849315 | 1 | 1 | 1 | 1 | 0 |
| 1234 | LumB | NA | 1 | 0 | 5.4876712 | 5.4876712 | 0 | 2 | 1 | NA | 0 |
| 1235 | LumA | 1 | 0 | 0 | 14.641096 | 14.641096 | 0 | 3 | 1 | 1 | 0 |
| 1236 | LumA | 2 | 0 | 0 | 14.520548 | 14.520548 | 0 | 3 | 1 | 1 | 0 |
| 1237 | LumA | 2 | 0 | 0 | 7.3780822 | 5.0109589 | 1 | 2 | 1 | 1 | 0 |
| 1238 | Her2-enriched | 3 | NA | 1 | NA | NA | NA | 1 | 1 | 0 | 0 |
| 1239 | Her2-enriched | 2 | 1 | 0 | 14.465753 | 14.465753 | 0 | 3 | 1 | NA | NA |
| 1240 | Basal-like | 3 | 1 | 0 | 14.438356 | 14.438356 | 0 | 3 | 1 | NA | NA |
| 1241 | LumA | 1 | 0 | 0 | 14.421918 | 14.421918 | 0 | 3 | 1 | 1 | 0 |
| 1242 | LumA | 2 | 0 | 0 | 14.419178 | 14.419178 | 0 | 3 | 1 | NA | NA |
| 1243 | LumB | 1 | 0 | 0 | 14.408219 | 14.408219 | 0 | 3 | 1 | 1 | 0 |
| 1244 | LumB | 1 | 1 | 0 | 10.013699 | 10.013699 | 0 | 2 | 1 | 1 | 0 |
| 1245 | LumA | 2 | 0 | 0 | 14.383562 | 14.383562 | 0 | 3 | 1 | 1 | 0 |
| 1246 | LumB | 2 | 0 | 0 | 4.5643836 | 4.5643836 | 0 | 2 | 1 | 1 | 0 |
| 1247 | LumB | 1 | 0 | 0 | 14.312329 | 1.4739726 | 1 | 3 | 1 | 1 | 0 |
| 1248 | Normal-like | 1 | 1 | 0 | 14.249315 | 14.249315 | 0 | 3 | NA | NA | 0 |
| 1249 | LumA | 3 | 0 | 0 | 13.49863 | 13.49863 | 0 | 2 | 1 | 0 | 0 |
| 1250 | Basal-like | NA | 0 | 1 | 14.235616 | 14.235616 | 0 | 3 | 0 | NA | 0 |
| 1251 | LumB | 1 | 0 | 0 | 14.945205 | 14.945205 | 0 | 3 | 1 | 0 | 0 |
| 1252 | Normal-like | 1 | 0 | 0 | 1.6547945 | 1.2493151 | 1 | 1 | NA | NA | 0 |
| 1253 | LumA | 2 | 1 | 0 | 4.2164384 | 4.2164384 | 0 | 2 | 1 | 0 | 0 |
| 1254 | Normal-like | 1 | 0 | 0 | 12.526027 | 12.526027 | 0 | 3 | 1 | NA | 0 |
| 1255 | LumB | 2 | 1 | 0 | 12.463014 | 12.463014 | 0 | 3 | 1 | 1 | 0 |
| 1256 | Basal-like | 2 | 1 | 0 | 3.7205479 | 1.7452055 | 1 | 1 | 1 | 1 | NA |
| 1257 | Normal-like | 1 | 0 | 0 | 12.427397 | 12.427397 | 0 | 3 | 1 | NA | 0 |
| 1258 | LumA | 2 | 0 | 0 | 12.372603 | 12.372603 | 0 | 3 | 1 | NA | 0 |
| 1259 | LumA | 1 | 1 | 0 | 12.328767 | 12.328767 | 0 | 3 | 1 | NA | NA |
| 1260 | Basal-like | 1 | 1 | 0 | 12.29589 | 2.5945205 | 1 | 3 | 1 | 1 | 0 |
| 1261 | LumA | 2 | 0 | 0 | 12.312329 | 12.312329 | 0 | 3 | 1 | NA | 0 |
| 1262 | Normal-like | 1 | 0 | 0 | 12.180822 | 12.180822 | 0 | 3 | 1 | NA | 0 |
| 1263 | Basal-like | 1 | 0 | 0 | 12.2 | 12.2 | 0 | 3 | NA | NA | NA |
| 1264 | Her2-enriched | 1 | 0 | 1 | 3.6 | 2.0684932 | 1 | 1 | 1 | 1 | 0 |
| 1265 | LumA | 2 | 1 | 0 | 12.2 | 12.2 | 0 | 3 | 1 | 1 | 0 |
| 1266 | Normal-like | 1 | 1 | NA | 11.857534 | 11.857534 | 0 | 3 | 1 | NA | 0 |
| 1267 | Her2-enriched | 2 | 0 | 1 | 11.186301 | 11.186301 | 0 | 3 | 0 | 0 | 0 |
| 1268 | Normal-like | 1 | 1 | NA | 11.073973 | 11.073973 | 0 | 3 | 1 | NA | 0 |
| 1269 | Normal-like | 3 | 0 | 0 | 10.969863 | 10.969863 | 0 | 3 | 1 | 1 | 0 |
| 1270 | LumA | 2 | NA | 0 | 10.920548 | 10.920548 | 0 | 3 | 1 | 1 | 0 |
| 1271 | LumA | 2 | 1 | 0 | 10.79726 | 10.79726 | 0 | 3 | 1 | 0 | 0 |
| 1272 | LumB | 1 | 0 | 0 | 10.668493 | 10.668493 | 0 | 3 | 1 | 0 | 0 |
| 1273 | LumA | 2 | 1 | 0 | 10.167123 | 10.167123 | 0 | 3 | 1 | 1 | NA |
| 1274 | LumA | 1 | 0 | 0 | 9.6821918 | 9.6821918 | 0 | 3 | 1 | NA | 0 |

TABLE 3-continued

Clinical and Subtype Data for qRT-PCR Test Set

| Patient ID | Subtype Prediction | pT* | pN^ | Grade^% | Overall Survival | Relapse Free Survival | Any Relapse*** | DSS** | ER (IHC)^^ | PR (IHC)^^ | Her2 (IHC)^^ |
|---|---|---|---|---|---|---|---|---|---|---|---|
| 1275 | Normal-like | 2 | 0 | 0 | 9.5917808 | 9.5917808 | 0 | 3 | 1 | 1 | 0 |
| 1276 | Normal-like | 1 | 0 | 0 | 9.6082192 | 9.6082192 | 0 | 3 | 1 | 1 | 0 |
| 1277 | Basal-like | 2 | 0 | 1 | 9.5287671 | 9.5287671 | 0 | 3 | 0 | NA | 0 |
| 1278 | Normal-like | 1 | 0 | 0 | 6.5835616 | 6.2547945 | 1 | 1 | 1 | 1 | NA |
| 1279 | Basal-like | 2 | 1 | 0 | 9.3643836 | 9.3643836 | 0 | 3 | NA | NA | 0 |

| biomarker | 0 | 1 | NA | 15 |
|---|---|---|---|---|
| ER | <1% positive nuclei | ≥1% positive nuclei | uninterpretable | |
| PR | <1% positive nuclei | ≥1% positive nuclei | uninterpretable | |
| Her2-enriched | negative or weak expression | strong expression | uninterpretable | |

TABLE 4

Source Data for qRT-PCR and Microarray Datasets

| Author | Samples | Platform | GEO Accessions (or other availability) | Use in Subtype Classification | Use in Risk Prediction | Number N-, no adjavant systemic therapy | Number of endocrine Therapy Only | % ER+ |
|---|---|---|---|---|---|---|---|---|
| Parker et al | 189 | qRT-PCR | | — | — | 0 | 0 | 54% |
| Parker et al | 279 | qRT-PCR | | Test | Test | 0 | 0 | 62% |
| Parker et al | 544 | Agilent Custom, 1A, 1Av2 | GSE10886 | Common to qRT-PCR for Training (189); others in Test (355) | 355 in Test | 31 | 27 | 56% |
| Hess et al | 133 | Affymetrix U133A | bioinformatics.mdanderson.org/pubdata | Test | Test | 0 | 0 | 62% |
| Ivshina et al | 289 | Affymetrix U133A | GSE4922 | Test | Test | 142 | 66 | 86% |
| Loi et al | 414 | Affymetrix U133A & U133 + 2 | GSE6532 | Test | Test | 137 | 277 | 89% |
| van de Vijver et al | 295 | Agilent | GSE2845 | Test | Untreated for Training (165); others in Test (130) | 165 | 20 | 76% |
| Wang et al | 286 | Affymetrix U133A | GSE2034 | Test | Test | 286 | 0 | 73% |

TABLE 5

Multivariate and univariate analyses using 1451 samples from a combined microarray test set with clinical data

| | Univariate | | Multivariate* (subtype) | | Multivariate* (clinical) | | Multivariate*†‡ (subtype + clinical) | |
|---|---|---|---|---|---|---|---|---|
| | Co-efficient | p-value^ | Coefficient | p-value^ | Coefficient | p-value^ | Coefficient | p-value^ |
| Basal-like | 0.14 | 0.25 | 0.12 | 5.10E−01 | — | | −0.11 | 5.50E−01 |
| HER-enriched | 0.62 | 1.00E−08 | 0.53 | 1.60E−03 | — | | 0.35 | 4.00E−02 |
| LumA | −0.94 | 1.00E−22 | −0.67 | 6.20E−05 | — | | −0.64 | 1.60E−04 |
| LumB | 0.42 | 5.60E−06 | 0.3 | 5.50E−02 | — | | 0.24 | 1.30E−01 |
| ER Status | −0.47 | 1.80E−06 | — | — | −0.5 | 5.50E−07 | −0.37 | 3.00E−03 |
| Tumor Size | 0.62 | 3.50E−12 | — | — | 0.54 | 6.10E−09 | 0.47 | 5.30E−07 |
| Node Status | 0.37 | 2.80E−05 | — | — | 0.24 | 1.10E−02 | 0.19 | 5.00E−02 |

*Normal-like class used as reference state
^Significant variables are in italics
†p = 4e−10 (by likelihood ratio test) for comparison with the Subtype model
‡2e−13 (by likelihood ratio test) for comparison with the Clinical model

TABLE 6

| | | # | % | % | % HER2- | % Basal- | % Normal- |
| Test set | ER-status | Samples | LumA | LumB | enriched | like | like |
|---|---|---|---|---|---|---|---|
| UNC | ER-positive | 137 | 44% | 35% | 7% | 4% | 9% |
| | ER-negative | 107 | 7% | 5% | 19% | 51% | 18% |
| Hess et al | ER-positive | 82 | 44% | 32% | 10% | 1% | 13% |
| | ER-negative | 51 | 2% | 2% | 41% | 51% | 4% |
| Ivshina et al | ER-positive | 211 | 42% | 29% | 11% | 3% | 9% |
| | ER-negative | 34 | 9% | 15% | 35% | 38% | 3% |
| Loi et al | ER-positive | 349 | 39% | 38% | 30% | 7% | 8% |
| | ER-negative | 45 | 18% | 9% | 33% | 27% | 13% |
| van de Vijver et al | ER-positive | 225 | 39% | 31% | 14% | 4% | 12% |
| | ER-negative | 70 | 1% | 0% | 31% | 64% | 3% |
| Wang et al | ER-positive | 209 | 35% | 33% | 11% | 8% | 13% |
| | ER-negative | 77 | 5% | 3% | 29% | 57% | 6% |

TABLE 7

T/FAC pathological complete response rates for
PAM50 subtypes and triple-negative classification

| Classification | RD | pCR |
|---|---|---|
| Basal-like | 11 (41%) | 16 (59%) |
| HER2-enriched | 17 (59%) | 12 (41%) |
| LumA | 36 (100%) | 0 (0%) |
| LumB | 22 (82%) | 5 (18%) |
| Normal-like | 13 (93%) | 1 (7%) |
| Triple Negative | 13 (50%) | 13 (50%) |
| Any positive | 82 (80%) | 20 (20%) |
| Triple Negative/Basal | 6 (35%) | 11 (65%) |
| Triple Negative/Non-Basal | 7 (78%) | 2 (22%) |
| Non-Triple Negative/Basal | 4 (50%) | 4 (50%) |
| Non-Triple Negative/Non-Basal | 78 (83%) | 16 (17%) |

*Percentages are calculated by the total per classification

REFERENCES

1. Sorlie T, Perou C M, Tibshirani R, et al: Gene expression patterns of breast carcinomas distinguish tumor subclasses with clinical implications. Proc Natl Acad Sci USA 98:10869-74, 2001
2. van't Veer U, Dai H, van de Vijver M J, et al: Gene expression profiling predicts clinical outcome of breast cancer. Nature 415:530-6, 2002
3. van't Veer U, Paik S, Hayes D F: Gene expression profiling of breast cancer: a new tumor marker. J Clin Oncol 23:1631-5, 2005
4. Paik S, Shak S, Tang G, et al: A multigene assay to predict recurrence of tamoxifen-treated, node-negative breast cancer. N Engl J Med 351:2817-26, 2004
5. Paik S, Tang G, Shak S, et al: Gene expression and benefit of chemotherapy in women with node-negative, estrogen receptor-positive breast cancer. J Clin Oncol 24:3726-34, 2006
6. Hu Z, Fan C, Oh D S, et al: The molecular portraits of breast tumors are conserved across microarray platforms. BMC Genomics 7:96, 2006
7. Loi S, Haibe-Kains B, Desmedt C, et al: Definition of clinically distinct molecular subtypes in estrogen receptor-positive breast carcinomas through genomic grade. J Clin Oncol 25:1239-46, 2007
8. Perou C M, Sorlie T, Eisen M B, et al: Molecular portraits of human breast tumours. Nature 406:747-52, 2000
9. Sorlie T, Tibshirani R, Parker J, et al: Repeated observation of breast tumor subtypes in independent gene expression data sets. Proc Natl Acad Sci USA 100:8418-23, 2003
10. Fan C, Oh D S, Wessels L, et al: Concordance among gene-expression based predictors for breast cancer. N Engl J Med 355:560-9, 2006
11. Perreard L, Fan C, Quackenbush J F, et al: Classification and risk stratification of invasive breast carcinomas using a real-time quantitative RT-PCR assay. Breast Cancer Res 8:R23, 2006
12. Eisen M B, Spellman P T, Brown P O, et al: Cluster analysis and display of genome-wide expression patterns. Proc Natl Acad Sci USA 95:14863-8, 1998
13. Yufeng L, Hayes D L, Nobel A, et al: Statistical significance of clustering for high dimension low sample size data. Journal of the American Statistical Association, in press
14. Mullins M, Perreard L, Quackenbush J F, et al: Agreement in breast cancer classification between microarray and quantitative reverse transcription PCR from fresh-frozen and formalin-fixed, paraffin-embedded tissues. Clin Chem 53:1273-9, 2007
15. Storey J D, Tibshirani R: Statistical methods for identifying differentially expressed genes in DNA microarrays. Methods Mol Biol 224:149-57, 2003
16. Dudoit S, Fridlyand J: A prediction-based resampling method for estimating the number of clusters in a dataset. Genome Biol 3:RESEARCH0036, 2000
17. Tibshirani R, Hastie T, Narasimhan B, et al: Diagnosis of multiple cancer types by shrunken centroids of gene expression. Proc Natl Acad Sci USA 99:6567-72, 2002
18. Dabney A R: Classification of microarrays to nearest centroids. Bioinformatics 21:4148-54, 2005
19. Hess K R, Anderson K, Symmans W F, et al: Pharmacogenomic predictor of sensitivity to preoperative chemotherapy with paclitaxel and fluorouracil, doxorubicin, and cyclophosphamide in breast cancer. J Clin Oncol 24:4236-44, 2006
20. van de Vijver M J, He Y D, van't Veer U, et al: A gene-expression signature as a predictor of survival in breast cancer. N Engl J Med 347:1999-2009, 2002
21. Chaudhuri P, Marron J S: SiZer for Exploration of Structures in Curves. Journal of the American Statistical Association 94:807-823, 1999
22. Sheather S J, Jones M C: A Reliable Data-Based Bandwidth Selection Method for Kernel Density Estimation. Journal of the Royal Statistical Society 53:683-690, 1991
23. Neve R M, Chin K, Fridlyand J, et al: A collection of breast cancer cell lines for the study of functionally distinct cancer subtypes. Cancer Cell 10:515-27, 2006
24. Rouzier R, Pusztai L, Delaloge S, et al: Nomograms to predict pathologic complete response and metastasis-free survival after preoperative chemotherapy for breast cancer. J Clin Oncol 23:8331-9, 2005

25. Herschkowitz J I, Simin K, Weigman V J, et al: Identification of conserved gene expression features between murine mammary carcinoma models and human breast tumors. Genome Biol 8: R76, 2007

26. Rakha E, Ellis I, Reis-Filho J: Are triple-negative and basal-like breast cancer synonymous? Clin Cancer Res 14:618; author reply 618-9, 2008

27. Cheang M C, Voduc D, Bajdik C, et al: Basal-like breast cancer defined by five biomarkers has superior prognostic value than triple-negative phenotype. Clin Cancer Res 14:1368-76, 2008

Example 2

Introduction and Background Data

This technology also covers the use of the PAM50-based intrinsic subtype classifier as a predictive and prognostic signature in the neoadjuvant endocrine therapy setting. Postmenopausal patients with Stage 2 and 3 ER and/or PgR positive breast cancer can be treated with an endocrine agent, typically an aromatase inhibitor or tamoxifen, before surgery to improve clinical outcomes, i.e., to promote the use of breast conserving surgery or to improve operability in the setting of a tumor that has invaded into the tissues surrounding the breast. A predictive test to increase the confidence that an individual patient will respond to neoadjuvant endocrine therapy is a significant advance.

SUMMARY

The PAM50 based intrinsic subtype and proliferation-weighted risk score, when applied to samples from ER+breast cancers harvested after initiating treatment with an endocrine agent, can be used to predict response to neoadjuvant endocrine therapy and determine the prognosis for patients with ER+breast cancer who will undergo long term therapy with an endocrine agent. A prognostic gene expression model trained on tumor samples taken before treatment (PAM50 proliferation weighted risk score—described elsewhere herein) was applied to samples taken after the initiation of neoadjuvant endocrine therapy. This approach is unique because previous studies on the interaction of gene expression profiles and prognosis have only examined pretreatment samples and have never applied these models to post treatment samples. The prognostic and predictive properties of the PAM50 intrinsic subtype and proliferation weighted prognostic model in baseline samples is compared to the same models applied to samples taken one month after initiating neoadjuvant endocrine therapy. Application of the PAM50 intrinsic subtype and proliferation-weighted risk of relapse model to the one month on treatment samples accurately identifies aggressive tumors that fail to respond to neo adjuvant or adjuvant endocrine treatment. Patients with these tumors should be immediately triaged to alternative neoadjuvant treatments, such as chemotherapy, because these poor tumors behave as endocrine therapy refractory aggressive disease. A high degree of correlation was established between the Ki67 proliferation marker and the proliferation weighted PAM50 risk score supporting the claim that the PAM50 proliferation weighted risk score has prognostic properties. However these prognostic properties are markedly enhanced when the analysis is applied to samples harvested from tumors that have been exposed to an endocrine agent. In practice this can be easily achieved by prescribing an endocrine agent for a few weeks before definitive surgery or by re-sampling a tumor early in the course of neoadjuvant endocrine treatment in order to identify unresponsive tumors.

Methodology:

The evidence to support these claims arises from a National Cancer Institute sponsored Phase 2 trial of neoadjuvant therapy with the aromatase inhibitor letrozole (NCI Grant No. RO1 CA095614). Eligibility for the trial required postmenopausal women with ER and/or PgR positive Stage 2 and 3 breast cancers. Patients received 4 months of therapy and then they underwent surgery. Frozen tumor samples were obtained at baseline, one month and at surgery. The samples were analyzed by frozen-section and RNA was extracted using standard methodologies from tumor rich specimens and subjected to gene expression analysis using Agilent 1X44K arrays. The data was normalized to the data set used to train the PAM50 classifier (methods described above) and two readouts were produced: An intrinsic classification (LumA, LumB, HER2-enriched, Basal-like and Normal-like) and a proliferation weighted PAM50 risk score. The aim of this study was to correlate the outcomes of neoadjuvant endocrine therapy with the intrinsic classification and the proliferation weighted risk score derived from both the baseline sample and the on treatment sample taken at one month.

Results:

The PAM50 intrinsic subtype and proliferation weighted risk score showed marked changes at one month post therapy (Table 8). Most of the transitions occurred in the LumB group with the majority shifting to LumA, but 16% remained in the LumB category despite treatment. In contrast, most LumA tumors stayed LumA post therapy. These transitions were due to the suppression of the proliferation cluster in the LumB group since the PAM50 proliferation weighted risk score showed similar shifts, with the majority of tumors typed high risk (68%) becoming intermediate or low risk in the on treatment samples. Tight correlation with Ki67 immunohistochemisty further underscores this conclusion. The correlation between baseline Ki67 values and PAM50 proliferation weighted risk score was high (P=2.8xE-8). Similarly the one month Ki67 values and the one month PAM50 proliferation score were also tightly correlated (P=3.8E-10). However, while the baseline PAM50 proliferation weighted risk score subtype exhibited only a very weak correlation with the end of study Ki67 values (P=0.04), there was a tight correlation between the one month PAM50 proliferation weighted risk score and the end of study Ki67 values—most of which were obtained at surgery 4 to 6 months later (P=6.8E-11). This last observation strongly supports the claim that an early on treatment PAM50 based test can be used to predict whether the final surgical samples will have favorable biomarker features, such as a low proliferation rate.

To determine the clinical correlations associated with these endocrine-therapy induced changes in intrinsic breast cancer subtype and risk score, four endpoints were examined: clinical response (RECIST criteria), pathological T size (T1 versus higher—as evidence for pathological down staging with treatment), dichotomized Ki67 values (with tumors exhibiting a Ki67 natural log value of 1 or less considered to be exhibiting a favorable profile) and relapse events. The baseline subtype or risk score showed no convincing ability to predict any of these endpoints, which, in terms of the relapse, is likely a function of the small sample size in this trial (Table 9). In contrast, and despite the small sample size, the PAM50 intrinsic subtype at one month (Table 10) did show statistically significant relationships with clinical response (P=0.01), favorable end of treatment Ki67 value (P=0.0003) and relapse (0.009). These strong relationships were driven by the extremely poor outcome associated with tumors that were either designated "non-luminal" or Luminal B in the on treatment specimens. The PAM50 proliferation-weighted risk score had similar properties. Baseline PAM50 proliferation-weighted risks score did not predict the neoadjuvant or long term outcomes very effectively (Table 11). However tumors that were designated high risk at one month showed significant correlations with poor outcomes in all four endpoints examined, i.e., poor clinical response (P=0.02), low pathological downstaging (p=0.02), unfavorable end of treatment Ki67 value (P=0.0001) and relapse (p=0.001) (Table 12).

Thus, application of the PAM50 based intrinsic subtype and risk score to tumor samples harvested from primary ER+breast cancers undergoing presurgical treatment with an endocrine agent can be used for the following purposes:

1) Prediction of a failure to respond to neoadjuvant endocrine therapy

2) Determination of the prognosis for patients with ER+breast cancer subsequently undergoing adjuvant endocrine treatment.

TABLE 8

PAM50 subtype and proliferation-weighted risk group switching at one month after treatment.

| Change Category | Number | Percentage |
|---|---|---|
| PAM50 Intrinsic Subtype Changes | | |
| LumA to LumA | 18 | 31.0 |
| LumA to LumB | 1 | 1.7 |
| LumA to Non-Lum | 0 | 0 |
| LumB to LumA | 29 | 50.0 |
| LumB to LumB | 6 | 10.3 |
| LumB to Non-Lum | 1 | 1.7 |
| Non-Lum to Non-Lum | 1 | 1.7 |
| Non Lum to LumA | 0 | 0 |
| Non Lum to LumB | 2 | 3.4 |
| Total | 58 | 100 |
| Proliferation weighted PAM50 Risk Score | | |
| Low to Low | 5 | 8.6 |
| Low to Med | 1 | 1.7 |
| Low to High | 0 | 0 |
| Med to Low | 7 | 12.1 |
| Med to Med | 12 | 20.7 |
| Med to High | 1 | 1.7 |
| High to Low | 11 | 19 |
| High to Med | 14 | 24.1 |
| High to High | 7 | 12.1 |
| Total | 58 | 100 |

TABLE 9

Interactions between the baseline PAM50 intrinsic subtype designations and outcomes from neoadjuvant endocrine therapy.

| Subtype or score at Baseline | End of Study Endpoint | Number/ Total | % favorable outcome | P value on interaction |
|---|---|---|---|---|
| Subtype | Clinical Response CR + PR v SD + PD | | | 0.54 |

TABLE 9-continued

Interactions between the baseline PAM50 intrinsic subtype designations and outcomes from neoadjuvant endocrine therapy.

| Subtype or score at Baseline | End of Study Endpoint | Number/ Total | % favorable outcome | P value on interaction |
|---|---|---|---|---|
| LumA | | 28/76 | 60.71 | |
| LumB | | 42/76 | 69.05 | |
| NonLum† | | 6/76 | 50.00 | |
| | Path tumor size* ≤2 cm versus >2 cm | | | 0.29 |
| LumA | | 29/78 | 37.79 | |
| LumB | | 43/78 | 48.84 | |
| NonLum† | | 6/78 | 16.67 | |
| | Log normal Ki67# ≤log 1.0 versus >1.0 | | | 0.03 |
| LumA | | 30/29 | 66.67 | |
| LumB | | 43/79 | 37.21 | |
| NonLum† | | 6/79 | 33.33 | |
| | Relapse Yes versus No | | | 0.262 |
| LumA | | 30/78 | 90.00 | |
| LumB | | 42/78 | 90.4762 | |
| NonLum† | | 6/78 | 66.67 | |

*Since all patients had clinical stage 2 or 3 disease, pathological tumor stage one are surgery was taken as evidence of successful down-staging. Tumors that progressed during therapy and underwent neoadjuvant chemotherapy are assumed to have a pathological T size of greater than 2 cm at the end of study.
End of study Ki67 is defined as either the surgical specimen or the one month value if the patient progressed on neoadjuvant endocrine therapy and underwent chemotherapy or did not undergo surgery.
†Non-Luminal refers to samples designated Basal-like or HER2 enriched. Normal-like is not included in this analysis because these samples are assumed to not contain sufficient tumor cells for adequate subtyping.

TABLE 10

Interactions between one month on treatment PAM50 intrinsic subtype designations and outcomes from neoadjuvant endocrine therapy.

| PAM50 Subtype at one month | End of Study Endpoint | Number/ Total | % favorable outcome | P value on interaction |
|---|---|---|---|---|
| Subtype | Clinical Response CR + PR v SD + PD | | | 0.01 |
| LumA | | 45/56 | 75.56 | |
| LumB | | 9/56 | 44.44 | |
| NonLum | | 2/56 | 0 | |
| | Path tumor size* ≤2 cm versus >2 cm | | | 0.41 |
| LumA | | 46/57 | 47.83 | |
| LumB | | 9/57 | 22.22 | |
| NonLum | | 2/57 | 50.00 | |
| | Log normal Ki67# ≤log 1.0 versus >1.0 | | | 0.0003 |
| LumA | | 47/58 | 61.70 | |
| LumB | | 9/58 | 0 | |
| NonLum | | 2/58 | 0 | |
| | Relapse Yes versus No | | | 0.009 |
| LumA | | 45/53 | 93.62 | |
| LumB | | 7/53 | 57.14 | |
| NonLum | | 2/53 | 50.00 | |

*Since all patients had clinical stage 2 or 3 disease, pathological tumor stage one are surgery was taken as evidence of successful down-staging. Tumors that progressed during therapy and underwent neoadjuvant chemotherapy are assumed to have a pathological T size of greater than 2 cm at the end of study.
End of study Ki67 is defined as either the surgical specimen or the one month value if the patient progressed on neoadjuvant endocrine therapy and underwent chemotherapy or did not undergo surgery.
†Non-Luminal refers to samples designated Basal-like or HER2 enriched. Normal-like is not included in this analysis because these samples are assumed to not contain sufficient tumor cells for adequate subtyping.

TABLE 11

Interactions between baseline PAM50 proliferation weighted risk
score designations and outcomes from neoadjuvant endocrine therapy

| Risk Score, with proliferation at Baseline | End of Study Endpoint | Number/ Total | % favorable outcome | P value on interaction† |
|---|---|---|---|---|
| | Clinical Response CR + PR v SD + PD | | | 0.4573 |
| Low | | 9/76 | 44.44 | |
| Med | | 28/76 | 67.79 | |
| High | | 39/76 | 66.67 | |
| | Path tumor size* ≤2 cm versus >2 cm | | | 1.0 |
| Low | | 9/78 | 44.44 | |
| Med | | 29/78 | 41.38 | |
| High | | 37/78 | 42.50 | |
| | Log normal Ki67# ≤log 1.0 versus >1.0 | | | 0.03431 |
| Low | | 9/79 | 77.78 | |
| Med | | 30/79 | 56.67 | |
| High | | 40/79 | 35.00 | |
| | Relapse Yes versus No | | | 0.1191 |
| Low | | 9/74 | 77.78 | |
| Med | | 29/74 | 96.67 | |
| High | | 36/74 | 84.62 | |

*Since all patients had clinical stage 2 or 3 disease, pathological tumor stage one are surgery was taken as evidence of successful down-staging. Tumors that progressed during therapy and underwent neoadjuvant chemotherapy are assumed to have a pathological T size of greater than 2 cm at the end of study.
End of study Ki67 is defined as either the surgical specimen or the one month value if the patient progressed on neoadjuvant endocrine therapy and underwent chemotherapy or did not undergo surgery.
†Non-Luminal refers to samples designated Basal-like or HER2 enriched. Normal-like is not included in this analysis because these samples are assumed to not contain sufficient tumor cells for adequate subtyping.

TABLE 12

Interactions between one month on therapy PAM50
proliferation weighted risk score and outcomes
from neoadjuvant endocrine therapy

| PAM50 proliferation weighted risk score at one month | End of Study Endpoint | Number/ Total | % favorable outcome | P value on interaction |
|---|---|---|---|---|
| | Clinical Response CR + PR v SD + PD | | | 0.02 |
| Low | | 21/56 | 80.95 | |
| Med | | 27/56 | 70.37 | |
| High | | 8/56 | 25.00 | |
| | Path tumor size* ≤2 cm versus >2 cm | | | 0.02 |
| Low | | 23/57 | 47.83 | |
| Med | | 26/57 | 53.85 | |
| High | | 8/57 | 0 | |
| | Log normal Ki67# ≤log 1.0 versus >1.0 | | | 0.0001 |
| Low | | 23/58 | 78.26 | |
| Med | | 27/58 | 40.74 | |
| High | | 8/58 | 0 | |
| | Relapse Yes versus No | | | 0.001 |

TABLE 12-continued

Interactions between one month on therapy PAM50
proliferation weighted risk score and outcomes
from neoadjuvant endocrine therapy

| PAM50 proliferation weighted risk score at one month | End of Study Endpoint | Number/ Total | % favorable outcome | P value on interaction |
|---|---|---|---|---|
| Low | | 23/56 | 95.65 | |
| Med | | 27/56 | 92.59 | |
| High | | 6/56 | 33.33 | |

*Since all patients had clinical stage 2 or 3 disease, pathological tumor stage one are surgery was taken as evidence of successful down-staging. Tumors that progressed during therapy and underwent neoadjuvant chemotherapy are assumed to have a pathological T size of greater than 2 cm at the end of study.
End of study Ki67 is defined as either the surgical specimen or the one month value if the patient progressed on neoadjuvant endocrine therapy and underwent chemotherapy or did not undergo surgery.
†Non-Luminal refers to samples designated Basal-like or HER2-like, Normal-like is not included in this analysis because these samples are assumed to not contain sufficient tumor cells for adequate subtyping.

Example 3

A risk of relapse analysis was performed on the samples described in Example 1, except the normal-like class was removed from the model. The normal-like class was represented using true "normals" from reduction mammoplasty or grossly uninvolved tissue. Thus, this class has been removed from the all outcome analyses and this classification is considered as a quality-control measure. Methods not described below are identical to the methods described in Example 1.

Methods

Prognostic and Predictive Models Using Clinical and Molecular Subtype Data:

Univariate and multivariate analyses were used to determine the significance of the intrinsic substypes (LumA, LumB, HER2-enriched, and basal-like) in untreated patients and in patients receiving neoadjuvant chemotherapy. For prognosis, subtypes were compared with standard clinical variables (T, N, ER status, and histological grade), with time to relapse (i.e., any event) as the end point. Subtypes were compared with grade and molecular markers (ER, progesterone receptor (PR), HER2) for prediction in the neoadjuvant setting because pathologic staging is not applicable. Likelihood ratio tests were done to compared models of available clinical data, subtype data, and combined clinical and molecular variables. Categoric survival analyses were performed using a log-rank test and visualized with Kaplan-Meier plots.

Developing Risk Models with Clinical and Molecular Data

The subtype risk model was trained with a multivariate Cox model using Ridge regression fit to the node-negative, untreated subset of the van de Vijver et al. (2002) cohort. A ROR score was assigned to each test case using correlation to the subtype alone (1) (ROR-S) or using subtype correlation along with tumor size (2) (ROR-C):

$$ROR\text{-}S = 0.05*Basal + 0.12*Her2 + -0.34*LumA + 0.0.23*LumB \tag{1}$$

$$ROR\text{-}C = 0.05*Basal + 0.11*Her2 + -0.23*LumA + 0.09*LumB + 0.17*T \tag{2}$$

The sum of the coefficients from the Cox model is the ROR score for each patient. The classify samples into specific risk groups, thresholds were chosen from the training set as described in Example 1. SiZer analysis was performed to characterize the relationship between the ROR score and relapse-free survival. The 95% CIs for the ROR score are local versions of binomial CIs, with the local sample size computed from a Gaussian kernel density estimator based on the Sheather-Jones choice of window width.

Comparison of Relapse Prediction Models

Four models were compared for prediction of relapse: (1) a model of clinical variables alone (tumor size, grade, and ER status), (2) ROR-S, (3) ROR-C, and (4) a model combinding subtype, tumor size, and grade. The C-index was chose to compare the strength of the various models. For each model, the C-index was estimated from 100 randomizations of the untreated cohort into two-thirds training set and one-thirds test set. The C-index was calculated for each test set to form the estimate of each model, and C-index estimates were compared across models using the two sample t test.

ROR model and to select cut-offs. There was a clear improvement in preduction with subtype (ROR-S) relative to the model of available clinical variables only (see Parker et al. (2009) J Clin Oncol 27(8):1160-1167). A combination of clinical variables and subtype (ROR-C) is also a significant improvement over either individual predictor. However, information on grade did not significantly improve the C-index in the combined model, indicating that the prognostic value of grade had been superseded by information provided by the intrinsic subtype model. When using ROR-C for ROR in a prognostic test set of untreated node-negative patients, only the LumA group contained any low-risk patients, and the three-class distinction of low, medium, and high risk was prognostic. Also, ROR-C scores have a linear relationship with probability of relapse at 5 years.

TABLE 13

| | | Models of relapse-free survival (untreated) | | | | |
|---|---|---|---|---|---|---|
| | Model A | | Model B | | Model C | |
| Variable | Hazard ratio | P | Hazard ratio | P | Hazard ratio | P |
| Basal-like* | 1.33 | 0.33 | 1.79 | 0.3 | 1.58 | 0.066 |
| HER-enriched* | 2.53 | 0.00012 | 3.25 | <0.0001 | 2.9 | <0.0001 |
| LumB* | 2.43 | <.0001 | 2.88 | <0.0001 | 2.54 | <0.0001 |
| ER Status† | 0.83 | 0.38 | 0.83 | 0.34 | 0.83 | 0.32 |
| Tumor Size‡ | 1.36 | 0.034 | 1.43 | 0.012 | 1.57 | 0.001 |
| Node Status§ | 1.75 | 0.035 | 1.72 | 0.041 | — | — |
| Histologic grade‖ | 1.4 | 0.0042 | — | — | — | — |
| Full v. subtype¶ | | <.0001 | | <0.0001 | | <0.0001 |
| Full v. clinical# | | <.0001 | | <0.0001 | | <0.0001 |

*Luminal A class used as reference state in multivariable analysis.
†Hazard ratios for ER using positive marker in the numerator.
‡Size ≤2 cm versus >2 cm.
§Any positive node.
‖Grade encoded as an ordinal variable with three levels.
¶Significant P values indicate improved prediction relative to subtype alone.
Significant P values indicate improved prediction relative to clinical data alone.

Results
Risk of Relapse Models for Prognosis in Node-Negative Breast Cancer

Cox models were tested using intrinsic subtype alone and together with clinical variables. Table 13 shows the multivariable analyses of these models in an independent cohort of untreated patients (see Example 1). In model A, subtypes, tumor size (T1 or greater) and histologic grade were found to be significant factors for ROR. The great majority of basal-like tumors (95.9%) were found to be medium or high grade, and therefore, in model B, which is an analysis without grade, basal-like becomes significant. Model C shows the significance of the subtypes in the node-negative population. All models that included subtype and clinical variables were significantly better than either clinical alone (P<0.0001) or subtype alone (P<0.0001). A relapse classifier was trained to predict outcomes within the context of the intrinsic subtypes and clinical variables. A node-negative, no systemic treatment cohort (n=141) was selected from the van de Vijver et al. (2002) microarray data set to train the Subtypes and Prediction of Response to Neoadjuvant T/FAC Treatment The Hess et al. (2006) study that performed microarray on tumors from patients treated with T/FAC allowed investigation of the relationship between the subtypes and clinical markers and how each relates to pCR>. Table 14 shows the multivariable analyses of the subtypes together with clinical molecular markers (ER. PR, HER2) and either with (model A) or without (model B) histologic grade. The only significant variables in the context of this study were the intrinsic subtypes. A 94% sensitivity and 97% negative predictive value was found for identifying nonresponders to chemotherapy when using the ROR-S model to predict pCR. The relationship between high-risk scores and a higher probability of pCR is consistent with the conclusion that indolent ER-positive tumors (LumA) are less responsive to chemotherapy. However, unlike ROR for prognosis, a plateau seems to be reached for the ROR versus probability of pCR, confirming the presence of significant chemotherapy resistance among the highest risk tumors.

TABLE 14

| | Model A | | Model B | | Model C | |
|---|---|---|---|---|---|---|
| | | | Models of neoadjuvant response | | | |
| Variable | Odds ratio | P | Odds ratio | P | Odds ratio | P |
| Basal-like* | 1.33 | 0.33 | 1.79 | 0.3 | 1.58 | 0.066 |
| HER-enriched* | 2.53 | 0.00012 | 3.25 | <0.0001 | 2.9 | <0.0001 |
| LumB* | 2.43 | <.0001 | 2.88 | <0.0001 | 2.54 | <0.0001 |
| ER Status† | 0.83 | 0.38 | 0.83 | 0.34 | 0.83 | 0.32 |
| PR Status† | 1.36 | 0.034 | 1.43 | 0.012 | 1.57 | 0.001 |
| Histologic grade‡ | 1.4 | 0.0042 | — | — | — | — |
| Full v. subtype§ | | <.0001 | | <0.0001 | | <0.0001 |
| Full v. clinical‖ | | <.0001 | | <0.0001 | | <0.0001 |

*Luminal A class used as reference state in multivariable analysis.
†Hazard ratios for ER, PR and HER2 are positive marker in the numerator.
‡Grade encoded as an ordinal variable with three levels.
§Significant P values indicate improved prediction relative to subtype alone.
‖Significant P values indicate improved prediction relative to clinical data alone.

Example 4

In this study, qRT-PCR and previously established cut points (see Example 1) was used to assess the prognostic value of the PAM50 classifier in the common, clinically-important group of women who are estrogen receptor positive and treated with tamoxifen as their sole adjuvant systemic therapy. Unlike in most previous reports, this homogeneously-treated study cohort includes a large proportion of lymph node positive patients. The available detailed long term follow-up permits assessment not only of relapse-free survival, but also of the risk of breast cancer disease-specific death, in comparison with all standard clinicopathologic risk factors.

Methods

Patients:

The study cohort is derived from female patients with invasive breast cancer, newly diagnosed in the province of British Columbia in the period between 1986 and 1992. Tissue had been excised at various hospitals around the province, frozen and shipped to the central estrogen receptor (ER) laboratory at Vancouver Hospital; the portion of the received material that was formalin-fixed and paraffin-embedded as a histological reference is used in this study. Clinical information linked to the specimens includes age, histology, grade, tumor size, number involved axillary nodes, lymphatic or vascular invasion, ER status by the DCC method, type of local and initial adjuvant systemic therapy, dates of diagnosis, first local, regional or distant recurrence, date and cause of death. Characteristics of this patient cohort have been previously described in detail in a population-based study validating the prognostic model ADJUVANT! [Olivotto 2005], and the same source blocks were used to assemble tissue microarrays that have been characterized for ER [Cheang 2006] and HER2 [Chia 2008] expression. For this study, patients were selected who had ER positive tumors by immunohistochemistry, and received tamoxifen as their sole adjuvant systemic therapy. During the time period when these patients received their treatment, provincial guidelines recommended adjuvant tamoxifen for post-menopausal women, with ER-positive tumors who had some high risk features present such as lymphovascular invasion. Similar patients without high risk features were mainly treated without adjuvant systemic therapy. In most cases, chemotherapy was only offered to premenopausal women.

RNA Preparation:

RNA was isolated from pathologist-guided tissue cores. Briefly, H&E sections from each block were reviewed by a pathologist. Areas containing representative invasive breast carcinoma were selected and circled on the source block. Using a 1.0 mm punch needle, at least two tumor cores were extracted from the circled area. RNA was recovered using the High Pure RNA Paraffin Kit (Roche Applied Science, Indianapolis Ind.), DNA removed with Turbo Dnase (Ambion, Austin Tex.), and RNA yield assessed using an ND-1000 Spectrophotometer (Nanoprop Technologies, Rockland Del.).

qRT-PCR:

cDNA synthesis was done using a mixture of random hexamers and gene-specific primers, and qPCR was performed with the Roche LightCycler 480 instrument as previously described [Mullins 2007]. Each 384-well plate contained samples in duplicate (2.5 ng cDNA per reaction) and a calibrator in triplicate (10 ng cDNA per reaction). A tumor sample was considered of insufficient quality if any of the reference controls (ACTB, PSMC4, RPLP0, MRPL19, or SF3A1) failed. PCR was technically successful for all 50 discriminator genes in 73% of cases, and for 49 of the 50 in another 15% of cases. To assess the tolerance of the PAM50 assay results to missing gene information, ROR-C values were assessed in the data following random simulated removal of an increasing number of genes. Loss of one gene resulted in a 0-2 unit change in risk score, corresponding to a 1% increase/decrease in disease-specific survival at 10 years.

Assignment of Biological Subtype to Clinical Samples:

Gene expression centroids corresponding to Luminal A, Luminal B, HER2-enriched, Basal-like and Normal-like subtypes were constructed using the intrinsic 50 gene panel as described in Example I and in Parker et al. (2009 J. Clin. Oncol. 27(8):1160-7, which is herein incorporated by reference in its entirety). Specimens were assigned to an intrinsic subtype based on the nearest centroid distance calculated by Spearman's rank correlation, by investigators blinded to outcome data.

Relation of PAM50 Subtype to Clinical Outcome:

Statistical analyses were conducted using SPSS v16.0 and R v2.8.0. Univariate analysis of tumor subtype against breast cancer distant relapse-free and breast cancer disease-specific survival was performed by Kaplan-Meier analysis, with log rank test for significance. Multivariate analysis was performed against the standard clinical parameters of tumor size, nodal status (% positive nodes over total examined), histologic grade, patient age and HER2 status (based on adjacent cores from the same source block, assembled into tissue microarrays and subjected to immunostaining and FISH analysis using clinical-equivalent protocols [Chia 2008]). Cox regression models [Cox 1984] were built to estimate the adjusted hazard ratios of the qPCR-assigned breast cancer subtypes [Truong 2005]. Only cases with information for all the covariates were included in the analysis. Smoothed plots of weighted Schoenfeld residuals were used to assess proportional hazard assumptions [Grambsch 1994].

Relation of Risk-Of-Relapse (ROR) Score to Clinical Outcome:

The ROR score algorithm (ROR-S incorporating a sample's correlation to the Luminal A, Luminal B, HER2-enriched, and Basal-like subtypes; ROR-C incorporating this information plus tumor size) was trained and validated on three microarray-profiled and one qPCR-profiled breast cancer series. Risk stratification cutpoints were assigned in the training set such that no Luminal A patients fell into the high risk category, and no Basal-like patients fell into the low risk category. Kaplan-Meier and Cox regression analyses were conducted as above.

Results

From surgical specimens which had been formalin-fixed and paraffin embedded 15-20 years previously, tumor cores were extracted from pathologist-identified areas of invasive breast carcinoma for 991 cases. Following RNA extraction, 815 samples yielded at least 1.2 µg total RNA at a concentration of at least 25 ng/µL, and proceeded to PCR analysis. Template was of technically sufficient quality (based on internal housekeeper gene controls) for qRT-PCR in 806. Among these cases, a total of 711 specimens yielded high quality qRT-PCR quantitative data for at least 49 of the PAM50 discriminator genes, and were included in subsequent clinical and survival analyses. Clinical characteristics for these 711 patients are presented in Table 15.

TABLE 15

| Clinical Parameter | | Whole TAM series | Luminal A | Luminal B | Her2 | Basal | Normal |
|---|---|---|---|---|---|---|---|
| Sample Size | N | 711 | 329 | 312 | 58 | 3 | 9 |
| Age (in years) | Median [IQR] | 67 | 67 | 68 | 66 | 65 | 66 |
| Pre-menopausal | Yes | 18 | 9 | 7 | 2 | 0 | 0 |
| | No | 678 | 315 | 297 | 56 | 3 | 7 |
| | Unknown/Pregnant | 15 | 5 | 8 | 0 | 0 | 2 |
| Surgery | Complete Mastectomy | 428 | 187 | 196 | 36 | 3 | 6 |
| | Partial Mastectomy | 274 | 139 | 111 | 21 | 0 | 3 |
| | Other | 9 | 3 | 5 | 1 | 0 | 0 |
| Axillary Node Dissection | Yes | 675 | 308 | 298 | 57 | 3 | 9 |
| | No | 36 | 21 | 14 | 1 | 0 | 0 |
| Breast/chest wall radiation therapy | Yes | 372 | 180 | 153 | 34 | 0 | 5 |
| | No | 339 | 149 | 159 | 24 | 3 | 4 |
| Adjuvant Tamoxifen | Yes | 711 | 329 | 312 | 58 | 3 | 9 |
| | No | 0 | 0 | 0 | 0 | 0 | 0 |
| Adjuvant Chemo-therapy | Yes | 0 | 0 | 0 | 0 | 0 | 0 |
| | No | 711 | 329 | 312 | 58 | 3 | 9 |
| Tumor Size (cm) | Median [IQR] | 2.2 | 2.0 | 2.5 | 2.5 | 2.5 | 3.0 |
| T Stage (Clinical) | T0/IS | 0 | 0 | 0 | 0 | 0 | 0 |
| | T1 | 298 | 155 | 113 | 24 | 3 | 3 |
| | T2 | 346 | 147 | 169 | 27 | 0 | 3 |
| | T3 | 18 | 10 | 5 | 3 | 0 | 0 |
| | T4 | 28 | 9 | 15 | 1 | 0 | 3 |
| | TX | 21 | 8 | 10 | 3 | 0 | 0 |
| #Positive Nodes | 0 | 199 | 83 | 91 | 18 | 0 | 7 |
| | 1-3 | 328 | 162 | 139 | 24 | 1 | 2 |
| | 4-9 | 111 | 49 | 51 | 10 | 1 | 0 |
| | 10+ | 26 | 8 | 16 | 2 | 0 | 0 |
| | Unknown | 47 | 27 | 15 | 4 | 1 | 0 |
| Grade | Grade 1: well differentiated | 24 | 20 | 2 | 1 | 0 | 1 |
| | Grade 2: moderately differentiated | 306 | 169 | 119 | 13 | 0 | 5 |
| | Grade 3: poorly differentiated | 338 | 117 | 173 | 43 | 2 | 3 |
| | Unknown | 43 | 23 | 18 | 1 | 1 | 0 |

TABLE 15-continued

| Clinical Parameter | | Whole TAM series | Luminal A | Luminal B | Her2 | Basal | Normal |
|---|---|---|---|---|---|---|---|
| histologic | ductal NOS | 642 | 289 | 288 | 54 | 3 | 8 |
| subtype | lobular | 54 | 30 | 19 | 4 | 0 | 1 |
| | mucinous | 7 | 4 | 3 | 0 | 0 | 0 |
| | tubular | 5 | 5 | 0 | 0 | 0 | 0 |
| | medullary | 2 | 1 | 1 | 0 | 0 | 0 |
| | apocrine | 1 | 0 | 1 | 0 | 0 | 0 |
| Lymphovascular | Yes | 444 | 184 | 215 | 39 | 1 | 5 |
| invasion | No | 230 | 122 | 84 | 18 | 2 | 4 |
| | Unknown | 37 | 23 | 13 | 1 | 0 | 0 |
| Clinical | missing | 6 | 4 | 2 | 0 | 0 | 0 |
| estrogen | negative (0-9 | 9 | 3 | 2 | 4 | 0 | 0 |
| receptor status | fmol/mg) | | | | | | |
| (DCC) | Positive (>10 | 696 | 322 | 308 | 54 | 3 | 9 |
| | fmol/mg) | | | | | | |
| Immunohisto- | negative | 0 | 0 | 0 | 0 | 0 | 0 |
| chemical ER | positive | 711 | 329 | 312 | 58 | 3 | 9 |

Based on the nearest PAM50 centroid, a total of 329 (46.3%) of these clinically ER positive cases were assigned as Luminal A, 312 (43.8%) as Luminal B, 58 (8.2%) as HER2-enriched, 3 (0.4%) as Basal-like, and 9 (1.3%) as Normal-like intrinsic breast cancer subytpes by gene expression (Table 13). For the nine cases assigned as Normal-like, the histology was reviewed, using the tissue microarray cores taken from the same area of the source block. In eight of these nine cases, viable invasive cancer cells were absent or rare in an immediately adjacent core, consistent with the normal-like expression profile representing an inadequate tumor sampling. Normal-like cases were therefore excluded from further analysis.

Figures 4A, 4B:
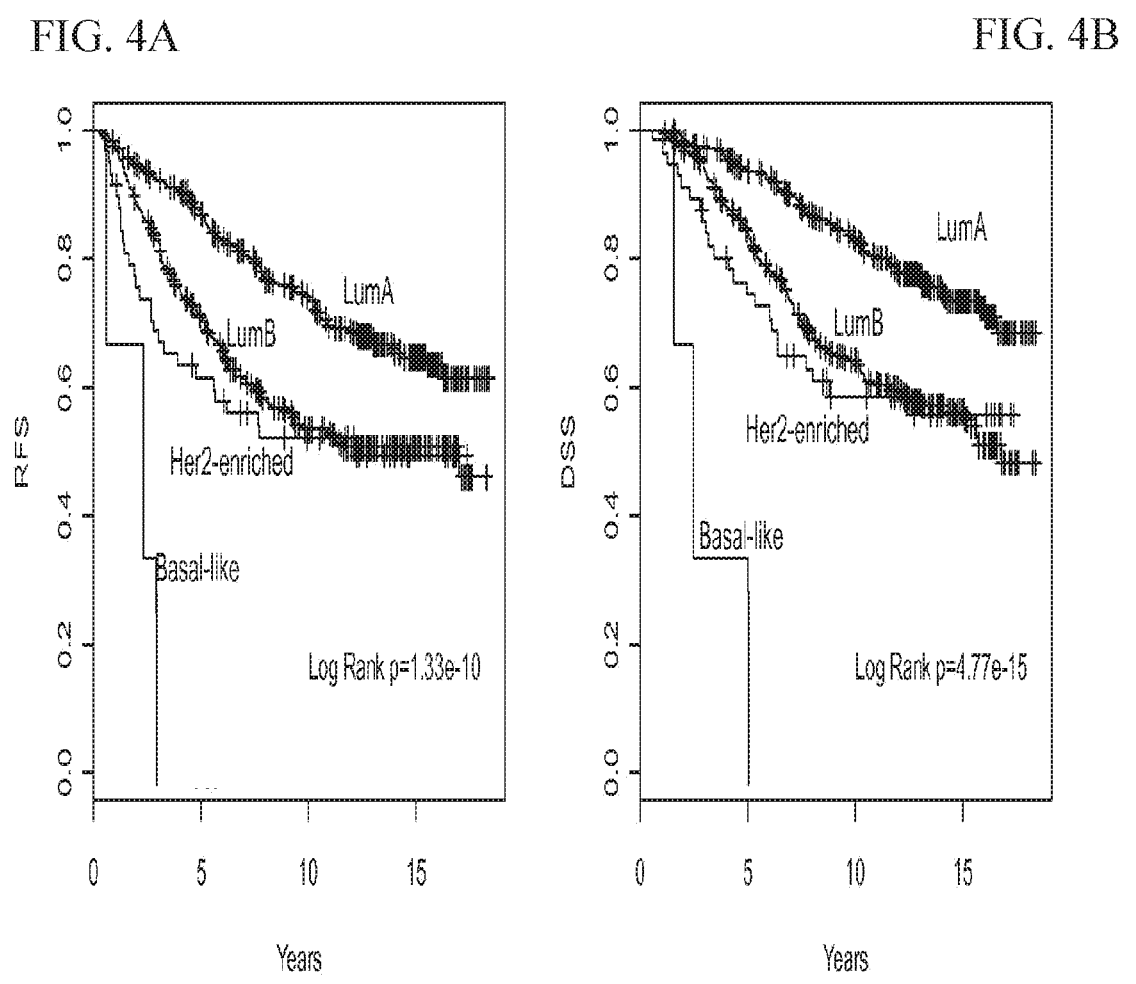

Intrinsic biological subtype was strongly prognostic by Kaplan-Meier analysis (FIGS. 4A and 4B). In the British Columbia population at the time of sample acquisition for this study, many patients with a clinically low risk profile received no adjuvant systemic therapy [Olivotto 2005]. In contrast, those receiving adjuvant tamoxifen who are the subjects in this study comprised a higher clinical risk group, with overall 10 year distant relapse-free survival rates of 62% and breast cancer disease-specific survival rates of 72%. Those determined by the PAM50 assay to have a Luminal A profile had a significantly better outcome (10 year relapse free survival 74%, disease-specific survival=83%) than Luminal B, HER2-enriched or basal like tumors.

All cases in this study were positive for estrogen receptor by centrally-assessed immunohistochemistry [Cheang 2006], and 98.7% were also positive by clinical dextran-charcoal coated biochemical assay. Despite this, the PAM50 qPCR panel assigned 10% of cases to non-luminal subtypes, mostly HER2-enriched, as was previously observed when interrogating published datasets for expression of the PAM50 genes (Example 2).

For this cohort of clinically estrogen receptor positive women, uniformly treated with tamoxifen as their sole adjuvant systemic therapy, a multivariable Cox model was constructed to test the independent value of PAM50 subtype against patient age and the standard clinicopathologic factors of tumor size, nodal status, histologic grade and HER2 expression (Table 16). Intrinsic biological subtype remained significant in the multivariable model, as were nodal status and tumor size, but grade and clinical HER2 status, significant in univariate analysis in this cohort, did not contribute significant independent prognostic information for either relapse-free or disease-specific survival in the multivariate model incorporating the PAM50 result.

TABLE 16

Cox model univariate and multivariate analyses incorporating PAM50 biological subtype for relapse-free and breast cancer disease-specific survival among (A) 604 women with ER positive, tamoxifen-treated breast cancer with complete data for all covariates for relapse-free survival, and (B) breast cancer disease-specific survival (BCDSS; excludes 2 cases with unknown cause of death).

| Clinical endpoint | hazard ratio (95% CI) univariate relapse-free survival | p-value | hazard ratio (95% CI) multivariate relapse-free survival | p-value |
|---|---|---|---|---|
| age (continuous) | 1.00 (0.990-1.02) | 0.53 | 0.996 (0.981-1.01) | 0.62 |
| grade (1 or 2) vs. 3 | 1.45 (1.12-1.89) | 0.0047 | 1.11 (0.846-1.46) | 0.45 |
| percent nodes positive | | | | |
| 0 vs. (>0 to <25%) | 1.66 (1.15-2.39) | 0.0070 | 1.76 (1.22-2.55) | 0.0028 |
| 0 vs. ≥25% | 2.98 (2.10-4.22) | 7.3E−10 | 2.85 (2.00-4.06) | 6.3E−9 |
| tumor size ≤2 cm vs. >2 cm | 2.02 (1.55-2.65) | 2.5E−7 | 1.71 (1.30-2.24) | 1.3E−4 |

TABLE 16-continued

Cox model univariate and multivariate analyses incorporating PAM50 biological subtype for relapse-free and breast cancer disease-specific survival among (A) 604 women with ER positive, tamoxifen-treated breast cancer with complete data for all covariates for relapse-free survival, and (B) breast cancer disease-specific survival (BCDSS; excludes 2 cases with unknown cause of death).

| | | | | |
|---|---|---|---|---|
| HER2 (IHC) {0, 1 or 2+ FISH negative} vs. {2+ FISH positive, or 3+} PAM50 subtype | 1.52 (1.04-2.23) | 0.032 | 1.24 (0.813-1.88) | 0.32 |
| Luminal A vs. Luminal B | 1.73 (1.31-2.28) | 1.0E−4 | 1.62 (1.22-2.16) | 9.2E−4 |
| Luminal A vs. Her2-Enriched | 1.86 (1.18-2.92) | 0.0074 | 1.53 (0.929-2.52) | 0.095 |
| Luminal A vs. Basal-like | 76.4 (9.79-597) | 3.5E−5 | 62.5 (7.87-496) | 9.2E−5 |

| B. | | | | |
|---|---|---|---|---|
| Clinical endpoint | hazard ratio (95% CI) | p-value | hazard ratio (95% CI) | p-value |
| | Univariate BCDSS | | Multivariate BCDSS | |
| age (continuous) | 1.02 (0.999-1.03) | 0.069 | 1.01 (0.988-1.02) | 0.56 |
| grade (1 or 2) vs. 3 | 1.43 (1.07-1.91) | 0.015 | 1.05 (0.988-1.02) | 0.76 |
| percent nodes positive | | | | |
| 0 vs. (>0 to <25%) | 1.56 (1.03-2.37) | 0.034 | 1.68 (1.11-2.56) | 0.015 |
| 0 vs. ≥25% | 3.22 (2.19-4.73) | 2.4E−9 | 3.04 (2.06-4.48) | 2.3E−8 |
| tumor size ≤2 cm vs. >2 cm | 2.29 (1.96-3.10) | 8.0E−8 | 1.90 (1.40-2.58) | 4.3E−8 |
| HER2 (IHC) {0, 1 or 2+ FISH negative} vs. {2+ FISH positive, or 3+} PAM50 subtype | 1.54 (1.01-2.35) | 0.043 | 1.19 (0.755-1.86) | 0.46 |
| Luminal A vs. Luminal B | 2.05 (1.50-2.80) | 6.0E−6 | 1.90 (1.37-2.62) | 1.0E−4 |
| Luminal A vs. Her2-Enriched | 2.2 (1.33-3.64) | 0.0021 | 1.85 (1.07-3.20) | 0.028 |
| Luminal A vs. Basal-like | 104 (13.1-832) | 1.2E−5 | 91.1 (11.2-743) | 2.5E−5 |

A risk-of-relapse (ROR) score can be calculated from the PAM50 qPCR panel. Both the ROR-S (based only on molecular subtyping from the PAM50 panel) and ROR-C (combining subtype and tumor size information) scores are highly prognostic in a population homogeneously treated with adjuvant tamoxifen, to a series containing large numbers of node positive cases, and to the endpoint of breast cancer-specific survival (FIGS. 5A and 5B).

As shown in FIGS. 6A and 6B, the ROR-C algorithm is not only highly prognostic among node negative patients, but reveals even wider differences in disease-specific survival among node positive patients. The algorithm identifies 16% of clinically ER positive patients (treated with adjuvant tamoxifen but not chemotherapy) who, despite being node positive, are classed as low risk, and these women have a 10 year disease-specific survival rate of 89%.

As a continuous variable, ROR-C has a significant interaction with percentage of positive lymph nodes, and borderline significant interaction with nodal stage (Table 17). Nodal stage is a significant predictor among patients with moderate to high ROR-C values (>23.5), but among patients with low ROR-C scores, outcomes are good regardless of nodal status (FIGS. 7A to 7D and FIG. 8).

TABLE 17 Interaction test between PAM50- and tumor size-derived ROR-C score, expressed as a continuous variable, and axillary lymph node status (A) expressed as % positive nodes or (B) categorized by nodal stage (where referent group is node negative, N cat2=1-3 involved axillary nodes, and N cat3=4 or more involved axillary nodes).

The model in Table 17A uses the proportion of positive nodes and the interaction is significant. The model in Table 17B uses 3 level node status (N—, 1-3 pos, >3 pos) and interaction is borderline.

TABLE 17A

| Variable | Only main effects | | Interaction | |
|---|---|---|---|---|
| | Hazard | p-value | Hazard | p-value |
| ROR-C | 1.75 | 1.60E−11 | 1.73 | 8.8E−11 |
| Pos Node % | 1.56 | 2.50E−10 | 1.43 | 0.000017 |
| Interaction | | | 1.17 | 0.043 |
| Full vs red | | | | 0.04 |

TABLE 17B

| Variable | Only main effects | | Interaction | |
|---|---|---|---|---|
| | Hazard | p-value | Hazard | p-value |
| ROR-C | 1.77 | 6.20E−11 | 1.52 | 0.018 |
| N cat2 | 1.8 | 9.40E−03 | 1.73 | 0.022 |

TABLE 17B-continued

| Variable | Only main effects | | Interaction | |
|---|---|---|---|---|
| | Hazard | p-value | Hazard | p-value |
| N cat3 | 3.88 | 1.20E−08 | 3.15 | 1.40E−05 |
| ROR*N cat2 | | | 1.08 | 0.71 |
| ROR*N cat3 | | | 1.62 | 0.061 |
| Full vs red | | | | 0.11 |

As ROR-C includes tumor size information, to assess if the ROR algorithm gives independent additional prognostic information beyond standard clinical parameters (including tumor size) in this patient population, Cox models incorporating ROR-S were tested (Table 18). Regardless of whether the endpoint is relapse-free or disease-specific survival, or if ROR-S is included as a categorical or as a continuous variable, it remains significant, whereas grade and clinical HER2 status are not significant in multivariate analyses that include the qPCR-derived information.

TABLE 18

Cox model multivariate analysis incorporating ROR-S score for breast cancer disease-specific survival among women with ER positive, tamoxifen-treated breast cancer and complete data for all covariates. (A) ROR-S-defined risk categories, using prespecified cutpoints. (B) ROR-S as a continuous variable.

A.

| Clinical endpoint | hazard ratio (95% C.I.) relapse-free survival (N = 613) | p-value | hazard ratio (95% C.I.) disease-specific survival (N = 611) | p-value |
|---|---|---|---|---|
| age (continuous) | 0.995 (0.980-1.01) | 0.56 | 1.00 (0.988-1.02) | 0.56 |
| grade (1 or 2) vs. 3 percent nodes positive | 1.03 (0.785-1.36) | 0.81 | 1.00 (0.738-1.36) | 1.0 |
| 0 vs. (>0 to <25%) | 1.79 (1.24-2.58) | 0.0016 | 1.74 (1.16-2.63) | 0.0081 |
| 0 vs. ≥25% | 2.87 (2.02-4.08) | 4.4E−9 | 3.10 (2.10-4.57) | 1.3E−8 |
| tumor size ≤2 cm vs. >2 cm | 1.70 (1.30-2.23) | 1.2E−4 | 1.92 (1.42-2.61) | 2.8E−5 |
| HER2 (IHC) {0, 1 or 2+ FISH negative} vs. {2+ FISH positive, or 3+} ROR-S (categorized) | 1.14 (0.760-1.72) | 0.52 | 1.10 (0.701-1.74) | 0.67 |
| low vs. medium | 2.00 (1.39-2.87) | 1.9E−4 | 2.21 (1.45-3.36) | 2.1E−4 |
| low vs. high | 2.68 (1.63-4.41) | 1.0E−4 | 3.25 (1.86-5.67) | 3.4E−5 |

TABLE 18-continued

Cox model multivariate analysis incorporating ROR-S score for breast cancer disease-specific survival among women with ER positive, tamoxifen-treated breast cancer and complete data for all covariates. (A) ROR-S-defined risk categories, using prespecified cutpoints. (B) ROR-S as a continuous variable.

| | B. | | | |
|---|---|---|---|---|
| Clinical endpoint | hazard ratio (95% C.I.) relapse-free survival (N = 613) | p-value | hazard ratio (95% C.I.) disease-specific survival (N = 611) | p-value |
| age (continuous) | 0.997 (0.982-1.01) | 0.71 | 1.01 (0.989-1.02) | 0.48 |
| grade (1 or 2) vs. 3 percent nodes positive | 1.06 (0.808-1.40) | 0.66 | 1.02 (0.749-1.38) | 0.92 |
| 0 vs. (>0 to <25%) | 1.77 (1.23-2.53) | 0.0021 | 1.71 (1.13-2.58) | 0.011 |
| 0 vs. ≥25% | 2.87 (2.02-4.06) | 3.4E−9 | 3.12 (2.12-4.59) | 8.5E−9 |
| tumor size ≤2 cm vs. >2 cm | 1.70 (1.30-2.23) | 1.2E−4 | 1.92 (1.41-2.60) | 3.0E−5 |
| HER2 (IHC) {0, 1 or 2+ FISH negative} vs. {2+ FISH positive, or 3+} | 1.05 (0.699-1.59) | 0.80 | 0.986 (0.628-1.55) | 0.95 |
| ROR-S (continuous) | 1.02 (1.01-1.03) | 7.3E−5 | 1.02 (1.01-1.03) | 1.0E−5 |

The cases in this series have previously been assessed by immunohistochemistry for ER, PR, HER2, cytokeratin 5/6, epidermal growth factor receptor, and Ki67 [Cheang 2008] [Cheang 2009], allowing intrinsic subtyping to be assigned by a surrogate immunohistochemical definition. As all cases in this series are ER positive by immunohistochemistry, all were assigned as either Luminal A (if HER2 negative and Ki67 low) or Luminal B (if HER2 positive or Ki67 high). The availability of qPCR subtyping assignments allows a comparison with immunohistochemical assignment on the same material, against patient outcome in this homogeneously-treated cohort. A total of 606 cases had sufficiently complete immunohistochemical and qPCR data for assignment to a Luminal subtype by both methods. Among these, 255 were assigned as Luminal A and 193 as Luminal B by both methods, whereas 99 were assigned Luminal A by immunostain but Luminal B by qPCR, and 59 as Luminal B by immunostain but Luminal A by qPCR, for a concordance of 74%, kappa-0.48. Where the results were discordant, only the cases assigned as Luminal B by PCR had significantly poorer outcome than those concordantly assigned as Luminal A. In multivariable analysis among these cases, both immunohistochemical and PAM50 assignment are independently significant predictors for relapse-free survival, whereas grade and HER2 status fall out of the model (Table 19). For disease-specific survival, PAM50 is significant whereas immunohistochemistry is borderline. The magnitude of the identified hazard is higher with the qPCR assignment for both endpoints. In a step-wise Cox regression model incorporating both immunohistochemical and qPCR assignment, only qPCR stays significant.

TABLE 19

Cox model multivariate analyses for Luminal cases, comparing the prognostic information from intrinsic subtyping by immunohistochemistry versus PAM50 qPCR.

| | hazard ratio (95% CI) | p-value | hazard ratio (95% CI) | p-value |
|---|---|---|---|---|
| | A. Relapse-free survival (N = 606) | | | |
| Clinical endpoint | immunohistochemical subtype | | PAM50 qPCR subtype | |
| age (continuous) | 0.992 (0.98-1.01) | 0.36 | 0.990 (0.97-1.01) | 0.26 |
| grade (1 or 2) vs. 3 percent positive nodes | 1.18 (0.89-1.57) | 0.24 | 1.12 (0.84-1.49) | 0.43 |
| 0 vs. (>0 to <25% | 1.66 (1.11-2.48) | 0.014 | 1.68 (1.12-2.50) | 0.012 |
| 0 vs. ≥25% | 2.86 (1.95-4.19) | 7.2E−8 | 2.93 (2.00-4.30) | 3.8E−8 |
| tumor size ≤2 cm vs. >2 cm | 1.80 (1.34-2.42) | 8.6E−5 | 1.81 (1.35-2.42) | 7.4E−5 |

TABLE 19-continued

Cox model multivariate analyses for Luminal cases, comparing the prognostic
information from intrinsic subtyping by immunohistochemistry versus PAM50 qPCR.

| | hazard ratio (95% CI) | p-value | hazard ratio (95% CI) | p-value |
|---|---|---|---|---|
| HER2 (IHC) {0, 1, or 2+ FISH negative} vs. {2+ FISH positive or 3+} | 1.21 (0.74-1.99) | 0.45 | 1.30 (0.81-2.09) | 0.27 |
| Luminal B vs. Luminal A | 1.38 (1.02-1.86) | 0.035 | 1.61 (1.20-2.16) | 0.0014 |

B. Breast cancer disease-specific survival (N = 605; excludes one death of uncertain cause)

| Clinical endpoint | immunohistochemical subtype | | PAM50 qPCR subtype | |
|---|---|---|---|---|
| age (continuous) | 1.00 (0.98-1.02) | 0.67 | 1.00 (0.98-1.02) | 0.89 |
| grade (1 or 2) vs. 3 | 1.14 (0.83-1.55) | 0.42 | 1.05 (0.77-1.44) | 0.74 |
| percent positive nodes | | | | |
| 0 vs. (>0) to <25% | 1.44 (0.92-2.26) | 0.106 | 1.50 (0.96-2.34) | 0.077 |
| 0 vs. ≥ 25% | 2.79 (1.84-4.23) | 1.2E−6 | 2.88 (1.90-4.38) | 5.8E−7 |
| tumor size ≤2 cm vs. >2 cm | 2.07 (1.48-2.89) | 1.8E−5 | 2.06 (1.48-2.87) | 1.7E−5 |
| HER2 (IHC) {0, 1, or 2+ FISH negative} vs. {2+ FISH positive or 3+} | 1.27 (0.75-2.15) | 0.38 | 1.29 (0.78-2.13) | 0.32 |
| Luminal B vs. Luminal A | 1.38 (0.99-1.93) | 0.060 | 1.89 (1.36-2.62) | 1.5E−4 |

Results from Adjuvant! Predictions

A comparison of the outcome predicted by the Adjuvant! model with outcome predicted by the ROR model was made in a cohort of breast cancer patients. This cohort consists of 806 patients diagnosed with invasive, estrogen receptor positive breast cancer, between the dates of 1986 and 1992. All patients had primary surgery and adjuvant systemic therapy with tamoxifen alone; none of these patients were treated with chemotherapy. The Adjuvant prognostic model was used to calculate the probability of breast cancer specific survival (BCSS) at 10 years using the standard clinicopathological features of patient age, tumor size, histological grade, lymphovascular invasion, and number of positive lymph nodes. All patients were ER positive, and the risk of breast cancer death was adjusted for adjuvant tamoxifen therapy.

Of the 806 patients, 748 had sufficient clinicopathological data to obtain an Adjuvant estimate of BCSS. The remaining 58 patients had either missing tumor size or missing lymph node data. The mean Adjuvant predicted BCSS was 73.7%. This corresponds to the observed BCSS of 73.2%. The cohort was then divided into subgroups based on the Adjuvant predicted BCSS at 10 years (Table 20).

TABLE 20

| Risk Category | Adjuvant! Predicted 10-year BCSS | N | Number of Events |
|---|---|---|---|
| 1 | 90-100% | 122 | 16 |
| 2 | 80-90% | 164 | 32 |
| 3 | 70-80% | 168 | 60 |
| 4 | <70% | 292 | 121 |

The observed BCSS at 10 years, for each of the Adjuvant risk groups was similar to the BCSS predicted by Adjuvant (Table 21). One notable exception is the lowest risk group, in subgroup with an Adjuvant! predicted BCSS of 90-100%, the observed BCSS at 10 years is 89%. Consequently, it appears that Adjuvant is overestimating survival is this low risk group. This is consistent with the validation study of Adjuvant! using the BCOU database (Olivotto et al. (2005)). In this validation study, it was found that Adjuvant underestimated breast cancer deaths by 4.9% in the subgroup with T1N0 disease. In the subgroup of patients with a predicted BCSS of 90-100%, 87 of 122 patients had T1N0 breast cancer.

TABLE 21

| Adjuvant Risk Group | Mean Adjuvant Predicted BCSS at 10 years | Observed BCSS at 10 years |
|---|---|---|
| 90-100% | 94% | 89% |
| 80-90% | 85% | 83% |
| 70-80% | 76% | 75% |
| <70% | 58% | 61% |

ROR-S using qRT-PCR data from 50 genes was then used to separate each Adjuvant! group into low vs. medium/high risk (Table 22). Due to the relatively small size of each group, medium and high risk groups were combined to improve statistical power. Also, because the Adjuvant! risk subgroups are already defined using clinical factors, ROR-S (rather than ROR-C) was applied.

TABLE 22

| Adjuvant Risk Group | ROR-S Low | ROR-S Medium or High |
|---|---|---|
| 90-100% | 47 | 75 |
| 80-90% | 56 | 108 |

TABLE 22-continued

| Adjuvant Risk Group | ROR-S Low | ROR-S Medium or High |
|---|---|---|
| 70-80% | 43 | 125 |
| <70% | 58 | 234 |

Kaplan-Meier analysis was then performed separately on each Adjuvant risk group, and differences in survival between the low vs. med/high risk ROR-S groups were tested using the log-rank test (Table 23). It was observed that ROR-S could isolate a low risk subgroup in each of the Adjuvant Risk Groups. Statistically significant differences in BCSS were found for low risk vs. medium/high risk patients, in all subgroups except for the 90-100% group.

TABLE 23

| Adjuvant Risk Group | Observed BCSS | BCSS for Low Risk ROR-S | BCSS for Med/High Risk ROR-S | Log-rank Test of ROR-S |
|---|---|---|---|---|
| 90-100% | 89% | 93% | 85% | p = 0.058 |
| 80-90% | 83% | 92% | 78% | p = 0.020 |
| 70-80% | 75% | 95% | 68% | p = 0.005 |
| <70% | 61% | 71% | 58% | P = 0.009 |

Figure 9:
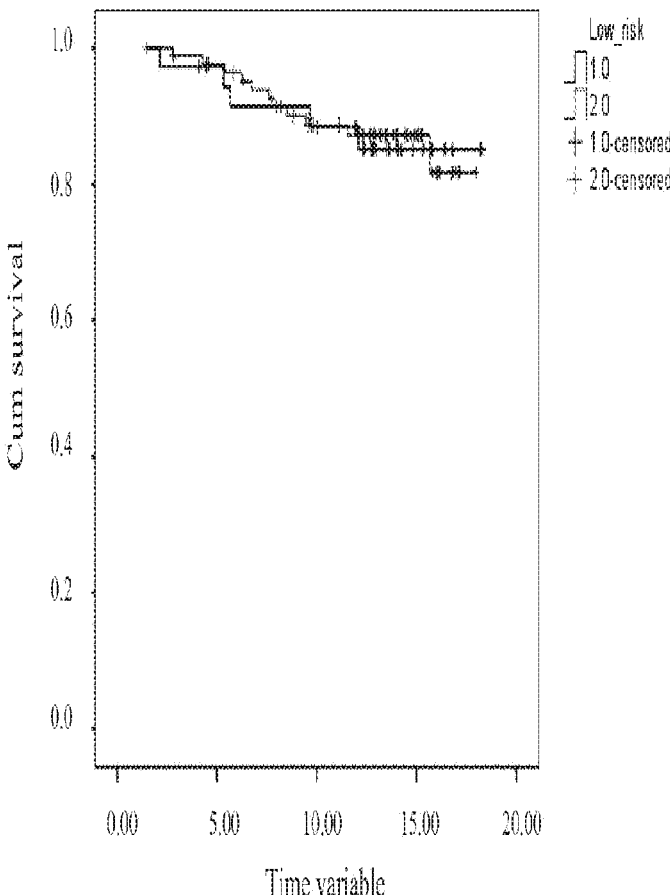
FIG. 9 shows the results of Kaplan-Meier analysis that was performed separately on each Adjuvant risk group, and differences in survival between the 90-95% and the 95-100% risk groups were tested using the log-rank test.

In this low risk group, ROR—S is not quite statistically significant (p=0.058). However, this group does provide some convincing evidence that the ROR-S is adding additional prognostic information to Adjuvant!. A Kaplan-Meier analysis of the same group but with Adjuvant! predicted BCSS 90-95% vs. 95-100% is shown in FIG. 9.

Figure 10A:
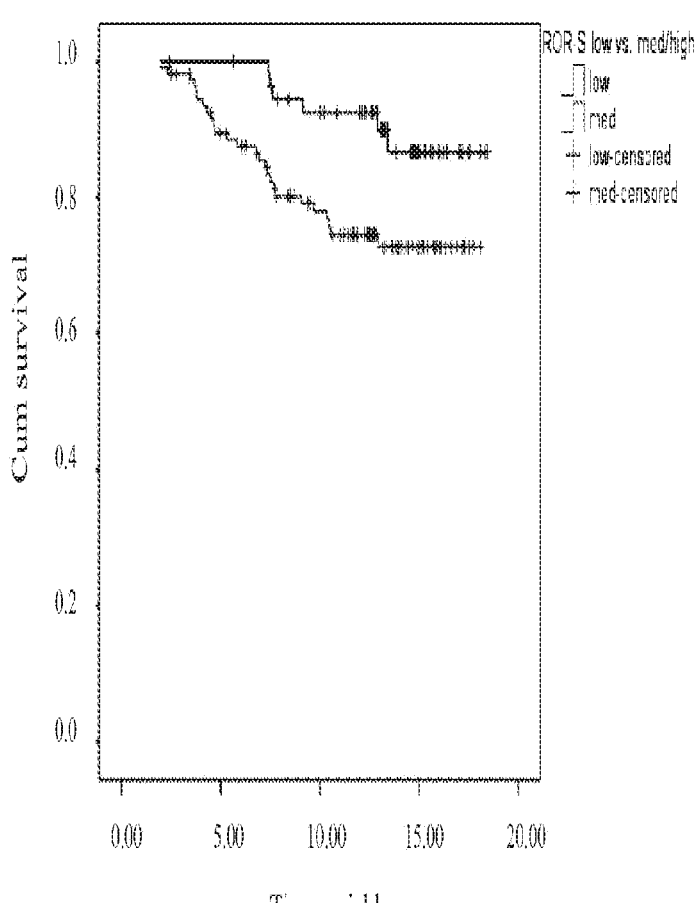
FIGS. 10A to 10C shows the results of Kaplan-Meier analysis that was performed separately on each Adjuvant risk group, and differences in survival between (FIG. 10A) the Adjuvant Predicted BCSS 80-90%, ROR-S Low vs. Med/High.
Figure 10B:
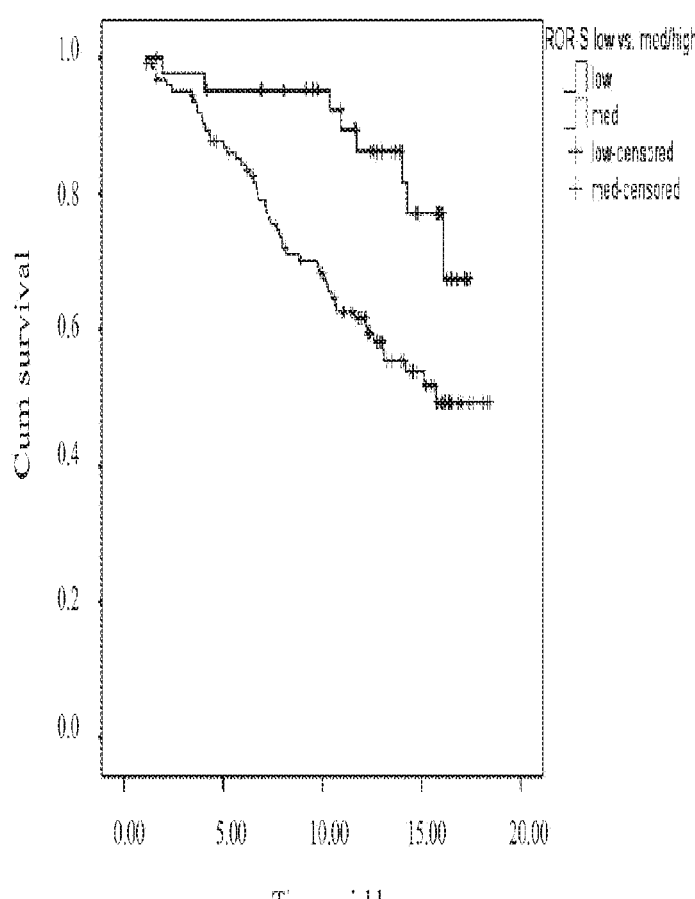

In the intermediate risk groups, ROR-S performs well in identifying low risk vs. higher risk patients. In both the 80-90% group (FIG. 10A) and 70-80% group (FIG. 10B), the ROR-S identifies subgroups with 10 year BCSS >90%. This is an important result as ROR-S identifies traditionally high-risk patients that do well without chemotherapy.

Figure 10C:
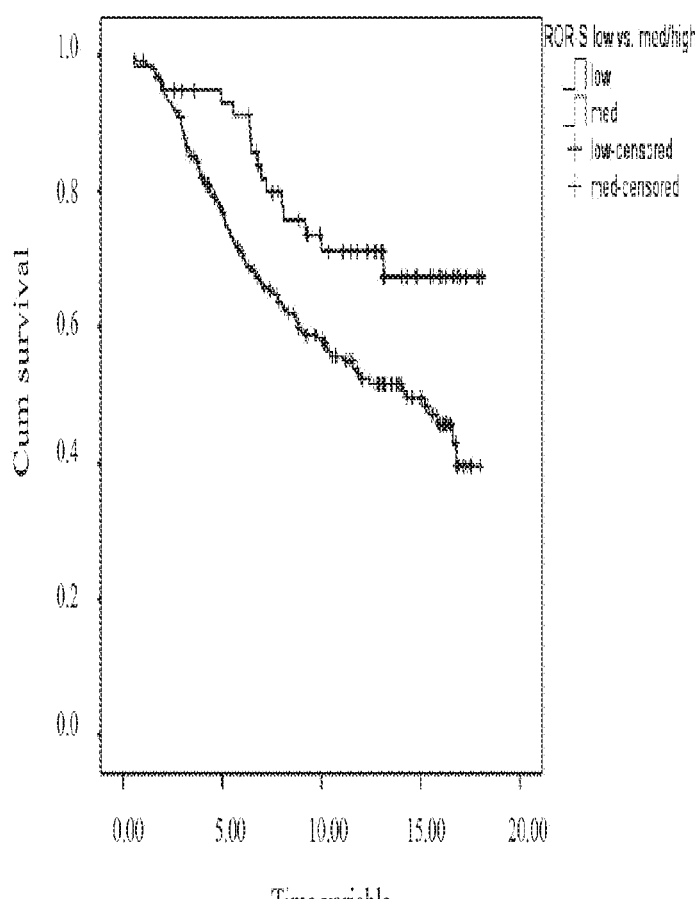

In the very high risk subgroup identified by Adjuvant! (Predicted BCSS <70%), ROR-S is still able to identify distinct prognostic groups (FIG. 10C).

Discussion

Previous studies have established that intrinsic biological signatures characteristic of Luminal A, Luminal B, HER2-Enriched and Basal-like subtypes are present and have prognostic significance in breast cancer cohorts from multiple different institutions, profiled with several gene expression microarray platforms [Calza 2006] [Kapp 2006] [Hu 2006] [Fan 2006]. In order to identify these subtypes on standard formalin-fixed, paraffin-embedded pathology specimens, a quantitative reverse-transcriptase PCR test [Mullins 2007] was developed that identifies these subtypes based on a panel of 50 genes.

The analysis reported here consists exclusively of qPCR-based testing, applied to a series of relatively old-age (15-20 years) paraffin blocks with long and detailed follow-up, allowing analysis not only of relapse-free survival, but also of breast cancer disease-specific survival. The present study consists of women with estrogen receptor positive breast cancer who received hormonal therapy (tamoxifen) as their sole adjuvant treatment, a group of particular clinical importance and contemporary relevance. Estrogen receptor and HER2 status were centrally determined. 70% of these women were node positive at presentation, and in current practice would usually be recommended to receive adjuvant chemotherapy. The PAM50 subtype assignment as determined by PCR is highly prognostic in these women. Subtype remains significant in multivariate analysis, whereas grade and clinical HER2 status do not. Findings using the commonly-employed surrogate endpoint of relapse-free survival all hold for breast cancer disease-specific survival.

Although the patients from this cohort were treated more than 20 years ago, the findings from this study remain relevant to the treatment of breast cancer patients with a moderate risk of relapse. Such patients may derive significant benefit from adjuvant hormonal therapy but the further addition of chemotherapy may have modest effects (2-5% improvement in 10-year relapse free survival). While the decision to pursue adjuvant chemotherapy is an individual decision made by the patient and consulting oncologist, improved prognostication will facilitate therapeutic decision making.

A Risk of Relapse score was developed and validated on microarray data from node negative patients who received no adjuvant systemic therapy (Example 2), against the endpoint of relapse-free survival. This algorithm is shown to predict pathologic complete response in a published neoadjuvant T/FAC clinical trial dataset of 133 patients, and, in its qPCR format, to predict relapse-free survival in a cohort of 279 heterogeneously-treated women with breast cancer. ROR scores generated by qPCR from paraffin block specimens are also prognostic in tamoxifen-treated, estrogen positive women, in both node-negative and node-positive subsets. ROR-C identifies a group of low risk patients among whom even nodal status is not a predictor, and who might therefore not require treatment approaches usually reserved for node positive patients including, for example, third generation chemotherapy regimens and chest wall radiation.

Very few cases (1.3%) are classified as Normal-like using the PCR assay, as compared to 12% when the PAM50 classifier is applied to DNA microarray data from large sets of primary breast cancers. DNA microarray analyses utilize homogenized tumor specimens that, despite gross dissection to enrich for tumor, may still contain significant amounts of normal breast tissue. In contrast, the PAM50 qPCR assay is performed on a pathologist-guided tissue core, based on direct microscopic identification of a representative area of pure tumor in the source block. This difference likely accounts for the much lower frequency of Normal-like profiles obtained using the PAM50 qPCR method applied to paraffin blocks. Review of the histology, as represented in tissue microarray cores extracted from the immediately adjacent tissue, is consistent with inadequate tumor representation being responsible for a normal-like profile in eight of the nine normal-like cases.

As was previously noted based on interrogation of published datasets with the PAM50 classifier, this assay identifies ER-negative biological subtypes among clinically ER positive women even in a setting where the tumor is positive by both immunohistochemical and ligand-binding assays. Fully 10% of cases are re-assigned to non-luminal subtypes, and these tamoxifen-treated women had poor outcomes, compatible with a biological reality of hormone independence. Clinical measurements of ER and HER2 status, on their own, can stratify breast cancer patients into prognostic and predictive subgroups [Hayes 2007]. Nevertheless, relying on measurements of single genes (ER, PR) to assign breast cancer prognosis and treatment risks not only the problems of false positive and negative single measurements, but also the possibility that a tumor's underlying biology may be hormone independent (despite one member of the pathway being expressed at the protein level). In this respect, the information provided by concurrently measuring 50 genes, including others in the estrogen response pathway together with positive markers of other biological subtypes, is likely to be a more accurate reflection of the underlying tumor biology [Oh 2006].

Larger immunohistochemical surrogate panels have been linked to expression profile gold standards and can provide more information than simple measurement of ER, PR and HER2 [Cheang 2008b] [Cheang 2009]. Limited antibody panels are easily applied to standard paraffin blocks, and can add significant prognostic information beyond standard clinicopathologic risk factors [Ross 2008]. In this study, a direct comparison of an established six immunostain panel (ER, PR, HER2, Ki67, cytokeratin 5/6 and epidermal growth factor receptor) against the 50 gene qPCR assay, was made using the same source blocks. Each method adds significant prognostic information beyond standard factors. However, in this set of clinically ER positive patients, there were many discrepant assignments to an intrinsic biological subtype, and the qPCR approach was better at predicting outcome in these cases.

In multivariate analysis incorporating the main clinical risk factors, grade is no longer significant when PAM50 subtype or ROR is included. In comparison with other signatures such as the recurrence score and genomic grade indexes [Paik 2004] [Ivshina 2006] [Sotiriou 2006], the PAM50 also has the advantage of discriminating high risk cases into Luminal B, HER2-Enriched and Basal-like sub-types, who are likely to respond differently to systemic therapy options (for example, hormonal, anti-HER2, and anthracycline vs. non-anthracycline chemotherapy regimens). The assay is also easier to perform, as it does not require frozen tissue [Glas 2006] nor manual microdissection of cut sections [Paik 2004] and can be readily applied to standard paraffin blocks including archival tissues such as those from clinical trials. However, the assay can be performed on these types of samples if desired. Because the PAM50 assay was designed to reflect the major features of the underlying biology of breast cancer, as opposed to being optimized against outcome in a particular population, it is particularly likely to extrapolate well onto other patient cohorts, and remain predictive [Rouzier 2005]. In this study, it was demonstrated for the first time that the PAM50 qPCR assay has significant and independent prognostic capacity among estrogen receptor positive, tamoxifen treated women, whether node positive or node negative. The assay identifies up to 10% cases that were clinically determined to be ER positive (by immunohistochemistry and ligand-binding assay) as falling into ER negative high-risk groups, replaces grade and HER2 status in multivariate prognostic models, and is superior to immunohistochemical subtyping and clinical risk classifiers.

REFERENCES

Calza et al. (2006) Breast Cancer Res. 8:R34.
Cheang et al. (2006) J Clin Oncol. December 20; 24(36): 5637-44.
Cheang et al. (2008a) Annu Rev Pathol. 3:67-97.
Cheang M C et al. (2008b) Clin Cancer Res. 14(5):1368-76.
Cheang M C et al. (2009) J Natl Cancer Inst. 101(10):736-50.
Chia S et al. (2008) J Clin Oncol. 26(35):5697-704.
Cox and Oakes (1984) Analysis of Survival Data. Chapman & Hall (London, England).
Cronin M et al. (2007) Clin Chem 53:1084-91.
Fan et al. (2006) N. Engl. J. Med. 355:560-69.
Glas et al. (2006) BMC Genomics 7:278.
Grambsch and Therneau (1994) Biometrika 81(3):515-26.
Hayes et al. (2007) N Engl J. Med. 357(15):1496-506.
Hu et al. (2006) BMC Genomics 7:96.
Kapp et al. (2006) BMC Genomics 7:231.
Loi et al. (2007) J Clin Oncol. 25(10):1239-46.
Mullins et al. (2007) Clin Chem. 53(7):1273-9.
Oh D S et al. (2006) J Clin Oncol. 24(11):1656-64.
Olivotto et al. (2005) J Clin Oncol 23:2716-25.
Paik (2004) N. Engl. J. Med. 351:2817-26.
Parker et al. (2009) J Clin Oncol. 27(8):1160-1167.
Ross et al. (2008) Clin Cancer Res. 14(20):6602-9.
Rouzier R et al. (2005) Clin Cancer Res. 11(16):5678-85.
Sorlie et al. (2003) Proc Natl Acad Sci USA. 100(14):8418-23.
Sotiriou et al. (2006) J Natl Cancer Inst 98:262-272.
Tibshirani et al. (2002) Proc Natl Acad Sci USA. 99(10): 6567-72.
Truong et al. (2005) Cancer 103(10):2006-14.
van't Veer et al. (2005) J Clin Oncol. 23(8):1631-5.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

What is claimed:

1. A method comprising:

(a) providing a biological sample of a subject, and (b) assaying nucleic acid molecules derived from RNA expression products of said biological sample to determine RNA expression levels corresponding to genes of said subject wherein said assaying comprises use of capture probes having sequences complementary to said nucleic acid molecules derived from said RNA expression products;

(c) generating a gene expression profile comprising RNA expression levels for a plurality of genes consisting of (i) 40 to 50 genes selected from ACTR3B, ANLN, BAG1, BCL2, BIRC5, BLVRA, CCNB1, CCNE1, CDC20, CDC6, CDCA1, CDH3, CENPF, CEP55, CXXC5, EGFR, ERBB2, ESR1, EXO1, FGFR4, FOXA1, FOXC1, GPR160, GRB7, HSPC150 (UBE2T), KIF2C, KNTC2, KRT14, KRT17, KRT5, MAPT, MDM2, MELK, MIA, MKI67, MLPH, MMP11, MYBL2, MYC, NAT1, ORC6L, PGR, PHGDH, PTTG1, RRM2, SFRP1, SLC39A6, TMEM45B, TYMS, and UBE2C and (ii) a set of housekeeping genes;

(d) comparing said gene expression profile to each of a set of centroids, wherein said set of centroids correspond to a plurality of breast cancer intrinsic subtypes; and (e) assigning said biological sample to a breast cancer intrinsic subtype of said plurality of breast cancer intrinsic subtypes corresponding to a centroid among said set of centroids based at least upon a distance of said gene expression profile to said centroid.

2. The method of claim 1, wherein said subject has been diagnosed with cancer.

3. The method of claim 2, wherein said cancer is breast cancer.

4. The method of claim 3, wherein said biological sample is a breast tumor tissue sample.

5. The method of claim 4, wherein said breast tumor tissue sample is a formalin-fixed paraffin-embedded (FFPE) breast tumor tissue sample.

6. The method of claim 1, wherein said subject is undergoing a breast cancer therapy.

7. The method of claim 6, wherein said breast cancer therapy is an endocrine therapy.

8. The method of claim 7, wherein said endocrine therapy is a neoadjuvant endocrine therapy.

9. The method of claim 6, wherein said breast cancer therapy is a chemotherapy.

10. The method of claim 1, wherein said plurality of genes consists of (i) 42 to 50 genes selected from ACTR3B, ANLN, BAG1, BCL2, BIRC5, BLVRA, CCNB1, CCNE1, CDC20, CDC6, CDCA1, CDH3, CENPF, CEP55, CXXC5, EGFR, ERBB2, ESR1, EXO1, FGFR4, FOXA1, FOXC1, GPR160, GRB7, HSPC150 (UBE2T), KIF2C, KNTC2, KRT14, KRT17, KRT5, MAPT, MDM2, MELK, MIA, MKI67, MLPH, MMP11, MYBL2, MYC, NAT1, ORC6L, PGR, PHGDH, PTTG1, RRM2, SFRP1, SLC39A6, TMEM45B, TYMS, and UBE2C and (ii) a set of housekeeping genes.

11. The method of claim 1, wherein said plurality of genes consists of (i) 44 to 50 genes selected from ACTR3B, ANLN, BAG1, BCL2, BIRC5, BLVRA, CCNB1, CCNE1, CDC20, CDC6, CDCA1, CDH3, CENPF, CEP55, CXXC5, EGFR, ERBB2, ESR1, EXO1, FGFR4, FOXA1, FOXC1, GPR160, GRB7, HSPC150 (UBE2T), KIF2C, KNTC2, KRT14, KRT17, KRT5, MAPT, MDM2, MELK, MIA, MKI67, MLPH, MMP11, MYBL2, MYC, NAT1, ORC6L, PGR, PHGDH, PTTG1, RRM2, SFRP1, SLC39A6, TMEM45B, TYMS, and UBE2C and (ii) a set of house- keeping genes.

12. The method of claim 1, wherein said plurality of genes consists of (i) 46 to 50 genes selected from ACTR3B, ANLN, BAG1, BCL2, BIRC5, BLVRA, CCNB1, CCNE1, CDC20, CDC6, CDCA1, CDH3, CENPF, CEP55, CXXC5, EGFR, ERBB2, ESR1, EXO1, FGFR4, FOXA1, FOXC1, GPR160, GRB7, HSPC150 (UBE2T), KIF2C, KNTC2, KRT14, KRT17, KRT5, MAPT, MDM2, MELK, MIA, MKI67, MLPH, MMP11, MYBL2, MYC, NAT1, ORC6L, PGR, PHGDH, PTTG1, RRM2, SFRP1, SLC39A6, TMEM45B, TYMS, and UBE2C and (ii) a set of house- keeping genes.

13. The method of claim 1, wherein said plurality of genes consists of (i) 48 to 50 genes selected from ACTR3B, ANLN, BAG1, BCL2, BIRC5, BLVRA, CCNB1, CCNE1, CDC20, CDC6, CDCA1, CDH3, CENPF, CEP55, CXXC5, EGFR, ERBB2, ESR1, EXO1, FGFR4, FOXA1, FOXC1, GPR160, GRB7, HSPC150 (UBE2T), KIF2C, KNTC2, KRT14, KRT17, KRT5, MAPT, MDM2, MELK, MIA, MKI67, MLPH, MMP11, MYBL2, MYC, NAT1, ORC6L, PGR, PHGDH, PTTG1, RRM2, SFRP1, SLC39A6, TMEM45B, TYMS, and UBE2C and (ii) a set of house- keeping genes.

14. The method of claim 1, further comprising:
wherein said set of centroids is constructed at least in part by:
(1) detecting RNA expression levels of said plurality of genes in a plurality of training breast cancer samples that have been classified according to breast cancer intrinsic subtype, thereby generating a training gene expression profile, wherein each of the Luminal A (LumA), Luminal B (LumB), Basal-like (Basal), and HER2-enriched (HER2) breast cancer intrinsic sub- types is represented in the plurality of training breast cancer samples, and (2) constructing centroids for each of said breast cancer intrinsic subtypes in said plurality of training breast cancer samples, at least in part by comparing, using a nearest centroid algorithm, said training gene expres- sion profile of said training breast cancer samples to reference gene expression data.

15. The method of claim 1, further comprising predicting a response or a non-response to neoadjuvant therapy in the subject based at least in part on said assigning in (e), wherein said breast cancer intrinsic subtype assigned in (e) is indica- tive of said predicted response or non-response to said neoadjuvant therapy.

16. The method of claim 15, wherein said neoadjuvant therapy is neoadjuvant endocrine therapy, and wherein said biological sample is obtained from said subject after initia- tion of said neoadjuvant endocrine therapy.

17. The method of claim 15, further comprising predicting a response to said neoadjuvant therapy in said subject.

18. The method of claim 17, further comprising admin- istering said neoadjuvant therapy to said subject responsive to said predicting.

19. The method of claim 1, wherein said RNA expression levels of said plurality of genes are normalized prior to said comparing in (d).

20. The method of claim 19, wherein said normalizing comprises normalization to said set of housekeeping genes.

21. The method of claim 1, wherein said set of house- keeping genes comprise a gene selected from the group consisting of MRPL19, PSMC4, SF3A1, PUM1, ACTB, GAPD, GUSB, RPLPO, and TFRC.

22. The method of claim 1, wherein the subject is node- negative.

23. The method of claim 1, wherein the subject is node- positive.

24. The method of claim 1, further comprising determin- ing a likelihood of breast cancer recurrence of the subject.

* * * * *

SEQUENCE LISTING

```
Sequence total quantity: 100
SEQ ID NO: 1              moltype = DNA  length = 19
FEATURE                   Location/Qualifiers
misc_feature              1..19
                          note = Oligonucleotide primer
source                    1..19
                          mol_type = other DNA
                          organism = synthetic construct
SEQUENCE: 1
aaagattcct gggacctga                                          19

SEQ ID NO: 2              moltype = DNA  length = 21
FEATURE                   Location/Qualifiers
misc_feature              1..21
                          note = Oligonucleotide primer
source                    1..21
```

-continued

```
                            mol_type = other DNA
                            organism = synthetic construct
SEQUENCE: 2
acagccactt tcagaagcaa g                                              21

SEQ ID NO: 3          moltype = DNA   length = 22
FEATURE               Location/Qualifiers
misc_feature          1..22
                      note = Oligonucleotide primer
source                1..22
                      mol_type = other DNA
                      organism = synthetic construct
SEQUENCE: 3
ctggaagagt tgaataaaga gc                                             22

SEQ ID NO: 4          moltype = DNA   length = 18
FEATURE               Location/Qualifiers
misc_feature          1..18
                      note = Oligonucleotide primer
source                1..18
                      mol_type = other DNA
                      organism = synthetic construct
SEQUENCE: 4
tacctgaacc ggcacctg                                                  18

SEQ ID NO: 5          moltype = DNA   length = 20
FEATURE               Location/Qualifiers
misc_feature          1..20
                      note = Oligonucleotide primer
source                1..20
                      mol_type = other DNA
                      organism = synthetic construct
SEQUENCE: 5
gcacaaagcc attctaagtc                                                20

SEQ ID NO: 6          moltype = DNA   length = 17
FEATURE               Location/Qualifiers
misc_feature          1..17
                      note = Oligonucleotide primer
source                1..17
                      mol_type = other DNA
                      organism = synthetic construct
SEQUENCE: 6
gctggctgag cagaaag                                                   17

SEQ ID NO: 7          moltype = DNA   length = 19
FEATURE               Location/Qualifiers
misc_feature          1..19
                      note = Oligonucleotide primer
source                1..19
                      mol_type = other DNA
                      organism = synthetic construct
SEQUENCE: 7
ctttcgcctg agcctattt                                                 19

SEQ ID NO: 8          moltype = DNA   length = 18
FEATURE               Location/Qualifiers
misc_feature          1..18
                      note = Oligonucleotide primer
source                1..18
                      mol_type = other DNA
                      organism = synthetic construct
SEQUENCE: 8
ggccaaaatc gacaggac                                                  18

SEQ ID NO: 9          moltype = DNA   length = 19
FEATURE               Location/Qualifiers
misc_feature          1..19
                      note = Oligonucleotide primer
source                1..19
                      mol_type = other DNA
                      organism = synthetic construct
SEQUENCE: 9
ctgtctgagt gccgtggat                                                 19

SEQ ID NO: 10         moltype = DNA   length = 20
FEATURE               Location/Qualifiers
misc_feature          1..20
                      note = Oligonucleotide primer
```

-continued

```
source                  1..20
                        mol_type = other DNA
                        organism = synthetic construct
SEQUENCE: 10
gtaaatcacc ttctgagcct                                          20

SEQ ID NO: 11          moltype = DNA   length = 18
FEATURE                Location/Qualifiers
misc_feature           1..18
                        note = Oligonucleotide primer
source                  1..18
                        mol_type = other DNA
                        organism = synthetic construct
SEQUENCE: 11
ggaggcggaa gaaaccag                                            18

SEQ ID NO: 12          moltype = DNA   length = 24
FEATURE                Location/Qualifiers
misc_feature           1..24
                        note = Oligonucleotide primer
source                  1..24
                        mol_type = other DNA
                        organism = synthetic construct
SEQUENCE: 12
gacaaggaga atcaaaagat cagc                                     24

SEQ ID NO: 13          moltype = DNA   length = 17
FEATURE                Location/Qualifiers
misc_feature           1..17
                        note = Oligonucleotide primer
source                  1..17
                        mol_type = other DNA
                        organism = synthetic construct
SEQUENCE: 13
gtggcagcag atcacaa                                             17

SEQ ID NO: 14          moltype = DNA   length = 20
FEATURE                Location/Qualifiers
misc_feature           1..20
                        note = Oligonucleotide primer
source                  1..20
                        mol_type = other DNA
                        organism = synthetic construct
SEQUENCE: 14
cctcacgaat tgctgaactt                                          20

SEQ ID NO: 15          moltype = DNA   length = 23
FEATURE                Location/Qualifiers
misc_feature           1..23
                        note = Oligonucleotide primer
source                  1..23
                        mol_type = other DNA
                        organism = synthetic construct
SEQUENCE: 15
catgaaatag tgcatagttt gcc                                      23

SEQ ID NO: 16          moltype = DNA   length = 25
FEATURE                Location/Qualifiers
misc_feature           1..25
                        note = Oligonucleotide primer
source                  1..25
                        mol_type = other DNA
                        organism = synthetic construct
SEQUENCE: 16
acacagaatc tatacccacc agagt                                    25

SEQ ID NO: 17          moltype = DNA   length = 20
FEATURE                Location/Qualifiers
misc_feature           1..20
                        note = Oligonucleotide primer
source                  1..20
                        mol_type = other DNA
                        organism = synthetic construct
SEQUENCE: 17
gctggctctc acactgatag                                          20

SEQ ID NO: 18          moltype = DNA   length = 18
FEATURE                Location/Qualifiers
misc_feature           1..18
```

```
                          note = Oligonucleotide primer
source                    1..18
                          mol_type = other DNA
                          organism = synthetic construct
SEQUENCE: 18
gcagggagag gagtttgt                                              18

SEQ ID NO: 19             moltype = DNA   length = 23
FEATURE                   Location/Qualifiers
misc_feature              1..23
                          note = Oligonucleotide primer
source                    1..23
                          mol_type = other DNA
                          organism = synthetic construct
SEQUENCE: 19
cccatccatg tgaggaagta taa                                        23

SEQ ID NO: 20             moltype = DNA   length = 17
FEATURE                   Location/Qualifiers
misc_feature              1..17
                          note = Oligonucleotide primer
source                    1..17
                          mol_type = other DNA
                          organism = synthetic construct
SEQUENCE: 20
cttcttggac cttggcg                                               17

SEQ ID NO: 21             moltype = DNA   length = 17
FEATURE                   Location/Qualifiers
misc_feature              1..17
                          note = Oligonucleotide primer
source                    1..17
                          mol_type = other DNA
                          organism = synthetic construct
SEQUENCE: 21
gctactacgc agacacg                                               17

SEQ ID NO: 22             moltype = DNA   length = 19
FEATURE                   Location/Qualifiers
misc_feature              1..19
                          note = Oligonucleotide primer
source                    1..19
                          mol_type = other DNA
                          organism = synthetic construct
SEQUENCE: 22
gatgttcgag tcacagagg                                             19

SEQ ID NO: 23             moltype = DNA   length = 17
FEATURE                   Location/Qualifiers
misc_feature              1..17
                          note = Oligonucleotide primer
source                    1..17
                          mol_type = other DNA
                          organism = synthetic construct
SEQUENCE: 23
ttcggctgga aggaacc                                               17

SEQ ID NO: 24             moltype = DNA   length = 18
FEATURE                   Location/Qualifiers
misc_feature              1..18
                          note = Oligonucleotide primer
source                    1..18
                          mol_type = other DNA
                          organism = synthetic construct
SEQUENCE: 24
cgtggcagat gtgaacga                                              18

SEQ ID NO: 25             moltype = DNA   length = 20
FEATURE                   Location/Qualifiers
misc_feature              1..20
                          note = Oligonucleotide primer
source                    1..20
                          mol_type = other DNA
                          organism = synthetic construct
SEQUENCE: 25
ggagatccgt caactccaaa                                            20

SEQ ID NO: 26             moltype = DNA   length = 18
FEATURE                   Location/Qualifiers
```

```
misc_feature         1..18
                     note = Oligonucleotide primer
source               1..18
                     mol_type = other DNA
                     organism = synthetic construct
SEQUENCE: 26
tgggtcgtgt caggaaac                                           18

SEQ ID NO: 27        moltype = DNA  length = 20
FEATURE              Location/Qualifiers
misc_feature         1..20
                     note = Oligonucleotide primer
source               1..20
                     mol_type = other DNA
                     organism = synthetic construct
SEQUENCE: 27
cgcagtcatc cagagatgtg                                         20

SEQ ID NO: 28        moltype = DNA  length = 21
FEATURE              Location/Qualifiers
misc_feature         1..21
                     note = Oligonucleotide primer
source               1..21
                     mol_type = other DNA
                     organism = synthetic construct
SEQUENCE: 28
actcagtaca agaaagaacc g                                       21

SEQ ID NO: 29        moltype = DNA  length = 22
FEATURE              Location/Qualifiers
misc_feature         1..22
                     note = Oligonucleotide primer
source               1..22
                     mol_type = other DNA
                     organism = synthetic construct
SEQUENCE: 29
gttggaccag tcaacatctc tg                                      22

SEQ ID NO: 30        moltype = DNA  length = 18
FEATURE              Location/Qualifiers
misc_feature         1..18
                     note = Oligonucleotide primer
source               1..18
                     mol_type = other DNA
                     organism = synthetic construct
SEQUENCE: 30
tgtggctcat taggcaac                                           18

SEQ ID NO: 31        moltype = DNA  length = 18
FEATURE              Location/Qualifiers
misc_feature         1..18
                     note = Oligonucleotide primer
source               1..18
                     mol_type = other DNA
                     organism = synthetic construct
SEQUENCE: 31
gactccaagc gcgaaaac                                           18

SEQ ID NO: 32        moltype = DNA  length = 24
FEATURE              Location/Qualifiers
misc_feature         1..24
                     note = Oligonucleotide primer
source               1..24
                     mol_type = other DNA
                     organism = synthetic construct
SEQUENCE: 32
ccaacaaaat attcatggtt cttg                                    24

SEQ ID NO: 33        moltype = DNA  length = 18
FEATURE              Location/Qualifiers
misc_feature         1..18
                     note = Oligonucleotide primer
source               1..18
                     mol_type = other DNA
                     organism = synthetic construct
SEQUENCE: 33
ccagtagcat tgtccgag                                           18

SEQ ID NO: 34        moltype = DNA  length = 19
```

-continued

```
FEATURE              Location/Qualifiers
misc_feature         1..19
                     note = Oligonucleotide primer
source               1..19
                     mol_type = other DNA
                     organism = synthetic construct
SEQUENCE: 34
gtctctggta atgcacact                                           19

SEQ ID NO: 35        moltype = DNA   length = 18
FEATURE              Location/Qualifiers
misc_feature         1..18
                     note = Oligonucleotide primer
source               1..18
                     mol_type = other DNA
                     organism = synthetic construct
SEQUENCE: 35
gtggaatgcc tgctgacc                                            18

SEQ ID NO: 36        moltype = DNA   length = 18
FEATURE              Location/Qualifiers
misc_feature         1..18
                     note = Oligonucleotide primer
source               1..18
                     mol_type = other DNA
                     organism = synthetic construct
SEQUENCE: 36
aggggtgccc tctgagat                                            18

SEQ ID NO: 37        moltype = DNA   length = 18
FEATURE              Location/Qualifiers
misc_feature         1..18
                     note = Oligonucleotide primer
source               1..18
                     mol_type = other DNA
                     organism = synthetic construct
SEQUENCE: 37
cgagatcgcc aagatgtt                                            18

SEQ ID NO: 38        moltype = DNA   length = 18
FEATURE              Location/Qualifiers
misc_feature         1..18
                     note = Oligonucleotide primer
source               1..18
                     mol_type = other DNA
                     organism = synthetic construct
SEQUENCE: 38
aggcgaacac acaacgtc                                            18

SEQ ID NO: 39        moltype = DNA   length = 19
FEATURE              Location/Qualifiers
misc_feature         1..19
                     note = Oligonucleotide primer
source               1..19
                     mol_type = other DNA
                     organism = synthetic construct
SEQUENCE: 39
agcctcgaac aattgaaga                                           19

SEQ ID NO: 40        moltype = DNA   length = 27
FEATURE              Location/Qualifiers
misc_feature         1..27
                     note = Oligonucleotide primer
source               1..27
                     mol_type = other DNA
                     organism = synthetic construct
SEQUENCE: 40
atcgactgtg taaacaacta gagaaga                                  27

SEQ ID NO: 41        moltype = DNA   length = 20
FEATURE              Location/Qualifiers
misc_feature         1..20
                     note = Oligonucleotide primer
source               1..20
                     mol_type = other DNA
                     organism = synthetic construct
SEQUENCE: 41
tttaagaggg caatggaagg                                          20
```

```
SEQ ID NO: 42       moltype = DNA   length = 18
FEATURE             Location/Qualifiers
misc_feature        1..18
                    note = Oligonucleotide primer
source              1..18
                    mol_type = other DNA
                    organism = synthetic construct
SEQUENCE: 42
tgccgcagaa ctcacttg                                        18

SEQ ID NO: 43       moltype = DNA   length = 20
FEATURE             Location/Qualifiers
misc_feature        1..20
                    note = Oligonucleotide primer
source              1..20
                    mol_type = other DNA
                    organism = synthetic construct
SEQUENCE: 43
cctcagatga tgcctatcca                                      20

SEQ ID NO: 44       moltype = DNA   length = 19
FEATURE             Location/Qualifiers
misc_feature        1..19
                    note = Oligonucleotide primer
source              1..19
                    mol_type = other DNA
                    organism = synthetic construct
SEQUENCE: 44
cagcaagcga tggcatagt                                       19

SEQ ID NO: 45       moltype = DNA   length = 17
FEATURE             Location/Qualifiers
misc_feature        1..17
                    note = Oligonucleotide primer
source              1..17
                    mol_type = other DNA
                    organism = synthetic construct
SEQUENCE: 45
aatgccaccg aagcctc                                         17

SEQ ID NO: 46       moltype = DNA   length = 23
FEATURE             Location/Qualifiers
misc_feature        1..23
                    note = Oligonucleotide primer
source              1..23
                    mol_type = other DNA
                    organism = synthetic construct
SEQUENCE: 46
tcgaactgaa ggctatttac gag                                  23

SEQ ID NO: 47       moltype = DNA   length = 18
FEATURE             Location/Qualifiers
misc_feature        1..18
                    note = Oligonucleotide primer
source              1..18
                    mol_type = other DNA
                    organism = synthetic construct
SEQUENCE: 47
gtcgaagccg caattagg                                        18

SEQ ID NO: 48       moltype = DNA   length = 20
FEATURE             Location/Qualifiers
misc_feature        1..20
                    note = Oligonucleotide primer
source              1..20
                    mol_type = other DNA
                    organism = synthetic construct
SEQUENCE: 48
caaacgtgtg ttctggaagg                                      20

SEQ ID NO: 49       moltype = DNA   length = 20
FEATURE             Location/Qualifiers
misc_feature        1..20
                    note = Oligonucleotide primer
source              1..20
                    mol_type = other DNA
                    organism = synthetic construct
SEQUENCE: 49
tgccctgtat gatgtcagga                                      20
```

-continued

```
SEQ ID NO: 50          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 50
gtgaggggtg tcagctcagt                                            20

SEQ ID NO: 51          moltype = DNA   length = 22
FEATURE                Location/Qualifiers
misc_feature           1..22
                       note = Oligonucleotide primer
source                 1..22
                       mol_type = other DNA
                       organism = synthetic construct
SEQUENCE: 51
tggggcagtt ctgtattact tc                                         22

SEQ ID NO: 52          moltype = DNA   length = 24
FEATURE                Location/Qualifiers
misc_feature           1..24
                       note = Oligonucleotide primer
source                 1..24
                       mol_type = other DNA
                       organism = synthetic construct
SEQUENCE: 52
cgatggtttt gtacaagatt tctc                                       24

SEQ ID NO: 53          moltype = DNA   length = 17
FEATURE                Location/Qualifiers
misc_feature           1..17
                       note = Oligonucleotide primer
source                 1..17
                       mol_type = other DNA
                       organism = synthetic construct
SEQUENCE: 53
gcaaatcctt gggcaga                                               17

SEQ ID NO: 54          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 54
gccgtacagt tccacaaagg                                            20

SEQ ID NO: 55          moltype = DNA   length = 22
FEATURE                Location/Qualifiers
misc_feature           1..22
                       note = Oligonucleotide primer
source                 1..22
                       mol_type = other DNA
                       organism = synthetic construct
SEQUENCE: 55
gacgcttcct atcactctat tc                                         22

SEQ ID NO: 56          moltype = DNA   length = 22
FEATURE                Location/Qualifiers
misc_feature           1..22
                       note = Oligonucleotide primer
source                 1..22
                       mol_type = other DNA
                       organism = synthetic construct
SEQUENCE: 56
ttcctccatc aagagttcaa ca                                         22

SEQ ID NO: 57          moltype = DNA   length = 18
FEATURE                Location/Qualifiers
misc_feature           1..18
                       note = Oligonucleotide primer
source                 1..18
                       mol_type = other DNA
                       organism = synthetic construct
SEQUENCE: 57
```

-continued

```
gggcacatcc agatgttt                                                   18

SEQ ID NO: 58          moltype = DNA   length = 19
FEATURE                Location/Qualifiers
misc_feature           1..19
                       note = Oligonucleotide primer
source                 1..19
                       mol_type = other DNA
                       organism = synthetic construct
SEQUENCE: 58
gggtctgcac agactgcat                                                  19

SEQ ID NO: 59          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 59
tccttgtaat ggggagacca                                                 20

SEQ ID NO: 60          moltype = DNA   length = 23
FEATURE                Location/Qualifiers
misc_feature           1..23
                       note = Oligonucleotide primer
source                 1..23
                       mol_type = other DNA
                       organism = synthetic construct
SEQUENCE: 60
acttgggata tgtgaataag acc                                             23

SEQ ID NO: 61          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 61
ggggaaagac aaagtttcca                                                 20

SEQ ID NO: 62          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 62
actgtctggg tccatggcta                                                 20

SEQ ID NO: 63          moltype = DNA   length = 18
FEATURE                Location/Qualifiers
misc_feature           1..18
                       note = Oligonucleotide primer
source                 1..18
                       mol_type = other DNA
                       organism = synthetic construct
SEQUENCE: 63
ggatttcgtg gtgggttc                                                   18

SEQ ID NO: 64          moltype = DNA   length = 20
FEATURE                Location/Qualifiers
misc_feature           1..20
                       note = Oligonucleotide primer
source                 1..20
                       mol_type = other DNA
                       organism = synthetic construct
SEQUENCE: 64
ccacagtctg tgataaacgg                                                 20

SEQ ID NO: 65          moltype = DNA   length = 24
FEATURE                Location/Qualifiers
misc_feature           1..24
                       note = Oligonucleotide primer
source                 1..24
                       mol_type = other DNA
                       organism = synthetic construct
```

-continued

```
SEQUENCE: 65
ccatcaacat tctctttatg aacg                                           24

SEQ ID NO: 66            moltype = DNA   length = 20
FEATURE                  Location/Qualifiers
misc_feature             1..20
                         note = Oligonucleotide primer
source                   1..20
                         mol_type = other DNA
                         organism = synthetic construct
SEQUENCE: 66
atcaactccc aaacggtcac                                                20

SEQ ID NO: 67            moltype = DNA   length = 20
FEATURE                  Location/Qualifiers
misc_feature             1..20
                         note = Oligonucleotide primer
source                   1..20
                         mol_type = other DNA
                         organism = synthetic construct
SEQUENCE: 67
gcccttacac atcggagaac                                                20

SEQ ID NO: 68            moltype = DNA   length = 18
FEATURE                  Location/Qualifiers
misc_feature             1..18
                         note = Oligonucleotide primer
source                   1..18
                         mol_type = other DNA
                         organism = synthetic construct
SEQUENCE: 68
gacttcaggg tgctggac                                                  18

SEQ ID NO: 69            moltype = DNA   length = 22
FEATURE                  Location/Qualifiers
misc_feature             1..22
                         note = Oligonucleotide primer
source                   1..22
                         mol_type = other DNA
                         organism = synthetic construct
SEQUENCE: 69
tgtgaagcca gcaatatgta tc                                             22

SEQ ID NO: 70            moltype = DNA   length = 21
FEATURE                  Location/Qualifiers
misc_feature             1..21
                         note = Oligonucleotide primer
source                   1..21
                         mol_type = other DNA
                         organism = synthetic construct
SEQUENCE: 70
tattgggagg caggaggttt a                                              21

SEQ ID NO: 71            moltype = DNA   length = 20
FEATURE                  Location/Qualifiers
misc_feature             1..20
                         note = Oligonucleotide primer
source                   1..20
                         mol_type = other DNA
                         organism = synthetic construct
SEQUENCE: 71
ctgagttcat gttgctgacc                                                20

SEQ ID NO: 72            moltype = DNA   length = 19
FEATURE                  Location/Qualifiers
misc_feature             1..19
                         note = Oligonucleotide primer
source                   1..19
                         mol_type = other DNA
                         organism = synthetic construct
SEQUENCE: 72
gacagctact attcccgtt                                                 19

SEQ ID NO: 73            moltype = DNA   length = 21
FEATURE                  Location/Qualifiers
misc_feature             1..21
                         note = Oligonucleotide primer
source                   1..21
                         mol_type = other DNA
```

-continued

```
                          organism = synthetic construct
SEQUENCE: 73
tatgtgagta agctcggaga c                                          21

SEQ ID NO: 74             moltype = DNA  length = 17
FEATURE                   Location/Qualifiers
misc_feature              1..17
                          note = Oligonucleotide primer
source                    1..17
                          mol_type = other DNA
                          organism = synthetic construct
SEQUENCE: 74
agtgggcatc ccgtaga                                               17

SEQ ID NO: 75             moltype = DNA  length = 19
FEATURE                   Location/Qualifiers
misc_feature              1..19
                          note = Oligonucleotide primer
source                    1..19
                          mol_type = other DNA
                          organism = synthetic construct
SEQUENCE: 75
agtggacatg cgagtggag                                             19

SEQ ID NO: 76             moltype = DNA  length = 18
FEATURE                   Location/Qualifiers
misc_feature              1..18
                          note = Oligonucleotide primer
source                    1..18
                          mol_type = other DNA
                          organism = synthetic construct
SEQUENCE: 76
caccgctgga aactgaac                                              18

SEQ ID NO: 77             moltype = DNA  length = 19
FEATURE                   Location/Qualifiers
misc_feature              1..19
                          note = Oligonucleotide primer
source                    1..19
                          mol_type = other DNA
                          organism = synthetic construct
SEQUENCE: 77
cgtgcacatc catgacctt                                             19

SEQ ID NO: 78             moltype = DNA  length = 17
FEATURE                   Location/Qualifiers
misc_feature              1..17
                          note = Oligonucleotide primer
source                    1..17
                          mol_type = other DNA
                          organism = synthetic construct
SEQUENCE: 78
gaggagatga ccttgcc                                               17

SEQ ID NO: 79             moltype = DNA  length = 18
FEATURE                   Location/Qualifiers
misc_feature              1..18
                          note = Oligonucleotide primer
source                    1..18
                          mol_type = other DNA
                          organism = synthetic construct
SEQUENCE: 79
gccatagcca ctgccact                                              18

SEQ ID NO: 80             moltype = DNA  length = 17
FEATURE                   Location/Qualifiers
misc_feature              1..17
                          note = Oligonucleotide primer
source                    1..17
                          mol_type = other DNA
                          organism = synthetic construct
SEQUENCE: 80
cttcgactgg actctgt                                               17

SEQ ID NO: 81             moltype = DNA  length = 23
FEATURE                   Location/Qualifiers
misc_feature              1..23
                          note = Oligonucleotide primer
source                    1..23
```

-continued

```
                              mol_type = other DNA
                              organism = synthetic construct
SEQUENCE: 81
cagacatgtt ggtattgcac att                                              23

SEQ ID NO: 82          moltype = DNA  length = 20
FEATURE                Location/Qualifiers
misc_feature           1..20
                       note = Oligonucleotide primer
source                 1..20
                       mol_type = other DNA
                       organism = synthetic construct
SEQUENCE: 82
aggcgatcct gggaaattat                                                  20

SEQ ID NO: 83          moltype = DNA  length = 19
FEATURE                Location/Qualifiers
misc_feature           1..19
                       note = Oligonucleotide primer
source                 1..19
                       mol_type = other DNA
                       organism = synthetic construct
SEQUENCE: 83
cccatttgtc tgtcttcac                                                   19

SEQ ID NO: 84          moltype = DNA  length = 18
FEATURE                Location/Qualifiers
misc_feature           1..18
                       note = Oligonucleotide primer
source                 1..18
                       mol_type = other DNA
                       organism = synthetic construct
SEQUENCE: 84
ctgatggttg aggctgtt                                                    18

SEQ ID NO: 85          moltype = DNA  length = 19
FEATURE                Location/Qualifiers
misc_feature           1..19
                       note = Oligonucleotide primer
source                 1..19
                       mol_type = other DNA
                       organism = synthetic construct
SEQUENCE: 85
cgcactccag cacctagac                                                   19

SEQ ID NO: 86          moltype = DNA  length = 21
FEATURE                Location/Qualifiers
misc_feature           1..21
                       note = Oligonucleotide primer
source                 1..21
                       mol_type = other DNA
                       organism = synthetic construct
SEQUENCE: 86
tcacagggtc aaacttccag t                                                21

SEQ ID NO: 87          moltype = DNA  length = 21
FEATURE                Location/Qualifiers
misc_feature           1..21
                       note = Oligonucleotide primer
source                 1..21
                       mol_type = other DNA
                       organism = synthetic construct
SEQUENCE: 87
gatggtagag ttccagtgat t                                                21

SEQ ID NO: 88          moltype = DNA  length = 18
FEATURE                Location/Qualifiers
misc_feature           1..18
                       note = Oligonucleotide primer
source                 1..18
                       mol_type = other DNA
                       organism = synthetic construct
SEQUENCE: 88
tctggtcacg cagggcaa                                                    18

SEQ ID NO: 89          moltype = DNA  length = 20
FEATURE                Location/Qualifiers
misc_feature           1..20
                       note = Oligonucleotide primer
```

-continued

```
source                       1..20
                             mol_type = other DNA
                             organism = synthetic construct
SEQUENCE: 89
acacagatga tggagatgtc                                                       20

SEQ ID NO: 90               moltype = DNA   length = 25
FEATURE                     Location/Qualifiers
misc_feature                1..25
                            note = Oligonucleotide primer
source                      1..25
                            mol_type = other DNA
                            organism = synthetic construct
SEQUENCE: 90
agtagctaca tctccaggtt ctctg                                                 25

SEQ ID NO: 91               moltype = DNA   length = 21
FEATURE                     Location/Qualifiers
misc_feature                1..21
                            note = Oligonucleotide primer
source                      1..21
                            mol_type = other DNA
                            organism = synthetic construct
SEQUENCE: 91
cggattttat caacgatgca g                                                     21

SEQ ID NO: 92               moltype = DNA   length = 19
FEATURE                     Location/Qualifiers
misc_feature                1..19
                            note = Oligonucleotide primer
source                      1..19
                            mol_type = other DNA
                            organism = synthetic construct
SEQUENCE: 92
catttgccgt ccttcatcg                                                        19

SEQ ID NO: 93               moltype = DNA   length = 20
FEATURE                     Location/Qualifiers
misc_feature                1..20
                            note = Oligonucleotide primer
source                      1..20
                            mol_type = other DNA
                            organism = synthetic construct
SEQUENCE: 93
gcaggtcaaa actctcaaag                                                       20

SEQ ID NO: 94               moltype = DNA   length = 20
FEATURE                     Location/Qualifiers
misc_feature                1..20
                            note = Oligonucleotide primer
source                      1..20
                            mol_type = other DNA
                            organism = synthetic construct
SEQUENCE: 94
agcgggcttc tgtaatctga                                                       20

SEQ ID NO: 95               moltype = DNA   length = 19
FEATURE                     Location/Qualifiers
misc_feature                1..19
                            note = Oligonucleotide primer
source                      1..19
                            mol_type = other DNA
                            organism = synthetic construct
SEQUENCE: 95
gcctcagatt tcaactcgt                                                        19

SEQ ID NO: 96               moltype = DNA   length = 21
FEATURE                     Location/Qualifiers
misc_feature                1..21
                            note = Oligonucleotide primer
source                      1..21
                            mol_type = other DNA
                            organism = synthetic construct
SEQUENCE: 96
ctgctgagaa tcaaagtggg a                                                     21

SEQ ID NO: 97               moltype = DNA   length = 19
FEATURE                     Location/Qualifiers
misc_feature                1..19
```

-continued

```
                        note = Oligonucleotide primer
source                  1..19
                        mol_type = other DNA
                        organism = synthetic construct
SEQUENCE: 97
ggaacaaact gctctgcca                                          19

SEQ ID NO: 98           moltype = DNA  length = 22
FEATURE                 Location/Qualifiers
misc_feature            1..22
                        note = Oligonucleotide primer
source                  1..22
                        mol_type = other DNA
                        organism = synthetic construct
SEQUENCE: 98
acagctcttt agcatttgtg ga                                      22

SEQ ID NO: 99           moltype = DNA  length = 23
FEATURE                 Location/Qualifiers
misc_feature            1..23
                        note = Oligonucleotide primer
source                  1..23
                        mol_type = other DNA
                        organism = synthetic construct
SEQUENCE: 99
gggactatca atgttgggtt ctc                                     23

SEQ ID NO: 100          moltype = DNA  length = 21
FEATURE                 Location/Qualifiers
misc_feature            1..21
                        note = Oligonucleotide primer
source                  1..21
                        mol_type = other DNA
                        organism = synthetic construct
SEQUENCE: 100
cacacagttc actgctccac a                                       21
```